(12) United States Patent
Bergheim et al.

(10) Patent No.: US 10,098,717 B2
(45) Date of Patent: Oct. 16, 2018

(54) APPARATUS AND METHODS FOR CLEANING TEETH AND GINGIVAL POCKETS

(71) Applicant: SONENDO, INC., Laguna Hills, CA (US)

(72) Inventors: Bjarne Bergheim, Mission Viejo, CA (US); Mehrzad Khakpour, Laguna Beach, CA (US)

(73) Assignee: SONENDO, INC., Laguna Hills, CA (US)

( * ) Notice: Subject to any disclaimer, the term of this patent is extended or adjusted under 35 U.S.C. 154(b) by 0 days.

(21) Appl. No.: 14/391,663

(22) PCT Filed: Apr. 12, 2013

(86) PCT No.: PCT/US2013/036493
§ 371 (c)(1),
(2) Date: Oct. 9, 2014

(87) PCT Pub. No.: WO2013/155492
PCT Pub. Date: Oct. 17, 2013

(65) Prior Publication Data
US 2015/0140503 A1    May 21, 2015

Related U.S. Application Data

(60) Provisional application No. 61/624,177, filed on Apr. 13, 2012, provisional application No. 61/801,682, filed on Mar. 15, 2013.

(51) Int. Cl.
*A61C 17/02* (2006.01)
*A61C 1/07* (2006.01)
(Continued)

(52) U.S. Cl.
CPC ........ *A61C 17/0211* (2013.01); *A61C 1/0007* (2013.01); *A61C 1/07* (2013.01);
(Continued)

(58) Field of Classification Search
CPC .. A61C 1/07; A61C 3/02; A61C 3/025; A61C 3/03; A61C 17/00; A61C 17/022;
(Continued)

(56) References Cited

U.S. PATENT DOCUMENTS

| 1,500,107 A | 7/1924 | Chandler |
| 2,108,558 A | 2/1938 | Jackman |

(Continued)

FOREIGN PATENT DOCUMENTS

| AU | 2012-202315 A1 | 4/2012 |
| AU | 2007140780 | 5/2014 |

(Continued)

OTHER PUBLICATIONS

European Extended Search Report, re EP Application No. 10830829.7, dated Oct. 21, 2015.
(Continued)

*Primary Examiner* — Nicholas Lucchesi
(74) *Attorney, Agent, or Firm* — Knobbe, Martens, Olson & Bear LLP

(57) ABSTRACT

Various apparatus and methods for cleaning teeth and gingival pockets are disclosed herein. A fluid platform can include a pressure wave generator configured to propagate pressure waves through a treatment fluid. The pressure waves may be sufficient to remove undesirable dental deposits from a treatment tooth, neighboring gums, and/or spaces between the tooth and gums.

43 Claims, 21 Drawing Sheets

(51) Int. Cl.
*A61C 17/20* (2006.01)
*A61C 1/00* (2006.01)

(52) U.S. Cl.
CPC .......... *A61C 17/02* (2013.01); *A61C 17/0208* (2013.01); *A61C 17/20* (2013.01); *A61C 17/0202* (2013.01)

(58) Field of Classification Search
CPC ... A61C 17/024; A61C 17/028; A61C 17/032; A61C 17/0211; A61C 1/0007; A61C 17/02; A61C 17/0208; A61C 17/20; A61C 17/0202
USPC ....... 433/81, 84, 85, 86, 114, 115, 118, 119, 433/216, 224, 80
See application file for complete search history.

(56) References Cited

U.S. PATENT DOCUMENTS

| | | |
|---|---|---|
| 3,023,306 A | 2/1962 | Kester |
| 3,401,690 A | 9/1968 | Martin |
| 3,460,255 A | 8/1969 | Hutson |
| 3,514,328 A | 5/1970 | Malin |
| 3,521,359 A | 7/1970 | Harris |
| 3,522,801 A | 8/1970 | Seymour |
| 3,547,110 A | 12/1970 | Balamuth |
| 3,561,433 A | 2/1971 | Kovach |
| 3,590,813 A | 7/1971 | Roszyk |
| 3,624,907 A | 12/1971 | Brass et al. |
| 3,703,170 A | 11/1972 | Ryckman, Jr. |
| 3,756,225 A | 9/1973 | Moret et al. |
| 3,828,770 A | 8/1974 | Kuris et al. |
| 3,921,296 A | 11/1975 | Harris |
| 3,930,505 A | 1/1976 | Wallach |
| 3,962,790 A | 6/1976 | Riitano et al. |
| 4,021,921 A | 5/1977 | Detaille |
| 4,060,600 A | 11/1977 | Vit |
| 4,215,476 A | 8/1980 | Armstrong |
| 4,247,288 A | 1/1981 | Yoshii et al. |
| 4,274,555 A | 6/1981 | Sneider |
| 4,276,880 A | 7/1981 | Malmin |
| 4,293,188 A | 10/1981 | McMahon |
| 4,376,835 A | 3/1983 | Schmitt et al. |
| 4,386,911 A | 6/1983 | Maloney et al. |
| 4,424,036 A | 1/1984 | Lokken |
| 4,474,251 A | 2/1984 | Johnson, Jr. |
| 4,492,575 A | 1/1985 | Mabille |
| 4,534,542 A | 8/1985 | Russo |
| 4,539,987 A | 9/1985 | Nath et al. |
| 4,608,017 A | 8/1986 | Sadohara |
| 4,659,218 A | 4/1987 | de Lasa et al. |
| 4,676,749 A | 6/1987 | Mabille |
| 4,684,781 A | 8/1987 | Frish et al. |
| 4,732,193 A | 3/1988 | Gibbs |
| 4,789,335 A | 12/1988 | Geller et al. |
| 4,872,837 A | 10/1989 | Issalene et al. |
| 4,941,459 A | 7/1990 | Mathur |
| 4,957,436 A | 9/1990 | Ryder |
| 4,973,246 A | 11/1990 | Black et al. |
| 4,985,027 A | 1/1991 | Dressel |
| 4,993,947 A | 2/1991 | Grosrey |
| 5,013,300 A | 5/1991 | Williams |
| 5,029,576 A | 7/1991 | Evans, Sr. |
| 5,037,431 A | 8/1991 | Summers et al. |
| 5,046,950 A | 9/1991 | Favonio |
| 5,055,048 A | 10/1991 | Vassiliadis et al. |
| 5,094,256 A | 3/1992 | Barth |
| 5,112,224 A | 5/1992 | Shirota |
| 5,188,532 A | 2/1993 | Levy |
| 5,188,634 A | 2/1993 | Hussein et al. |
| 5,194,723 A | 3/1993 | Cates et al. |
| 5,195,952 A | 3/1993 | Solnit et al. |
| 5,224,942 A | 7/1993 | Beuchat et al. |
| 5,267,856 A | 12/1993 | Wolbarsht et al. |
| 5,267,995 A | 12/1993 | Doiron et al. |
| 5,269,777 A | 12/1993 | Doiron et al. |
| 5,295,828 A | 3/1994 | Grosrey |
| 5,307,839 A | 5/1994 | Loebker et al. |
| 5,322,504 A | 6/1994 | Doherty et al. |
| 5,326,263 A | 7/1994 | Weissman |
| 5,334,019 A | 8/1994 | Goldsmith et al. |
| 5,380,201 A | 1/1995 | Kawata |
| 5,387,376 A | 2/1995 | Gasser |
| D356,866 S | 3/1995 | Meller |
| 5,399,089 A | 3/1995 | Eichman et al. |
| 5,428,699 A | 6/1995 | Pon |
| 5,435,724 A | 7/1995 | Goodman et al. |
| 5,474,451 A | 12/1995 | Dalrymple et al. |
| 5,490,779 A | 2/1996 | Malmin |
| 5,503,559 A | 4/1996 | Vari |
| 5,540,587 A | 7/1996 | Malmin |
| 5,547,376 A | 8/1996 | Harrel |
| 5,554,896 A | 9/1996 | Hogan |
| 5,562,692 A | 10/1996 | Bair |
| 5,564,929 A | 10/1996 | Alpert |
| 5,570,182 A | 10/1996 | Nathel et al. |
| 5,591,184 A | 1/1997 | McDonnell et al. |
| 5,601,430 A | 2/1997 | Kutsch et al. |
| 5,620,414 A | 4/1997 | Campbell, Jr. |
| 5,643,299 A | 7/1997 | Bair |
| 5,660,817 A | 8/1997 | Masterman et al. |
| 5,674,226 A | 10/1997 | Doherty et al. |
| 5,720,894 A | 2/1998 | Neev et al. |
| 5,730,727 A | 3/1998 | Russo |
| 5,735,815 A | 4/1998 | Bair |
| 5,740,291 A | 4/1998 | De Lasa et al. |
| 5,755,752 A | 5/1998 | Segal |
| 5,759,159 A | 6/1998 | Masreliez |
| 5,795,153 A | 8/1998 | Rechmann |
| 5,797,745 A | 8/1998 | Ruddle |
| 5,810,037 A | 9/1998 | Sasaki et al. |
| 5,816,807 A | 10/1998 | Matsutani et al. |
| 5,820,373 A | 10/1998 | Okano et al. |
| 5,825,958 A | 10/1998 | Gollihar et al. |
| 5,839,896 A | 11/1998 | Hickok et al. |
| 5,842,863 A | 12/1998 | Bruns et al. |
| 5,846,080 A | 12/1998 | Schneider |
| 5,853,384 A | 12/1998 | Bair |
| 5,865,790 A | 2/1999 | Bair |
| 5,868,570 A | 2/1999 | Hickok et al. |
| 5,874,677 A | 2/1999 | Bab et al. |
| 5,879,160 A | 3/1999 | Ruddle |
| 5,915,965 A | 6/1999 | Ohlsson et al. |
| 5,921,775 A | 7/1999 | Buchanan |
| 5,968,039 A | 10/1999 | Deutsch |
| 5,975,897 A | 11/1999 | Propp et al. |
| 5,989,023 A | 11/1999 | Summer et al. |
| 6,004,319 A | 12/1999 | Goble et al. |
| 6,053,735 A | 4/2000 | Buchanan |
| 6,079,979 A | 6/2000 | Riitano |
| 6,122,300 A | 9/2000 | Freiberg et al. |
| 6,129,721 A | 10/2000 | Kataoka et al. |
| 6,139,319 A | 10/2000 | Sauer et al. |
| 6,143,011 A | 11/2000 | Hood et al. |
| 6,159,006 A | 12/2000 | Cook et al. |
| 6,162,052 A | 12/2000 | Kokubu |
| 6,162,177 A | 12/2000 | Bab et al. |
| 6,162,202 A | 12/2000 | Sicurelli et al. |
| 6,164,966 A | 12/2000 | Turdiu et al. |
| 6,179,617 B1 | 1/2001 | Ruddle |
| 6,190,318 B1 | 2/2001 | Bab et al. |
| 6,221,031 B1 | 4/2001 | Heraud |
| 6,224,378 B1 | 5/2001 | Valdes et al. |
| 6,227,855 B1 | 5/2001 | Hickok et al. |
| 6,245,032 B1 | 6/2001 | Sauer et al. |
| 6,282,013 B1 | 8/2001 | Ostler et al. |
| 6,288,499 B1 | 9/2001 | Rizoiu et al. |
| 6,290,502 B1 | 9/2001 | Hugo |
| 6,312,440 B1 | 11/2001 | Hood et al. |
| 6,315,557 B1 | 11/2001 | Messick |
| 6,343,929 B1 | 2/2002 | Fischer |
| 6,386,871 B1 | 5/2002 | Rossell |
| 6,390,815 B1 | 5/2002 | Pond |

(56) References Cited

U.S. PATENT DOCUMENTS

| | | | |
|---|---|---|---|
| 6,428,319 B1 | 8/2002 | Lopez et al. | |
| 6,440,103 B1 | 8/2002 | Hood et al. | |
| 6,454,566 B1 | 9/2002 | Lynch et al. | |
| 6,464,498 B1 | 10/2002 | Pond | |
| 6,485,304 B2 | 11/2002 | Beerstecher et al. | |
| 6,497,572 B2 | 12/2002 | Hood et al. | |
| 6,511,493 B1 | 1/2003 | Moutafis et al. | |
| 6,514,077 B1 | 2/2003 | Wilk | |
| 6,527,766 B1 | 3/2003 | Bair | |
| 6,538,739 B1 | 3/2003 | Visuri et al. | |
| 6,562,050 B1 | 5/2003 | Owen | |
| 6,572,709 B1 | 6/2003 | Kaneda et al. | |
| 6,602,074 B1 | 8/2003 | Suh et al. | |
| 6,616,447 B1 | 9/2003 | Rizoiu et al. | |
| 6,638,219 B1 | 10/2003 | Asch et al. | |
| 6,641,394 B2 | 11/2003 | Garman | |
| 6,663,386 B1 | 12/2003 | Moelsgaard | |
| 6,676,409 B2 | 1/2004 | Grant | |
| 6,783,364 B1 | 8/2004 | Juan | |
| 6,817,862 B2 | 11/2004 | Hickok | |
| 6,821,272 B2 | 11/2004 | Rizoiu et al. | |
| D499,486 S | 12/2004 | Kuhn et al. | |
| 6,881,061 B2* | 4/2005 | Fisher | A61C 17/20 |
| | | | 433/119 |
| 6,910,887 B2 | 6/2005 | Van Den Houdt | |
| 6,948,935 B2 | 9/2005 | Nusstein | |
| 6,971,878 B2 | 12/2005 | Pond | |
| 6,976,844 B2 | 12/2005 | Hickok et al. | |
| 6,981,869 B2 | 1/2006 | Ruddle | |
| 6,997,714 B1 | 2/2006 | Schoeffel | |
| 7,011,521 B2 | 3/2006 | Sierro et al. | |
| 7,011,644 B1 | 3/2006 | Andrew et al. | |
| 7,044,737 B2 | 5/2006 | Fu | |
| 7,108,693 B2 | 9/2006 | Rizoiu et al. | |
| 7,115,100 B2 | 10/2006 | McRury et al. | |
| 7,147,468 B2 | 12/2006 | Snyder et al. | |
| 7,163,400 B2 | 1/2007 | Cozean et al. | |
| 7,238,342 B2 | 7/2007 | Torabinejad et al. | |
| 7,261,561 B2 | 8/2007 | Ruddle et al. | |
| 7,269,306 B1 | 9/2007 | Koeneman et al. | |
| 7,270,544 B2 | 9/2007 | Schemmer et al. | |
| 7,288,086 B1 | 10/2007 | Andriasyan | |
| 7,296,318 B2 | 11/2007 | Mourad et al. | |
| 7,306,459 B1 | 12/2007 | Williams et al. | |
| 7,306,577 B2 | 12/2007 | Lemoine et al. | |
| 7,326,054 B2 | 2/2008 | Todd et al. | |
| 7,356,225 B2 | 4/2008 | Loebel | |
| 7,384,419 B2 | 6/2008 | Jones et al. | |
| 7,415,050 B2 | 8/2008 | Rizoiu et al. | |
| 7,421,186 B2 | 9/2008 | Boutoussov et al. | |
| 7,445,618 B2 | 11/2008 | Eggers et al. | |
| 7,470,124 B2 | 12/2008 | Bornstein | |
| 7,485,116 B2 | 2/2009 | Cao | |
| 7,549,861 B2 | 6/2009 | Ruddle et al. | |
| 7,620,290 B2 | 11/2009 | Rizoiu et al. | |
| 7,630,420 B2 | 12/2009 | Boutoussov | |
| 7,641,668 B2 | 1/2010 | Perry et al. | |
| 7,670,141 B2 | 3/2010 | Thomas et al. | |
| 7,695,469 B2 | 4/2010 | Boutoussov et al. | |
| 7,696,466 B2 | 4/2010 | Rizoiu et al. | |
| 7,702,196 B2 | 4/2010 | Boutoussov et al. | |
| 7,748,979 B2 | 7/2010 | Nahlieli | |
| 7,778,306 B2 | 8/2010 | Marincek et al. | |
| 7,815,630 B2 | 10/2010 | Rizoiu et al. | |
| 7,817,687 B2 | 10/2010 | Rizoiu et al. | |
| 7,833,016 B2 | 11/2010 | Gharib et al. | |
| 7,845,944 B2 | 12/2010 | DiGasbarro | |
| 7,867,224 B2 | 1/2011 | Lukac et al. | |
| 7,901,373 B2 | 3/2011 | Tavger | |
| 7,909,817 B2 | 3/2011 | Griffin et al. | |
| 7,916,282 B2 | 3/2011 | Duineveld et al. | |
| 7,959,441 B2 | 6/2011 | Glover et al. | |
| 7,970,027 B2 | 6/2011 | Rizoiu et al. | |
| 7,970,030 B2 | 6/2011 | Rizoiu et al. | |
| 7,980,854 B2 | 7/2011 | Glover et al. | |
| 7,980,923 B2 | 7/2011 | Olmo et al. | |
| 8,002,544 B2 | 8/2011 | Rizoiu et al. | |
| 8,011,923 B2 | 9/2011 | Lukac et al. | |
| 8,033,825 B2 | 10/2011 | Rizoiu et al. | |
| 8,047,841 B2 | 11/2011 | Jefferies | |
| 8,128,401 B2 | 3/2012 | Ruddle et al. | |
| 8,152,797 B2 | 4/2012 | Boutoussov et al. | |
| 8,204,612 B2 | 6/2012 | Feine et al. | |
| 8,295,025 B2* | 10/2012 | Edel | A61C 17/20 |
| | | | 361/157 |
| 8,298,215 B2 | 10/2012 | Zinn | |
| 8,317,514 B2 | 11/2012 | Weill | |
| 8,322,910 B2 | 12/2012 | Gansmuller et al. | |
| 8,328,552 B2 | 12/2012 | Ruddle | |
| 8,388,345 B2 | 3/2013 | Ruddle | |
| 8,419,719 B2 | 4/2013 | Rizoiu et al. | |
| 8,439,676 B2 | 5/2013 | Florman | |
| 8,506,293 B2 | 8/2013 | Pond | |
| 8,617,090 B2* | 12/2013 | Fougere | A61C 17/0211 |
| | | | 601/160 |
| D699,180 S | 2/2014 | Sweere et al. | |
| 8,672,678 B2 | 3/2014 | Gramann et al. | |
| 8,684,956 B2* | 4/2014 | McDonough | A61C 17/0211 |
| | | | 433/216 |
| 8,709,057 B2 | 4/2014 | Tettamanti et al. | |
| 8,740,957 B2 | 6/2014 | Masotti | |
| 8,747,005 B2 | 6/2014 | Kemp et al. | |
| 8,753,121 B2 | 6/2014 | Gharib et al. | |
| 8,758,010 B2 | 6/2014 | Yamanaka et al. | |
| 8,801,316 B1 | 8/2014 | Abedini | |
| 8,834,457 B2 | 9/2014 | Cao | |
| 8,977,085 B2 | 3/2015 | Walsh et al. | |
| D726,324 S | 4/2015 | Duncan et al. | |
| 9,022,959 B2* | 5/2015 | Fusi, II | A61C 17/0211 |
| | | | 601/162 |
| 9,022,961 B2 | 5/2015 | Fougere et al. | |
| 9,025,625 B2 | 5/2015 | Skrabelj et al. | |
| 9,050,157 B2 | 6/2015 | Boyd et al. | |
| 9,101,377 B2 | 8/2015 | Boutoussov et al. | |
| 9,186,222 B2 | 11/2015 | Marincek et al. | |
| D745,966 S | 12/2015 | Piorek et al. | |
| 9,216,073 B2* | 12/2015 | McDonough | A61C 17/0211 |
| 9,308,326 B2 | 4/2016 | Hunter et al. | |
| 9,333,060 B2 | 5/2016 | Hunter | |
| 9,341,184 B2 | 5/2016 | Dion et al. | |
| 9,572,632 B2 | 2/2017 | Lukac et al. | |
| 9,579,174 B2 | 2/2017 | Yamamoto et al. | |
| 9,610,125 B2 | 4/2017 | Kazic et al. | |
| 9,700,382 B2 | 7/2017 | Pond et al. | |
| 9,700,384 B2 | 7/2017 | Yamamoto et al. | |
| 2002/0012897 A1 | 1/2002 | Tingley et al. | |
| 2002/0072032 A1 | 6/2002 | Senn et al. | |
| 2002/0108614 A1 | 8/2002 | Schultz | |
| 2003/0096213 A1 | 5/2003 | Hickok et al. | |
| 2003/0121532 A1 | 7/2003 | Coughlin et al. | |
| 2003/0191429 A1 | 10/2003 | Andrew et al. | |
| 2003/0207231 A1 | 11/2003 | Nance | |
| 2003/0207232 A1 | 11/2003 | Todd et al. | |
| 2003/0236517 A1 | 12/2003 | Appling | |
| 2004/0048226 A1 | 3/2004 | Garman | |
| 2004/0063074 A1 | 4/2004 | Fisher | |
| 2004/0072122 A1 | 4/2004 | Hegemann | |
| 2004/0073374 A1 | 4/2004 | Lockhart et al. | |
| 2004/0101809 A1 | 5/2004 | Weiss et al. | |
| 2004/0126732 A1 | 7/2004 | Nusstein | |
| 2004/0127892 A1 | 7/2004 | Harris | |
| 2005/0064371 A1 | 3/2005 | Soukos et al. | |
| 2005/0096529 A1 | 5/2005 | Cooper et al. | |
| 2005/0136375 A1 | 6/2005 | Sicurelli, Jr. et al. | |
| 2005/0155622 A1 | 7/2005 | Leis | |
| 2005/0170312 A1 | 8/2005 | Pond | |
| 2005/0199261 A1 | 9/2005 | Vanhauwemeiren et al. | |
| 2005/0271531 A1 | 12/2005 | Brown et al. | |
| 2005/0277898 A1 | 12/2005 | Dimalanta et al. | |
| 2006/0019220 A1 | 1/2006 | Loebel et al. | |
| 2006/0021642 A1 | 2/2006 | Sliwa et al. | |
| 2006/0036172 A1 | 2/2006 | Abe | |
| 2006/0064037 A1 | 3/2006 | Shalon et al. | |
| 2006/0184071 A1 | 8/2006 | Klopotek | |

(56) References Cited

U.S. PATENT DOCUMENTS

| | | |
|---|---|---|
| 2006/0189965 A1 | 8/2006 | Litvak et al. |
| 2006/0234182 A1 | 10/2006 | Ruddle et al. |
| 2006/0234183 A1 | 10/2006 | Ruddle et al. |
| 2006/0246395 A1 | 11/2006 | Pond |
| 2006/0257819 A1 | 11/2006 | Johnson |
| 2006/0264808 A1 | 11/2006 | Staid et al. |
| 2007/0009449 A1 | 1/2007 | Kanca |
| 2007/0016177 A1 | 1/2007 | Vaynberg et al. |
| 2007/0016178 A1 | 1/2007 | Vaynberg et al. |
| 2007/0020576 A1 | 1/2007 | Osborn et al. |
| 2007/0042316 A1 | 2/2007 | Pichat et al. |
| 2007/0049911 A1 | 3/2007 | Brown |
| 2007/0072153 A1 | 3/2007 | Gross et al. |
| 2007/0083120 A1 | 4/2007 | Cain et al. |
| 2007/0148615 A1 | 6/2007 | Pond |
| 2007/0175502 A1 | 8/2007 | Sliwa |
| 2007/0179486 A1 | 8/2007 | Welch et al. |
| 2007/0265605 A1 | 11/2007 | Vaynberg et al. |
| 2007/0287125 A1 | 12/2007 | Weill |
| 2008/0014545 A1 | 1/2008 | Schippers |
| 2008/0032259 A1 | 2/2008 | Schoeffel |
| 2008/0044789 A1 | 2/2008 | Johnson |
| 2008/0050702 A1 | 2/2008 | Glover et al. |
| 2008/0070195 A1 | 3/2008 | DiVito et al. |
| 2008/0085490 A1 | 4/2008 | Jabri |
| 2008/0138761 A1 | 6/2008 | Pond |
| 2008/0155770 A1 | 7/2008 | Grez |
| 2008/0159345 A1 | 7/2008 | Bornstein |
| 2008/0160479 A1 | 7/2008 | Ruddle et al. |
| 2008/0160480 A1 | 7/2008 | Ruddle et al. |
| 2008/0188848 A1 | 8/2008 | Deutmeyer et al. |
| 2008/0199831 A1* | 8/2008 | Teichert .............. A61C 17/20 433/216 |
| 2008/0255498 A1 | 10/2008 | Houle |
| 2008/0285600 A1 | 11/2008 | Marincek et al. |
| 2008/0311540 A1 | 12/2008 | Gottenbos et al. |
| 2009/0004621 A1 | 1/2009 | Quan et al. |
| 2009/0011380 A1 | 1/2009 | Wang |
| 2009/0047624 A1 | 2/2009 | Tsai |
| 2009/0047634 A1 | 2/2009 | Calvert |
| 2009/0054881 A1 | 2/2009 | Krespi |
| 2009/0059994 A1 | 3/2009 | Nemes et al. |
| 2009/0111068 A1 | 4/2009 | Martinez |
| 2009/0111069 A1 | 4/2009 | Wagner |
| 2009/0130622 A1 | 5/2009 | Bollinger et al. |
| 2009/0208898 A1 | 8/2009 | Kaplan |
| 2009/0211042 A1* | 8/2009 | Bock .................. A46B 13/023 15/22.1 |
| 2009/0220908 A1 | 9/2009 | Divito et al. |
| 2009/0227185 A1 | 9/2009 | Summers et al. |
| 2009/0263759 A1 | 10/2009 | Van Herpern |
| 2010/0047734 A1 | 2/2010 | Harris et al. |
| 2010/0143861 A1 | 6/2010 | Gharib |
| 2010/0152634 A1 | 6/2010 | Dove |
| 2010/0160838 A1 | 6/2010 | Krespi |
| 2010/0209867 A1 | 8/2010 | Becker et al. |
| 2010/0229316 A1 | 9/2010 | Hohlbein et al. |
| 2010/0273125 A1 | 10/2010 | Janssen et al. |
| 2010/0330539 A1 | 12/2010 | Glover et al. |
| 2011/0027746 A1 | 2/2011 | McDonough et al. |
| 2011/0027747 A1 | 2/2011 | Fougere et al. |
| 2011/0072605 A1 | 3/2011 | Steur |
| 2011/0087605 A1 | 4/2011 | Pond |
| 2011/0111365 A1 | 5/2011 | Gharib et al. |
| 2011/0117517 A1 | 5/2011 | Bergheim et al. |
| 2011/0143310 A1 | 6/2011 | Hunter |
| 2011/0229845 A1 | 9/2011 | Chen |
| 2011/0256503 A1 | 10/2011 | Fraser |
| 2011/0269099 A1 | 11/2011 | Glover et al. |
| 2011/0270241 A1 | 11/2011 | Boutoussov |
| 2012/0135373 A1* | 5/2012 | Cheng ................ A61C 1/084 433/75 |
| 2012/0141953 A1 | 6/2012 | Mueller |
| 2012/0237893 A1 | 9/2012 | Bergheim |
| 2012/0276497 A1 | 11/2012 | Gharib |
| 2012/0282570 A1 | 11/2012 | Mueller |
| 2012/0021375 A1 | 12/2012 | Binner et al. |
| 2013/0040267 A1 | 2/2013 | Bergheim |
| 2013/0084544 A1 | 4/2013 | Boutoussov et al. |
| 2013/0084545 A1 | 4/2013 | Netchitailo et al. |
| 2013/0085486 A1 | 4/2013 | Boutoussov et al. |
| 2013/0131656 A1 | 5/2013 | Marincek et al. |
| 2013/0143180 A1 | 6/2013 | Glover et al. |
| 2013/0177865 A1 | 7/2013 | Ostler |
| 2013/0190738 A1 | 7/2013 | Lukac et al. |
| 2013/0216980 A1* | 8/2013 | Boronkay ............. A61C 9/002 433/213 |
| 2013/0236857 A1 | 9/2013 | Boutoussov et al. |
| 2013/0288195 A1 | 10/2013 | Mueller |
| 2013/0296910 A1 | 11/2013 | Deng |
| 2013/0330684 A1 | 12/2013 | Dillon et al. |
| 2013/0337404 A1 | 12/2013 | Feine |
| 2014/0032183 A1* | 1/2014 | Fisker ................ A61C 13/0004 703/1 |
| 2014/0072931 A1* | 3/2014 | Fougere ............. A61C 17/0211 433/80 |
| 2014/0080090 A1 | 3/2014 | Laufer |
| 2014/0087333 A1 | 3/2014 | DiVito et al. |
| 2014/0099597 A1 | 4/2014 | Bergheim |
| 2014/0113243 A1 | 4/2014 | Boutoussov et al. |
| 2014/0124969 A1* | 5/2014 | Blaisdell ............. A61C 8/0001 264/19 |
| 2014/0127641 A1 | 5/2014 | Hilscher et al. |
| 2014/0170588 A1 | 6/2014 | Miller et al. |
| 2014/0205965 A1 | 7/2014 | Boutoussov et al. |
| 2014/0220505 A1 | 8/2014 | Khakpour |
| 2014/0220511 A1 | 8/2014 | DiVito et al. |
| 2014/0242551 A1 | 8/2014 | Downs |
| 2014/0261534 A1 | 9/2014 | Schepis |
| 2014/0272782 A1 | 9/2014 | Luettgen et al. |
| 2014/0349246 A1 | 11/2014 | Johnson et al. |
| 2015/0010878 A1 | 1/2015 | Seibel et al. |
| 2015/0010882 A1 | 1/2015 | Bergheim |
| 2015/0017599 A1 | 1/2015 | Marincek et al. |
| 2015/0044631 A1 | 2/2015 | Lifshitz et al. |
| 2015/0044632 A1 | 2/2015 | Bergheim et al. |
| 2015/0056567 A1 | 2/2015 | Fregoso et al. |
| 2015/0056570 A1 | 2/2015 | Kansal |
| 2015/0125811 A1 | 5/2015 | Lifshitz et al. |
| 2015/0132712 A1 | 5/2015 | Gharib |
| 2015/0140503 A1 | 5/2015 | Bergheim et al. |
| 2015/0147715 A1* | 5/2015 | Breysse ............. A61C 8/0089 433/75 |
| 2015/0147717 A1 | 5/2015 | Taylor et al. |
| 2015/0147718 A1 | 5/2015 | Khakpour |
| 2015/0150650 A1 | 6/2015 | Netchitailo et al. |
| 2015/0173850 A1 | 6/2015 | Garrigues et al. |
| 2015/0173852 A1 | 6/2015 | Khakpour |
| 2015/0190597 A1 | 7/2015 | Zachar et al. |
| 2015/0216597 A1 | 8/2015 | Boutoussov et al. |
| 2015/0230865 A1 | 8/2015 | Sivriver et al. |
| 2015/0268803 A1 | 9/2015 | Patton et al. |
| 2015/0277738 A1 | 10/2015 | Boutoussov et al. |
| 2015/0283277 A1 | 10/2015 | Schafer et al. |
| 2015/0327964 A1 | 11/2015 | Bock |
| 2015/0335410 A1* | 11/2015 | Zhao .................. A61C 17/20 433/86 |
| 2015/0366634 A1 | 12/2015 | Gharib |
| 2015/0367142 A1 | 12/2015 | Kazic et al. |
| 2015/0374471 A1 | 12/2015 | Stangel et al. |
| 2016/0022392 A1 | 1/2016 | Chang et al. |
| 2016/0095679 A1 | 4/2016 | Khakpour |
| 2016/0100921 A1 | 4/2016 | Ungar |
| 2016/0113733 A1 | 4/2016 | Pond et al. |
| 2016/0128815 A1 | 5/2016 | Birdee et al. |
| 2016/0135581 A1 | 5/2016 | Pai |
| 2016/0149370 A1 | 5/2016 | Marincek et al. |
| 2016/0149372 A1 | 5/2016 | Marincek et al. |
| 2016/0324600 A1 | 11/2016 | Gharib |
| 2016/0367346 A1 | 12/2016 | Gharib |
| 2017/0036253 A1 | 2/2017 | Lukac et al. |
| 2017/0056143 A1 | 3/2017 | Hyun |

(56) References Cited

U.S. PATENT DOCUMENTS

2017/0196658 A1   7/2017  Schoeffel
2017/0216579 A1   8/2017  Becker et al.

FOREIGN PATENT DOCUMENTS

| | | |
|---|---|---|
| AU | 2011316839 | 8/2015 |
| CN | 102724929 | 10/2012 |
| CN | 103027762 A | 4/2013 |
| CN | 103347462 | 10/2013 |
| CN | 104470464 A | 3/2015 |
| DE | 37 08 801 A1 | 9/1988 |
| DE | 102 48 336 | 5/2004 |
| DE | 103 31 583 | 7/2004 |
| EP | 1 214 916 | 6/2002 |
| EP | 0 902 654 | 8/2004 |
| EP | 2 498 713 | 9/2012 |
| EP | 2 821 027 | 1/2015 |
| EP | 2 836 156 | 2/2015 |
| EP | 2 836 157 | 2/2015 |
| EP | 2 934 364 | 10/2015 |
| EP | 2 951 019 | 12/2015 |
| EP | 3 013 277 | 5/2016 |
| FR | 1 225 547 | 7/1960 |
| FR | 2 831 050 | 10/2001 |
| GB | 917 633 | 2/1963 |
| HK | 1 188 108 A | 4/2014 |
| IL | 219169 | 4/2013 |
| JP | 09-276292 | 10/1997 |
| JP | 11-113927 A | 4/1999 |
| JP | 11-244303 A | 9/1999 |
| JP | 2000-254153 A | 9/2000 |
| JP | 2002-209911 | 7/2002 |
| JP | 2004-313659 | 11/2003 |
| JP | 3535685 B2 | 6/2004 |
| JP | 2004-267756 | 9/2004 |
| JP | 2005-095374 | 4/2005 |
| JP | 2007-533333 | 11/2007 |
| JP | 2008-93080 | 4/2008 |
| JP | 2008-132099 | 6/2008 |
| JP | 2009-114953 | 5/2009 |
| JP | 2013-510688 | 3/2013 |
| JP | 2013-544120 | 12/2013 |
| JP | 2015-510829 | 4/2015 |
| KR | 10-2008-0105713 A | 12/2008 |
| KR | 10-2012-0084897 A | 7/2012 |
| KR | 10-2013-0141103 A | 12/2013 |
| KR | 2004-72508 Y1 | 5/2014 |
| RU | 2326611 C1 | 12/2011 |
| WO | WO 1992/004871 | 4/1992 |
| WO | WO 1992/12685 | 8/1992 |
| WO | WO 1998/025536 | 6/1995 |
| WO | WO 1996/12447 | 5/1996 |
| WO | WO 2000/045731 | 8/2000 |
| WO | WO 2001/93773 | 12/2001 |
| WO | WO 2002/078644 | 10/2002 |
| WO | WO 2003/086223 | 10/2003 |
| WO | WO 2004/034923 | 4/2004 |
| WO | WO 2004/082501 | 9/2004 |
| WO | WO 2005/007008 | 1/2005 |
| WO | WO 2005/032393 | 4/2005 |
| WO | WO 2006/082101 | 8/2006 |
| WO | WO 2007/007335 | 1/2007 |
| WO | WO 2007/007336 | 1/2007 |
| WO | WO 2007/124038 | 11/2007 |
| WO | WO 2008/024442 | 2/2008 |
| WO | WO 2008/092125 | 7/2008 |
| WO | WO 2008/120018 | 10/2008 |
| WO | WO 2009/047670 | 4/2009 |
| WO | WO 2009/064947 | 5/2009 |
| WO | WO 2009/137815 | 11/2009 |
| WO | WO 2010/099538 | 9/2010 |
| WO | WO 2011/060327 | 5/2011 |
| WO | WO 2011/077291 | 6/2011 |
| WO | WO 2012/054905 | 4/2012 |
| WO | WO 2012/074918 | 6/2012 |
| WO | WO 2013/15700 | 1/2013 |
| WO | WO 2013/061251 | 5/2013 |
| WO | WO 2013/142385 | 9/2013 |
| WO | WO 2013/155492 | 10/2013 |
| WO | WO 2013/160888 | 10/2013 |
| WO | WO 2014/100751 | 6/2014 |
| WO | WO 2014/121293 | 8/2014 |
| WO | WO 2015/168329 | 11/2015 |
| WO | WO 2016/005221 | 1/2016 |

OTHER PUBLICATIONS

European Extended Search Report, re EP Application No. 13775073.3, dated Nov. 3, 2015.
International Preliminary Report on Patentability, re PCT Application No. PCT/US2014/036451, dated Nov. 3, 2015, 2015, in 11 pages.
Adachi et al; Jet Structure Analyses on High-Speed Submerged Water Jets through Cavitation 110 Noises; pp. 568-574; The Japan Society of Mechanical Engineers International Journal—Series B, vol. 39, No. 3; Nov. 1996.
Al-Jadaa et al; Acoustic Hypochlorite Activation in Simulated Curved Canals; pp. 1408-1411; Journal of Endodontics, vol. 35, No. 10; Oct. 2009.
Anand et al; Prevention of Nozzle Wear in High-Speed Slurry Jets Using Porous Lubricated Nozzles; pp. 1-13; Department of Mechanical Engineering, The Johns Hopkins University, Oct. 2000.
Anantharamaiah et al; A simple expression for predicting the inlet roundness of micro-nozzles; pp. N31-N39; Journal of Micromechanics and Microengineering, vol. 17; Mar. 21, 2007.
Anantharamaiah et al; A study on flow through hydroentangling nozzles and their degradation; pp. 4582-4594; Chemical Engineering Science, vol. 61; May 2006.
Anantharamaiah et al; Numerical Simulation of the Formation of Constricted Waterjets in Hydroentangling Nozzles Effects of Nozzle Geometry; pp. 31-238; Chemical Engineering Research and Design, vol. 84; Mar. 2006.
Attin et al; Clinical evaluation of the cleansing properties of the nonistrumental technique for cleaning root canals; pp. 929-933; International Endodontic Journal, vol. 35, Issue 11; Nov. 2002.
Batchelor et al; Analysis of the stability of axisymmetric jets; pp. 529-551; Journal of Fluid Mechanics, vol. 14; Dec. 1962.
Begenir et al; Effect of Nozzle Geometry on Hydroentangling Water Jets: Experimental Observations; pp. 178-184; Textile Research Journal, vol. 74; Feb. 2004.
Begenir, Asli; The Role of Orifice Design in Hydroentanglement; Thesis submitted to North Carolina State University; dated Dec. 2002, in 107 pages.
Borkent et al; Is there gas entrapped on submerged silicon wafers? Visualizing nano-scale bubbles with cavitation; pp. 225-228; Solid State Phenomena, vol. 134 (2008); available online Nov. 2007.
Bremond et al; Cavitation on surfaces; pp. S3603-S3608; Journal of Physics: Condensed Matter, vol. 17; Oct. 28, 2005.
Brennen, Christopher E.; Fission of collapsing cavitation bubbles; pp. 153-166; Journal of Fluid Mechanics, vol. 472; Dec. 2002.
Chang et al; Effects of Inlet Surface Roughness, Texture, and Nozzle Material on Cavitation; pp. 299-317; Atomization and Sprays, vol. 16 (2006).
Culjat et al., "B-Scan Imaging of Human Teeth Using Ultrasound," Apr. 2003, in 4 pages.
Didenkulov et al; Nonlinear Acoustic Diagnostics of Scatterer Spatial Distribution in a Cavitation Jet; Nov. 19-23, 2001, pp. 276-278, XI Session of the Russion Acoustical Society.
Dumouchel, Christophe; On the experimental investigation on primary atomization of liquid streams; pp. 371-422; Experimental Fluids, vol. 45; Jun. 22, 2008.
Eddingfield et al; Mathematical Modeling of High Velocity Water Jets; pp. 25-39; Proceedings of 1st U.S. Water Jet Conference; 1981.
EMS Electro Medical Systems, "Cleaning", in 2 pages, dated 2005, downloaded from http://www.ems-dent.com/en/endodontics cleaning.htm.

(56) References Cited

OTHER PUBLICATIONS

ESI Endo Soft Instruments, EMS Electro Medical Systems, Brochure in 2 pages, downloaded from www.emsdent.com, dated Jan. 2004.
European Extended Search Report re EP Application No. 09743801.4, dated Jun. 4, 2012.
European Extended Search Report re EP Application No. 14187012.1, dated Mar. 3, 2015, in 10 pages.
European Extended Search Report, dated Sep. 22, 2011, for EP Application No. 07755777.5, in 7 pages.
European Extended Search Report, re EP Application No. 08728345.3, dated Mar. 3, 2014.
Feng et al; Enhancement of ultrasonic cavitation yield by multi-frequency sonication; pp. 231-236; Ultrasonics Sonochemistry, vol. 9; Oct. 2002.
Flint, E. B., et al., "The Temperature of Cavitation", Science, vol. 253, Sep. 20, 1991, pp. 1397-1399.
Foldyna et al; Acoustic wave propagation in high-pressure system; pp. e1457-e1460; Ultrasonics vol. 44 (Supplement 1); Jun. 8, 2006.
Fuchs, "Ultrasonic Cleaning: Fundamental Theory and Application," Blackstone-Ney Ultrasonics, Jamestown, NY, May 2002.
G.E. Reisman and C.E. Brennen, "Pressure Pulses Generated by Cloud Cavitation", FED—vol. 236, 1996 Fluids Engineering Division Conference, vol. 1, pp. 319-328, ASME 1996.
G.E. Reisman, Y.-C. Wang and C.E. Brennen, "Observations of shock waves in cloud cavitation", J. Fluid Mech. (1998), vol. 355, pp. 255-283.
Ghassemieh et al; Effect of Nozzle Geometry on the Flow Characteristics of Hydroentangling Jets; pp. 444-450; Textile Research Journal, vol. 73; May 2003.
Ghassemieh et al; The effect of nozzle geometry on the flow characteristics of small water jets; pp. 1739-1753; Proceedings of the Institute of Mechanical Engineers, Part C: Mechanical Engineering Science, vol. 12, Sep. 2006.
Hahn et al; Acoustic resonances in the bubble plume formed by a plunging water jet; pp. 1751-1782; Proceedings of the Royal Society of London A, vol. 459; May 16, 2003.
Hashish, Mohamed; Experimental Studies of Cutting with Abrasive Waterjets; pp. 402-416; Proceedings of 2nd American Water Jet Conference; 1983.
Herbert et al; Cavitation pressure in water; pp. 041603-1 to 041603-22; Physical Review E, vol. 74; Oct. 2006.
Hiroyasu, Hiro; Spray Breakup Mechanism from the Hole-Type Nozzle and its Applications; pp. 511-527; Atomization and Sprays, vol. 10 (2000).
Hmud R. et al. "Cavitational Effects in Aqueous Endodontic Irrigants Generated by Near-Infrared Lasers", Journal of Endodontics, vol. 36, Issue 2, Feb. 2010, available online Dec. 4, 2009, in 4 pages.
Hoque et al; Air entrainment and associated energy dissipation in steady and unsteady plunging jets at free surface; pp. 37-45; Applied Ocean Research, vol. 30; May 2008.
Hydrocision Products: SpineJet Hydrosurgery; system webpage in 2 pages, copyright 2010, downloaded from http://www.hydrocision.com on Apr. 22, 2010.
Hydrocision SpineJet XL HydroSurgery System; Brochure in 2 pages, copyright 2004-2006, downloaded from http://www.hydrocision.com on Apr. 22, 2010.
International Preliminary Report and Written Opinion dated Nov. 9, 2010 for International Appl. No. PCT/US09/43386, in 6 pages.
International Preliminary Report on Patentability and Written Opinion, dated Oct. 14, 2014, re PCT Application No. PCT/US2013/036493, in 14 pages.
International Preliminary Report on Patentability dated Aug. 6, 2009, for International Appl. No. PCT/US08/52122, in 13 pages.
International Preliminary Report on Patentability dated Oct. 30, 2008, for International Appl. No. PCT/US07/09633, in 5 pages.
International Preliminary Report on Patentability re App. No. PCT/US2010/056620, dated May 15, 2012, in 10 pages.
International Preliminary Report on Patentability re PCT Application No. PCT/US2014/014732, dated Aug. 4, 2015.
International Preliminary Report on Patentability, re PCT Application No. PCT/US11/57401, dated Jan. 25, 2013 in 13 pages.
International Preliminary Report on Patentability, re PCT Application No. PCT/US2013/077286, dated Jun. 23, 2015.
International Search Report and Written Opinion dated Apr. 11, 2008, for International Appl. No. PCT/US07/09633, in 8 pages.
International Search Report and Written Opinion dated Aug. 8, 2008, for International Appl. No. PCT/US08/52122, in 18 pages.
International Search Report and Written Opinion dated Jul. 29, 2009, for International Appl. No. PCT/US09/43386, in 8 pages.
International Search Report and Written Opinion from International Application No. PCT/US2011/057401, dated Jan. 30, 2012, in 20 pages.
International Search Report and Written Opinion dated Jun. 28, 2013, re PCT Application No. PCT/US2013/036493, in 21 pages.
International Search Report and Written Opinion re App. No. PCT/US2010/056620, dated Jan. 12, 2011, in 17 pages.
International Search Report and Written Opinion re App. No. PCT/US2014/014732, dated Jul. 18, 2014.
International Search Report and Written Opinion, re PCT Application No. PCT/US 13/32635, dated Jun. 17, 2013 in 14 pages.
International Search Report and Written Opinion, re PCT Application No. PCT/US2013/077286, dated May 27, 2014.
International Search Report and Written Opinion, re PCT Application No. PCT/US2014/044186, dated Jan. 21, 2015, in 19 pages.
International Search Report and Written Opinion, re PCT Application No. PCT/US2015/028360, dated Sep. 28, 2015, in 24 pages.
Jackson et al; Nozzle Design for Coherent Water Jet Production; pp. 53-89; Proceeding of the 2nd US Water Jet Conference; May 1983.
Junge et al; Cell Detachment Method Using Shock-Wave-Induced Cavitation; pp. 1769-1776; Ultrasound in Medicine & Biology, vol. 29, No. 12; Dec. 2003.
Kalumuck et al; Development of High Erosivity Well Scale Cleaning Tools; pp. 1-36; Dynaflow, Inc.; Report 98012 conducted under Contract No. DE-FG07-981013684 for the US Dept. of Energy; Jul. 1999, in 36 pages.
Karasawa et al; Effect of Nozzle Configuration on the Atomization of a Steady Spray; pp. 411-426; Atomization and Sprays, vol. 2 (1992).
Kato, Hiroharu; Utilization of Cavitation for Environmental Protection—Killing Planktons and Dispersing Spilled Oil; pp. 1-8; In CAV2001: Fourth International Symposium on Caviation; California Institute of Technology, Pasadena, CA; dated Jun. 2001.
Lee et al; The efficacy of ultrasonic irrigation to remove artificially placed dentine debris from different-sized simulated plastic root canals; pp. 607-612; International Endodontic Journal, vol. 37; May 2004.
Li et al; Cavitation Resonance; pp. 031302-1 to 031302-7; Journal of Fluids Engineering, vol. 130; Mar. 2008.
Lienhard V et al; Velocity Coefficients for Free Jets From Sharp-Edged Orifices; pp. 13-17; Reprinted from Mar. 1984, vol. 106, Journal of Fluids Engineering.
Lin et al; Drop and Spray Formation from a Liquid Jet; pp. 85-105; Jan. 1998: vol. 30; Annual Review of Fluid Mechanics.
Linfield, Kevin William; A Study of the Discharge Coefficient of Jets From Angled Slots and Conical Orifices; Thesis submitted to Dept. of Aerospace Science and Engineering; University of Toronto; dated 2000; in 148 pages.
Lussi et al; A new non-instrumental technique for cleaning and filling root canals; pp. 1-6; International Endodontic Journal, vol. 28; Jan. 1995.
Lussi et al; A Novel Noninstrumented Technique for Cleansing the Root Canal System; pp. 549-553; Journal of Endodontics, vol. 19, No. 11; Nov. 1993.
Lussi et al; In vivo performance of the new non-instrumentation technology (NIT) for root canal obturation; pp. 352-358; International Endodontic Journal, vol. 35; Apr. 2002.
Maximum Dental Inc., "Canal Clean Max", "Intra Canal Irrigation and Aspiration Device", and "SonicMax, Endo-Perio Sonic Handpiece", in 3 pages, downloaded from www.dentalmaximum.com on May 8, 2008.
Ohrn et al; Geometric Effects on Spray Cone Angle for Plain-Orifice Atomizers; pp. 253-268; Atomization and Sprays, vol. 1 (1991).

(56) References Cited

OTHER PUBLICATIONS

Ohrn et al; Geometrical Effects on Discharge Coefficients for Plain-Orifice Atomizers; pp. 137-153; Atomization and Sprays, vol. 1, No. 2 (1991).
Phinney, Ralph E.; The breakup of a turbulent liquid jet in a gaseous atmosphere; pp. 689-701; J. Fluid Mechanics, vol. 60, Part 4; Oct. 1973.
Piezon Master 600 Ultrasound a la carte, EMS Electro Medical Systems, EMS SA FA-319.EN ed. Mar. 2009; Brochure dated Mar. 2009, in 2 pages.
Quinn, W. R.; Experimental study of the near field and transition region of a free jet issuing from a sharp-edged elliptic orifice plate; pp. 583-614; European Journal of Mechanics—B/Fluids, vol. 26; Jul.-Aug. 2007; available online Dec. 2006.
Ramamurthi et al; Disintegration of Liquid Jets from Sharp-Edged Nozzles; pp. 551-564; Atomization and Sprays, vol. 4 (1994).
Reitz et al; Mechanism of atomization of a liquid jet; pp. 1730-1742; Physics Fluids, vol. 25, No. 10; Oct. 1982.
Sabeti, "Healing of apical periodontitis after endodontic treatment with and without obturation in dogs," Journal of Endodontics, Jul. 2006, pp. 628-633.
Sallam et al; Liquid breakup at the surface of turbulent round liquid jets in still gases; pp. 427-449; International Journal of Multiphase Flow, vol. 28; Mar. 2002.
Sawant et al; Effect of hydrodynamic cavitation on zooplankton: A tool for disinfection; pp. 320-328; Biochemical Engineering Journal, vol. 42, Issue 3; Dec. 2008.
Shi et al; Comparison-speed liquid jets; Experiments in Fluids, vol. 35; pp. 486-492; Oct. 7, 2003.
Sou et al; Effects of cavitation in a nozzle on liquid jet atomization; pp. 3575-3582; International Journal of Heat and Mass Transfer, vol. 50; Mar. 2007.
Soyama et al; High-Speed Observation of Ultrahigh-Speed Submerged Water Jets; pp. 411-416; Experimental Thermal and Fluid Science, vol. 12 1996).
Soyama, Hitoshi; High-Speed Observation of a Cavitating Jet in Air; Journal of Fluids Engineering, vol. 127; pp. 1095-1101; Nov. 2005.
Summers, David A; Considerations in the Comparison of Cavitating and Plain Water Jets; pp. 178-184; Rock Mechanics and Explosive Research Center, Rolla, Missouri, 1983.
Summers, David A; The Volume Factor in Cavitation Erosion; Proceedings of 6th International Conference on Erosion by Liquid and Solid Impact; University of Missouri-Rolla; Rolla, Missouri, 1983, in 12 pages.
Suslick, K. S., et al., "The Sonochemical Hot Spot", Journal of the American Chemical Society, vol. 108, No. 18, Sep. 3, 1986, pp. 5641-5642.
Suslick, K. S., et al., "Heterogeneous Sonocatalysis with Nickel Powder", Journal of the American Chemical Society, vol. 109, No. 11, May 27, 1987, pp. 3459-3461.
Tafreshi et al; Simulating Cavitation and Hydraulic Flip Inside Hydroentangling Nozzles; pp. 359-364; Textile Research Journal, vol. 74, Apr. 2004.
Tafreshi et al; Simulating the Flow Dynamics in Hydroentangling Nozzles: Effect of Cone Angle and Nozzle Aspect Ratio; pp. 700-704; Textile Research Journal, vol. 73; Aug. 2003.
Tafreshi et al; The effects of nozzle geometry on waterjet breakup at high Reynolds numbers; pp. 364-371; Experiments in Fluids, vol. 35; Sep. 2, 2003.
Zuo et al; An Attribution of Cavitation Resonance: Volumetric Oscillations of Cloud; pp. 152-158; Journal of Hydrodynamics, vol. 21; Apr. 2009.
U.S. Appl. No. 61/701,947, filed Sep. 17, 2012, Laufer.
U.S. Appl. No. 61/894,762, filed Oct. 23, 2013, Lifshitz et al.
U.S. Appl. No. 61/895,316, filed Oct. 24, 2013, Lifshitz et al.
Ebihara et al.: "Er:YAG laser modification of root canal dentine: Influence of pulse duration, repetitive irradiation and water spray," Lasers in Medical Science, 17(3), 198-207, Aug. 2002.

Nammour et al.: "External temperature during KTP-nd:YAG laser irradiation in root canals: An in vitro study," Lasers in Medical Science, 19(1), 27-32, Jul. 2004.
Ulrich Schoop et al.: "The use of the erbium, chromium:yttrium-scandium-gallium-garnet laser in endodontic treatment: The results of an in vitro study," The Journal of the American Dental Association: vol. 138, Issue 7, Jul. 2007, pp. 949-955.
Wohlemuth et al.: "Effectiveness of GentleWave System in Removing Separated Instruments," JOE, vol. 41, No. 11, Nov. 2015.
ADA American Dental Association, "Glossary of Dental Clinical and Administrative Terms," http://www.ada.org/en/publications/cdt/glossary-of-dental-clinical-and-administrative-ter, downloaded May 4, 2017, in 46 pages.
Alomairy, Evaluating two techniques on removal of fractured rotary nickel-titanium endodontic instruments from root canals: an in vitro study. J Endod 2009;35:559-62.
U.S. Appl. No. 15/478,039, filed Apr. 3, 2017, Khakpour et al.
Bahia, et al.: Physical and mechanical characterization and the influence of cyclic loading on the behaviour of nickel-titanium wires employed in the manufacture of rotary endodontic instruments. Int Endod. J. 2005;38:795-801.
Charara, et al.: "Assessment of apical extrusion during root canal procedure with the novel GentleWave system in a simulated apical environment," J Endod 2015. In Press.
Crump et al., "Relationship of broken root canal instruments to endodontic case prognosis: a clinical investigation," J Am Dent Assoc 1970;80:1341-7.
D'Arcangelo, et al.: "Broken instrument removal—two cases," J Endod 2000;26:368-70.
Esen, et al.: "Apical microleakage of root-end cavities prepared by CO2 laser," J Endod 2004;30:662-4.
European Extended Search Report, re EP Application No. 13763534. 8, dated Aug. 11, 2017.
European Exam Report, re EP Application No. 13775073.3, dated Jun. 28, 2017.
Feldman, et al.: "Retrieving broken endodontic instruments," J Am Dent Assoc. 1974:88:588-91.
Fors, et al.: "A method for the removal of broken endodontic instruments from root canals," J Endod 1983;9:156-9.
Gencoglu, et al.: Comparison of the different techniques to remove fractured endodontic instruments from root canal systems. Eur J Dent 2009;3:90-5.
Haapasalo, et al.: "Tissue dissolution by a novel multisonic ultracleaning system and sodium hypochlorite," J Endod 2014;40:1178-81.
Haikel, et al.: Dynamic and cyclic fatigue of engine-driven rotary nickel-titanium endodontic instruments. J Endod 1999;25:434-40.
Haikel, et al.: Dynamic fracture of hybrid endodontic hand instruments compared with traditional files. J Endod 1991;17:217-20.
Hulsmann, et al.: Influence of several factors on the success or failure of removal of fractured instruments from the root canal. Endod Dent Traumatol 199;15:252-8.
Hulsmann: "Methods for removing metal obstructions from the root canal," Endod Dent Traumatol 1993;9:223-37.
Iqbal, et al.: "A comparison of three methods for preparing centered platforms around separated instruments in curved canals," J Endod 2006;32:48-51.
Lukac et al.: "Photoacoustic Endodontics Using the Novel SWEEPS Er:YAG Laser Modality," Journal of the Laser and Health Academy, vol. 2017, No. 1; www.laserlaserandhealth.com.
Ma, et al.: "In vitro study of calcium hydroxide removal from mandibular molar root canals," J Endod 2015;41:553-8.
Madarati, et al.: "Efficiency of a newly designed ultrasonic unit and tips in reducing temperature rise on root surface during the removal of fractured files," J Endod 2009;35:896-9.
Madarati, et al.: "Management of intracanal separated instruments," J Endod 2013;39:569-81.
Madarati, et al.: "Qualtrough AJ. Factors contributing to the separation of endodontic files," Br Dent J 2008;204:241-5.
Molina, et al.: "Histological evaluation of root canal debridement of human molars using the GentleWaveTM system," J Endod 2015;41:1702-5.

(56) References Cited

OTHER PUBLICATIONS

Nevares, et al.: "Success rates for removing or bypassing fractured instruments: a prospective clinical study," J Endod 2012;38:442-4.

Roth, et al.: "A study of the strength of endodonitc files: potential for torsional breakage and relative flexibility," J Endod 1983; 9:228-32.

Ruddle, "Nonsurgical retreatment," J Endod 2004;30:827-45.

Schneider, et al.: "A comparison of canal preparations in straight and curved root canals," Oral Surg Oral Med Oral Pathol 1971;32:271-5.

Schneider, et al.: "NIH Image to ImageJ: 25 years of image analysis," Nat Methods 2012;9:671-5.

Shen, et al.: "Factors associated with the removal of fractured NiTi instruments from root canal systems," Oral Surg Oral Med Oral Pathol Oral Radiol Endod 2004;98:605-10.

Skyttner, "Endodontic instrument separations: evaluation of a patient cases series with separated endodontic instruments and factors related to the treatment regarding separated instruments [thesis]," Stockholm: Karolinska Institutet; 2007.

Souter, et al.: "Complications associated with fractured file removal using an ultrasonic technique," J Endod 2005;31:450-2.

Suter, et al.: "Probability of removing fractured instruments from root canals," Int Endod J 2005;38:112-23.

Terauchi, et al.: "Evaluation of the efficiency of a new file removal system in comparison with two conventional systems," J. Endod 2007;33:585-8.

Ward Jr.: "The use of an ultrasonic technique to remove a fractured rotary nickel-titanium instrument from the apical third of a curved root canal," Aust Endod J 2003;29:25-30.

Yoldas, et al.: "Perforation risks associated with the use of Masserann endodontic kit drills in mandibular molars," Oral Surg Oral Med Oral Pathol Oral Radiol Endod 2004;97:513-7.

Yu et al.: "Study on removal effects of filling materials and broken files from root canals using pulsed Nd:YAG laser," J Clin Laser Med Surg 2000;18:23-8.

* cited by examiner

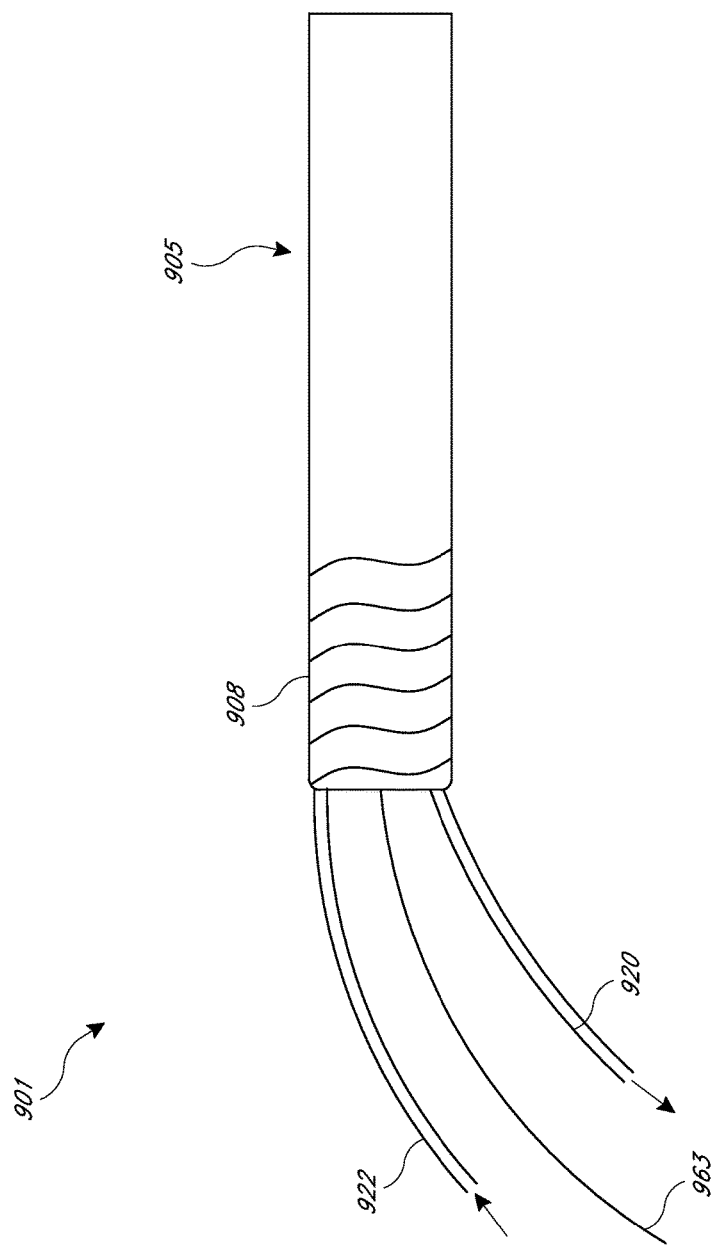

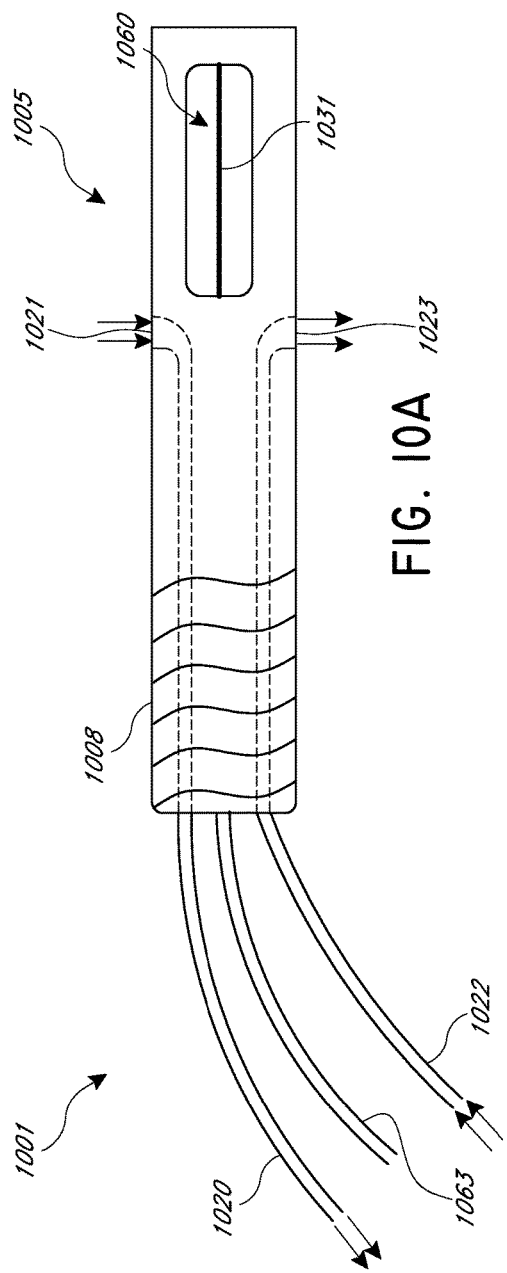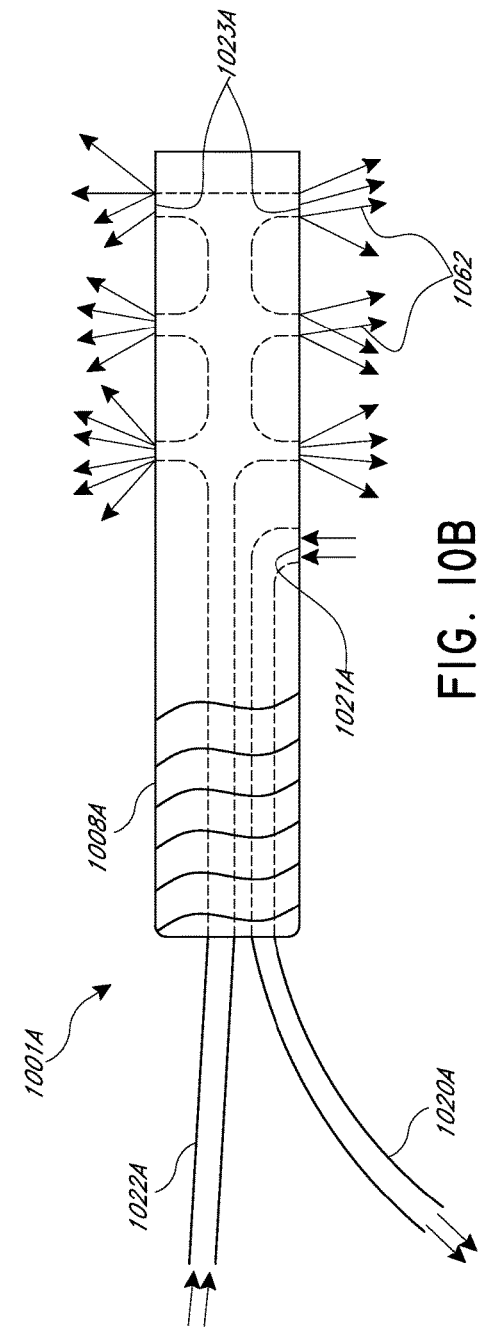

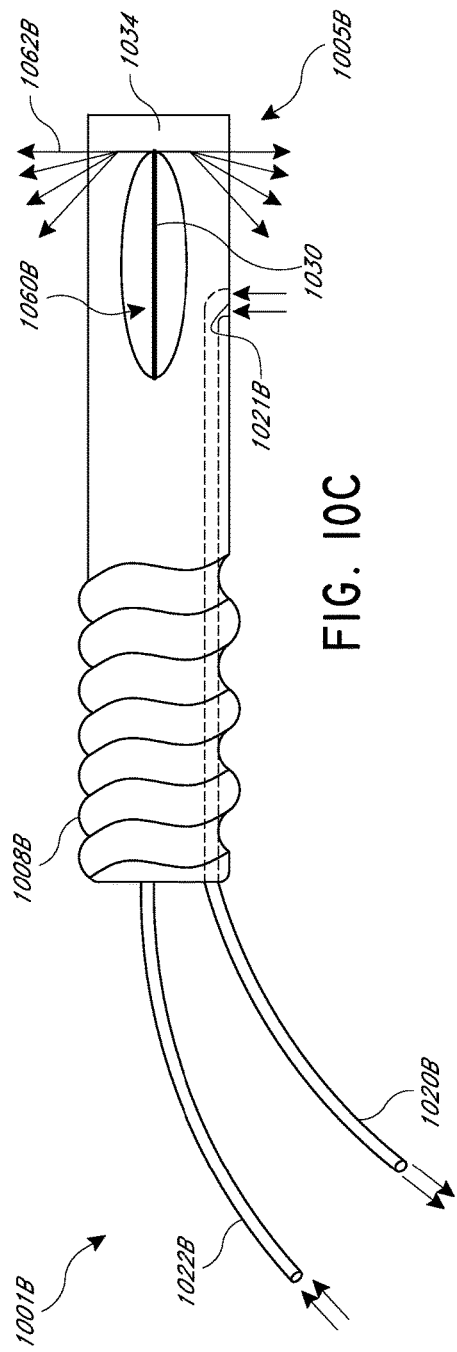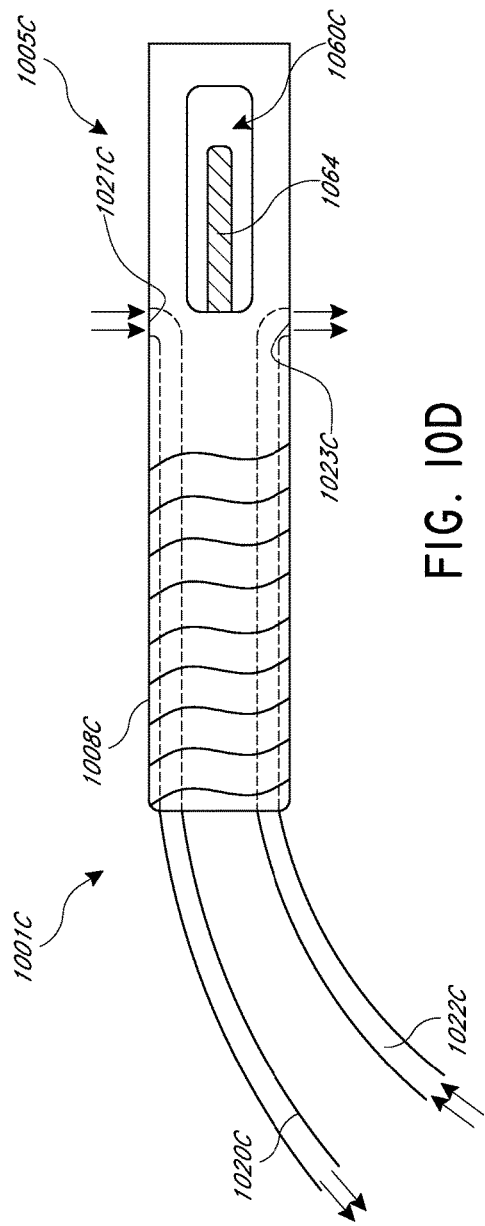
FIG. 10C
FIG. 10D

APPARATUS AND METHODS FOR CLEANING TEETH AND GINGIVAL POCKETS

CROSS-REFERENCE TO RELATED APPLICATIONS

This application claims the benefit of U.S. Provisional Patent Application No. 61/624,177, filed Apr. 13, 2012, entitled "APPARATUS AND METHODS FOR CLEANING TEETH AND GINGIVAL POCKETS," and U.S. Provisional Patent Application No. 61/801,682, filed Mar. 15, 2013, entitled "APPARATUS AND METHODS FOR CLEANING TEETH AND GINGIVAL POCKETS," each of which is incorporated by reference herein in its entirety and for all purposes.

BACKGROUND OF THE INVENTION

Field of the Invention

The present disclosure relates generally to dentistry and oral hygiene, and, in particular, to apparatus, methods, and compositions for cleaning dental deposits from a mouth, including cleaning stains, calculus, plaque, caries, biofilms, etc. from one or more teeth and/or gum tissue, and removing deposits from the gingival sulcus, periodontal pockets, etc.

Description of the Related Art

Conventional techniques for cleaning undesirable deposits from teeth include brushing, flossing, scraping, rinsing with decalcifying or antibacterial or fluoride treatments, and other mechanical and/or chemical techniques. A person may clean his or her own teeth at home using a manual or electric toothbrush, floss, mouthwash, and various other items that may be purchased over the counter. Furthermore, for more detailed cleaning of teeth surfaces and gums, the person may go to the dentist, who can use more sophisticated mechanical and/or chemical techniques to clean outer surfaces of the teeth, gums, and spaces and pockets between the teeth and gums.

However, these conventional techniques may not be effective at cleaning all or substantially all the stains, calculus, caries, biofilms, plaque, tartar, etc. from the tooth or from the gingival sulcus, periodontal pockets, gums etc., or other organic and/or inorganic materials. Organic material (or organic matter) includes organic substances typically found in healthy or diseased teeth such as, for example, cellular matter, pus, microorganisms, bacteria, biofilms, and plaque, whether living, inflamed, infected, diseased, necrotic, or decomposed. Inorganic matter includes calcified tissue and calcified structures, calculus, tarter, etc., which are frequently present in or on teeth.

SUMMARY

Various non-limiting aspects of the present disclosure will now be provided to illustrate features of the disclosed apparatus, methods, and compositions. Examples of apparatus, methods, and compositions for endodontic treatments are provided.

In one embodiment, an apparatus for cleaning one or more teeth is disclosed. The apparatus can include a fluid retainer configured to be disposed at a treatment site on or near a tooth. The fluid retainer can be further configured to at least partially retain fluid in a space formed between the fluid retainer and the treatment site without sealing with the tooth. A pressure wave generator can be configured to generate pressure waves in the retained fluid to substantially clean deposits formed on an outer surface of the tooth or gum tissue.

In another embodiment, a method for cleaning one or more teeth is disclosed. The method can include applying a fluid retainer to a treatment site on or near a tooth. The method can further include retaining fluid in a space formed between the fluid retainer and the treatment site without sealing to the tooth. The method can also include activating a pressure wave generator to generate pressure waves in the retained fluid to substantially clean deposits formed on an outer surface of the tooth or gum tissue.

In another embodiment, an apparatus for cleaning a tooth in a mouth is disclosed. The apparatus can include a guide tube having a distal portion and a channel configured to direct a liquid jet toward the distal portion of the guide tube. The distal portion of the guide tube can be sized and shaped to be positioned between the gum tissue and the tooth. An impingement surface can be positioned near the distal portion of the guide tube such that, when the liquid jet impacts the impingement surface near a treatment site near the tooth, sufficient acoustic energy is generated to substantially clean deposits formed on the tooth or nearby gum tissue.

In yet another embodiment, a method for cleaning one or more teeth in a mouth is disclosed. The method can include supplying a treatment liquid into the mouth. The treatment liquid can be in contact with one or more teeth and adjacent gum tissue. The method can also include activating a pressure wave generator to generate pressure waves in the treatment liquid to substantially clean deposits formed on outer surfaces of the one or more teeth or gum tissue.

In another embodiment, a system for cleaning one or more teeth in a mouth is disclosed. The system can include a liquid inlet configured to deliver liquid to the mouth. The system can also include a handpiece comprising an active energy outlet having a distal portion. The distal portion can be sized and shaped to be inserted into the mouth. The active energy outlet can be configured to transmit energy through the liquid to substantially clean deposits formed on outer surfaces of the one or more teeth when the mouth is closed about the handpiece.

In another embodiment, dental cleaning system is disclosed. The system can include an active energy outlet including a first plate and a second plate spaced apart from the first plate. Each of the first and second plates can have a plurality of orifices. Each of the orifices can be configured to emit energy sufficient to substantially clean deposits formed on a tooth or gum tissue when the tooth or gum tissue is positioned between the first and second plates.

In yet another embodiment, a method for cleaning teeth is disclosed. The method can include at least partially filling a mouth with a water-based liquid. The method can include inserting a pressure wave generator into the mouth so as to be at least partially submersed in the water-based liquid. Further, the method can include closing the mouth with the pressure wave generator at least partially submerged in the water-based liquid. The method can also include energizing the pressure wave generator to produce acoustic pressure waves in the water-based liquid.

In yet another embodiment, a method for removing dental deposits from an exterior surface of one or more teeth or gum tissue in a mouth is disclosed. The method can include supplying treatment fluid to the mouth. The method can also include propagating acoustic energy being within a first frequency range through the treatment fluid in the mouth to remove at least a portion of the dental deposits in the mouth. Further, the method can include propagating acoustic energy being within a second frequency range through the treatment fluid in the mouth to remove at least a portion of the dental deposits in the mouth. The first frequency range can be of lower frequencies than the second frequency range.

In another embodiment, a system for cleaning teeth in a mouth of a mammal is disclosed. The system can include a fluid pump. A fluid reservoir can be in communication with the fluid pump. Furthermore, a mouthpiece can be in communication with the fluid pump. The mouthpiece can include a fluid port through which treatment fluid can be delivered to at least partially fill the mouth. A pressure wave generator can be coupled to the mouthpiece and can be arranged to be disposed within the mouth. The fluid pump can be operable to create oscillatory movement of the treatment fluid within a mouth, the volume of oscillatory movement being variable. The pressure wave generator can be configured to produce one or more frequencies in a first frequency range when the fluid pump creates a first volume of oscillatory movement of the treatment fluid within the mouth, and to produce one or more frequencies in a second frequency range when the fluid pump creates a second volume of oscillatory movement of the treatment fluid within the mouth.

In one embodiment, a system for removing dental deposits from an exterior surface of one or more teeth or gum tissue in a mouth of a mammal is disclosed. The system can include a mouthpiece sized and shaped to be inserted into the mouth. The mouthpiece can include one or more fluid ports. A fluid motion source can be in fluid communication with the mouthpiece. The fluid motion source can be configured to deliver liquid to the mouth and to remove liquid from the mouth through the one or more ports. The fluid motion source can be operable to create oscillatory movement of fluid to and from the mouth through the one or more ports at variable frequencies.

In another embodiment, a method for removing dental deposits from an exterior surface of one or more teeth or gum tissue in a mouth of a mammal is disclosed. The method can include inserting a mouthpiece into the mouth, the mouthpiece including one or more fluid ports. A fluid motion source that is in fluid communication with the mouthpiece can be activated to deliver liquid to the mouth and to remove liquid from the mouth through the one or more ports. The method can further include creating oscillatory movement of liquid to and from the mouth through the one or more ports at variable frequencies.

Accordingly, the treatment methods and apparatus disclosed herein may be useful in cleaning undesirable dental deposits from various portions of a patient's mouth, including, e.g., dental deposits on the teeth, gums, spaces between teeth, gingival pockets, etc. By not removing all or substantially all of such dental deposits, the deposits can progress and cause more serious tooth decay and/or gum disease. It can therefore be desirable to provide improved methods of cleaning undesirable deposits from teeth and/or gums or other portions of a person's mouth.

For purposes of this summary, certain aspects, advantages, and novel features of certain disclosed inventions are summarized. It is to be understood that not necessarily all such advantages may be achieved in accordance with any particular embodiment of the invention. Thus, for example, those skilled in the art will recognize that the inventions disclosed herein may be embodied or carried out in a manner that achieves one advantage or group of advantages as taught herein without necessarily achieving other advantages as may be taught or suggested herein. Further, the foregoing is intended to summarize certain disclosed inventions and is not intended to limit the scope of the inventions disclosed herein.

BRIEF DESCRIPTION OF THE DRAWINGS

The foregoing and other features, aspects, and advantages of the embodiments of the apparatus and methods of cleaning teeth are described in detail below with reference to the drawings of various embodiments, which are intended to illustrate and not to limit the embodiments of the invention. The drawings comprise the following figures in which:

FIG. 9 is a schematic side view of a fluid platform configured to be inserted into a mouth of a user to clean deposits from teeth, gums, and other surfaces of the mouth.

FIGS. 10A-10D are schematic side views of various types of fluid platforms that can be used in accordance with the fluid platform illustrated in FIG. 9.

Throughout the drawings, reference numbers may be re-used to indicate a general correspondence between referenced elements. The drawings are provided to illustrate example embodiments described herein and are not intended to limit the scope of the disclosure.

DETAILED DESCRIPTION

The present disclosure describes apparatus, methods, and compositions for performing dental procedures, including, e.g., preventative, restorative, endodontic, periodontic and other types of dental procedures. For example, the embodiments disclosed herein can be used to efficiently and non-invasively remove undesirable deposits and/or decay from (and/or to disinfect) one or more teeth, e.g., organic and/or inorganic matter that forms as deposits on outer surfaces of the teeth, including the removal of all or substantially all the stains, calculus, caries, biofilms, plaque, tartar, etc. from the teeth, or from the gingival sulcus, periodontal pockets, gums, space between teeth, etc. The regions of the teeth having undesirable dental deposits or decay may be on an outer surface of the teeth, on or in the gums, and/or in spaces or pockets between the teeth and gums. In some embodiments, the entire tooth and surrounding gums may be cleaned by the disclosed apparatus and methods.

I. Overview of Various Disclosed Embodiments

Figure 1A:
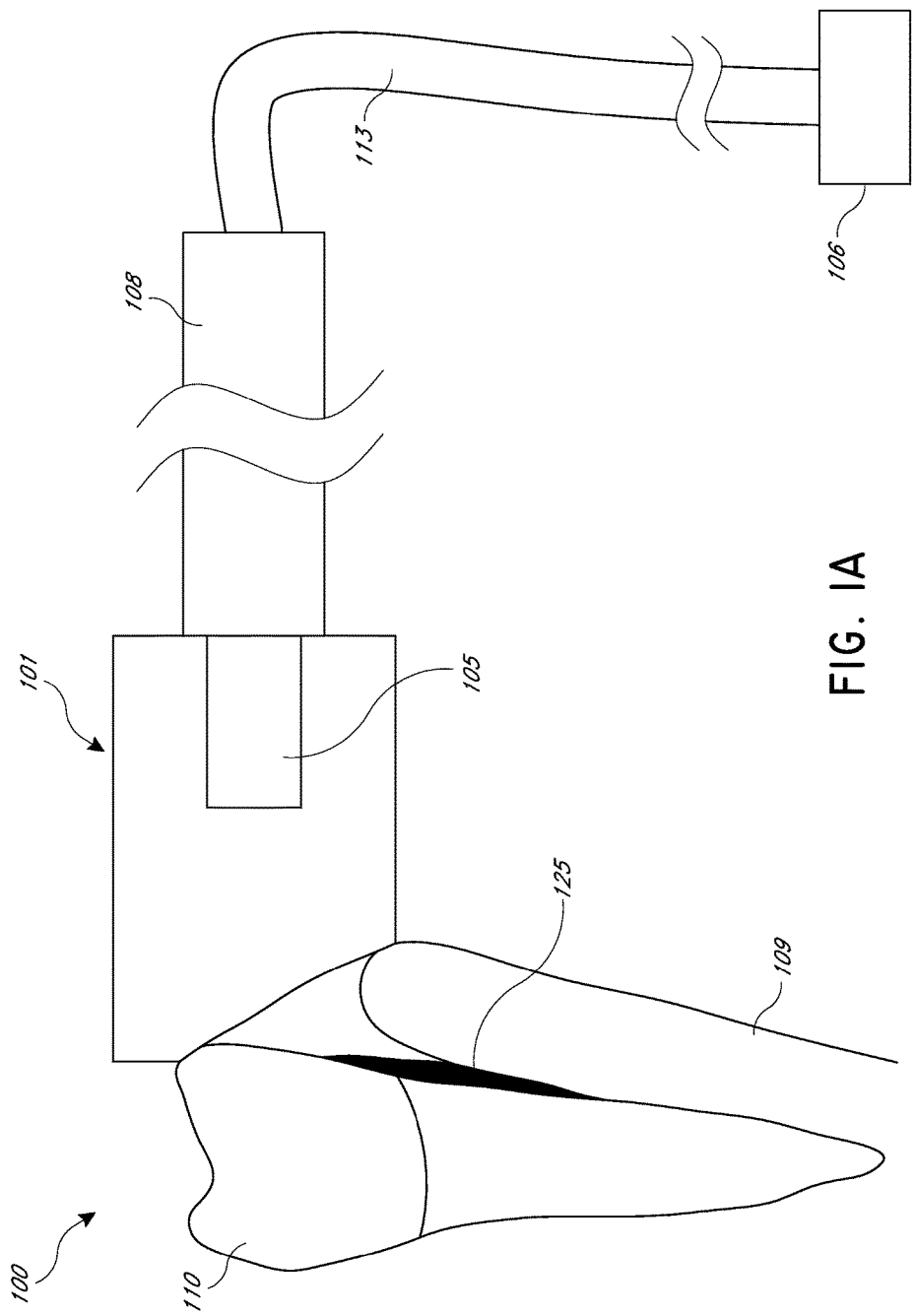
FIG. 1A is a schematic diagram of a dental system configured to clean dental deposits from a tooth and/or gums.

In various embodiments disclosed herein, a pressure wave generator can be used to remove stains, calculus, caries, biofilms, plaque, etc. (e.g., undesirable dental deposits) that have formed on one or more teeth (e.g., an outer surface of the teeth), gums, or gingival pockets. FIG. 1A illustrates a schematic diagram of a dental system 100 that includes components capable of removing undesirable dental deposits 125 from a tooth 110. Advantageously, the system 100 can remove the dental deposits 125 in a non-invasive manner without damaging the tooth 110 or the healthy soft tissue in the mouth, e.g. gum tissues. Further, the system 110 can more thoroughly remove the dental deposits 125 than conventional systems, such as toothbrushes, floss, or other dental instruments. For example, the system 100 can clean even small spaces between teeth, irregular tooth surfaces, cracks or other pockets between the teeth and/or the gums.

The system 100 can include a console 106, a handpiece 108, an active energy outlet 105, and a fluid platform 101 configured to couple to the tooth 110 to be treated. The active energy outlet 105 can include a pressure wave generator, a fluid motion source, or both. The pressure wave generator can be configured to generate pressure waves, and the fluid motion source can be configured to create movement of the fluid in a chamber or space (e.g., a chamber or space between the fluid platform 101 and the tooth 110, and/or an oral cavity of a subject's mouth), turbulence in the fluid in the chamber, circulation of the treatment fluid in the chamber and/or produce other dynamics in the fluid in the chamber. For example, the active energy outlet 105 can be configured to introduce fresh treatment liquid to the treatment site and/or to remove waste fluids from the treatment site. In some embodiments, the ingress and egress of treatment fluid from the treatment site is provided through one or more ports in the fluid platform 101. Additionally, in some embodiments, the pressure wave generator can create movement of the fluid in the chamber (that is, also function as a fluid motion source), as explained further below. The console 106 can be in electrical, electromagnetic, photonic, and/or fluid communication with the handpiece 108 by way of, e.g., various conduits 113 (e.g., fluid conduits, fiber optics, optical mirrors, and/or electrical wires) and can supply the handpiece 108 with treatment fluid, electrical power, control signals, etc. For example, the console 106 can include a fluid reservoir, a degassing system configured to remove dissolved gases from the treatment fluid, a pump, one or more sensors configured to measure properties of the treatment fluid, a mixing system, a controller configured to control the operation of the treatment procedure, and a user interface. A clinician can interact with the user interface of the console 106 to operate the system 100 and to manage the treatment procedure. For example, the clinician can use the console 106 to control and monitor various parameters of the treatment procedure, such as the supply of treatment fluid to the fluid platform 101, the activation of the active energy outlet 105 to clean the tooth 110, the current status of the procedure, and other suitable parameters.

The clinician can apply the fluid platform 101 to the treatment of one or more teeth 110, or, as will be appreciated herein, the clinician can insert the fluid platform 101 in the mouth without applying the fluid platform 101 to a particular tooth. In some embodiments, the fluid platform 101 can be part of the handpiece 108, in which case the clinician can use the handpiece 108 to couple the fluid platform 101 to the tooth 110. In other embodiments, the fluid platform 101 can be separate from the handpiece 108 and can be applied to the tooth 110 without using the handpiece 108. The clinician can use the handpiece 108 to position the active energy outlet 105 near or against the tooth 110 and to manipulate the fluid platform 101 and/or active energy outlet 105 during treatment. In some embodiments, a subject can use the handpiece 108 to position the active energy outlet 105 within his or her own mouth or oral cavity, and can activate the energy outlet 105 to clean the teeth and/or gums. The active energy outlet 105 can be activated to generate pressure waves in, on, or through the fluid platform 101, and/or to induce or enhance fluid motion (e.g., circulation, movement of fluid, turbulence, etc.) in the mouth. In various embodiments, the fluid platform 101 can facilitate the cleaning procedure by retaining treatment fluid to act as a medium for propagation of the pressure waves generated by the active energy outlet 105, and/or the fluid platform can enhance the circulation of treatment fluid in the tooth. In addition, the fluid platform 101 can include various components for facilitating aspiration, irrigation, fluid movement within the fluid platform 101, and/or the mixing of fluids before, during, and/or after treatment.

In some embodiments, a dental treatment procedure can include one or more phases designed to substantially remove the undesirable dental deposits from the teeth and/or gums. For example, as explained in more detail below, the active energy outlet (e.g., pressure wave generator) can generate pressure waves or acoustic energy having a broadband power spectrum. For example, the pressure wave generator can generate acoustic waves at multiple different frequencies, as opposed to only one or a few frequencies. Without being limited by theory, it is believed that the generation of power at multiple frequencies can help to remove various types of organic and/or inorganic materials that have different material or physical characteristics, and/or different bonding strengths at various frequencies. For example, some undesirable deposits may be removed from the teeth and/or gums at relatively low acoustic frequencies, while other deposits may be removed from the teeth and/or gums at relatively high acoustic frequencies, while still other deposits may be removed at intermediate frequencies between the relatively low and relatively high frequencies. In some embodiments, lower frequency cleaning phases can be activated at higher powers, and higher frequency cleaning phases can be activated at lower powers. In some embodiments, low frequency cleaning phases may be activated at relatively low powers, and high frequency cleaning phases may be activated at relatively high powers. In some embodiments, acoustic energy can be generated over a broadband frequency spectrum. As used herein, broadband frequencies and broadband frequency spectrum is defined regardless of secondary effects such as harmonics of the main frequencies and regardless of any noise introduced by measurement or data processing (e.g., FFT); that is, these terms should be understood when only considering all main frequencies activated by the pressure wave generator.

In some embodiments, the treatment procedure may include one or more treatment phases. In each treatment phase, energy can be applied at a different frequency or band of frequencies. For example, in one phase, energy (e.g., pressure waves) propagating at a relatively low frequency (or band frequencies) may be generated. The low frequency pressure waves can interact with the treatment fluid in the subject's mouth and can induce removal of large-scale dental deposits. Without being limited by theory, the low frequency pressure waves can remove a substantial portion of the dental deposits in the mouth. For example, the low frequency waves may have a sufficiently high energy at suitably low frequencies to remove large dental deposits from the teeth and/or gums at. The acoustic power at the relatively low frequencies can include acoustic power at any suitable low-frequency band of the power spectrum of the pressure wave generator (see, e.g., FIG. 13A). For example, in some embodiments, the acoustic power in the first, low-frequency range can include one or more frequencies in a range of about 0.1 Hz to about 100 Hz, for example in a range of about 1 Hz to about 50 Hz in some arrangements.

In another phase, acoustic energy may be generated at relatively high frequencies. At higher frequencies, the active energy outlet can be configured to remove smaller deposits and debris. For example, at higher frequencies, the pressure waves can propagate through the treatment fluid. The higher frequency waves can remove smaller deposits from relatively small locations, such as crevices, cracks, spaces, and irregular surfaces of the tooth. In some embodiments, degassed liquid can be used to enhance the removal of deposits from these small spaces. When the higher frequency cleaning is performed after the lower frequency cleaning, in some embodiments, the high frequency waves (and/or intermediate frequency waves) can clean the remainder of the deposits left behind from the low frequency cleaning. In the relatively high frequency phases, acoustic energy can be generated in a range of about 10 kHz to about 1000 kHz, e.g., in a range of about 100 kHz to about 500 kHz.

In some embodiments, the treatment procedure can progress from the relatively low frequencies (or bands of frequencies) toward higher frequencies (or bands of frequencies). For example, the procedure can move from the relatively low frequency phase(s), through intermediate frequency phase(s), until the high frequency phase(s) are reached. Thus, in some embodiments, the treatment procedure can provide a gradual and/or substantially continuous transition between relatively low and relatively high frequencies. As the treatment progresses through the frequencies, dental deposits of varying size and type can be removed by the active energy outlet. In other embodiments, however, the treatment procedure can transition or switch between frequencies (or bands of frequencies) or phases (e.g., between high, low and/or intermediate frequencies or bands of frequencies) at discrete levels. At various intermediate frequency ranges, acoustic energy can be generated in a range of about 100 Hz to about 10 kHz. For example, in some embodiments, the various phases of the treatment procedures described above may be activated by the user or clinician, or the active energy outlet can be configured to automatically transition between the phases. In some embodiments, for example, the active energy outlet can randomly switch between high, low, and intermediate frequencies.

Various treatment procedures may include any suitable number of treatment phases at various different frequencies. Furthermore, although various low- and high-frequency phases may be described above as occurring in a particular order, in other embodiments, the order of activating the low- and high-frequency phases, and/or any intermediate frequency phases, may be any suitable order.

In each of the embodiments disclosed herein, an active energy outlet can be configured to deliver treatment fluid to a mouth and to remove treatment fluid from the mouth in an oscillatory manner. The fluid movement of the treatment fluid to and from the mouth can oscillate at frequencies that vary during the treatment procedure. For example, in a first treatment phase, the fluid can move to and from the mouth at a first frequency in a first frequency range, and in a second treatment phase, the fluid can move to and from the mouth at a second frequency in a second frequency range. In some embodiments, the second frequency range can include frequencies that are higher than the frequencies in the first frequency range. For example, the first frequency range can include frequencies in a range of about 0.1 Hz to about 20 KHz. The second frequency range can include frequencies in a range of about 20 KHz to about 1,000 kHz. It should be further understood that multiple or a broadband or multiple broadband frequencies may be activated during at least a portion of the therapy (e.g., at least during a portion of the second treatment phase). The first treatment phase can be performed before the second treatment phase, or vice versa.

At lower frequencies, larger volumes of fluid can be moved to and from the mouth, and, at higher frequencies, smaller volumes of fluid can be moved to and from the mouth. In such arrangements, the lower frequency fluid movement can remove larger dental deposits, and the higher frequency fluid movement can remove smaller deposits disposed in small spaces, cracks, crevices, irregular surfaces, etc. In some embodiments, the first and second treatment phases can at least partially overlap. Moreover, in some treatment procedures, the frequency of fluid movement can be randomly changed. In other treatment procedures, the frequency of fluid movement can continually increase from low frequencies to high frequencies. In still other treatment procedures, the frequency of fluid movement can continually decrease from high frequencies to low frequencies. In further treatment procedures, the frequency of fluid movement can involve both increases and decreases through various frequency ranges.

In some embodiments, a treatment procedure can include an initial, start-up phase during which the user's mouth is filled with an adequate amount of liquid. For example, in some embodiments, the user's mouth may be only at least partially filled. In other embodiments, the user's mouth may be substantially filled. After the initial start-up phase, the embodiments disclosed herein can be configured to balance the amount of the treatment liquid inside the user's mouth during a treatment procedure, e.g., to maintain a substantially constant volume of treatment liquid inside the mouth. For example, when the user's mouth is filled with a suitable amount of liquid, a sensor can be triggered that signals the end of the initial, start-up phase and the beginning of a cleaning phase of the treatment procedure. A balancing mechanism can be triggered at the end of the start-up phase to balance the amount of liquid inside the user's mouth by substantially maintaining an equal amount of liquid inflow into the mouth and outflow out of the mouth, e.g., through one or more fluid ports. For example, in some embodiments, the balancing mechanism can include a sensor configured to monitor the pressure inside the user's mouth, and, through feedback, a controller can adjust the inflow and outflow. Furthermore, the controller can also be configured to trigger an emergency shut off in certain situations, for example, if there is a sudden change in pressure (or any other identifying characteristic of pressure) inside the user's mouth. In some embodiments, the pressure can be monitored by the delivery mechanism (e.g., fluid conduits) and the amount of force or pressure used to deliver fluid into the user's mouth. In some embodiment, the pressure can be monitored at the outflow, for example, by an evacuating mechanism. In some embodiments, the delivery (e.g., inflow) and evacuating (e.g., outflow) mechanism are the same or linked, for example, driven by the same driver or pump. The balancing mechanism can balance the inflow and outflow of treatment liquid regardless of liquid flow rate or frequency of operation. Thus, the amount of fluid in the mouth at any particular time can be maintained substantially constant regardless of the frequency of operation or the rates at which liquid is supplied into or out of the mouth.

Various advantages may be realized by the embodiments disclosed herein. For example, the fluid platforms 101 disclosed herein can be used to remove exterior stains from a tooth 110 in a non-invasive manner. Conventional dental techniques may use more invasive mechanical and/or chemical methods for removing tooth stains, such as yellow stains on exterior surfaces of a tooth 110. The embodiments disclosed herein may also be capable of removing a thin layer from the surface of a tooth, such as an organic or inorganic layer of dental deposits. Various embodiments may also be configured to remove caries, dental calculus, biofilms, and plaque from external surfaces of the tooth, gums, and spaces between the teeth and gums. In addition, the fluid platforms disclosed herein may also be able to clean the gingival sulcus and remove calculus, biofilm, and plaque from the gingival sulcus and other pockets or spaces between the tooth and the gums. For patients that have deep pockets (e.g., gingival sulcus that includes a deep space between the teeth and gums), the disclosed embodiments may also be able to clean these deep pockets and remove calculus, biofilm, plaque, and other deposits from these deep pockets. Furthermore, the fluid platforms disclosed herein may be used to help disinfect a patient's mouth and/or to provide mineralization therapy to the teeth and/or gums.

It should be appreciated that, compared to conventional dental techniques, the methods and apparatus disclosed herein can clean undesirable dental deposits from various portions of a patient's mouth in a non-invasive manner. For example, conventional techniques, such as using a file or coarse brush, may be uncomfortable or painful to the patient. Using generated pressure waves to clean the dental deposits can be done in a non-invasive manner that is not painful or uncomfortable to the patient. In addition, as explained herein, conventional techniques may not be able to clean all or substantially all the deposits from various portions of the patient's mouth. For example, deep gingival pockets may trap debris and undesirable deposits in locations that are inaccessible to toothbrushes or other conventional dental devices. By contrast, the pressure wave generators disclosed herein can propagate pressure waves through a treatment fluid to locations that are remote from the pressure wave generator, e.g., including deposits that are located deep within pockets between the gums and tooth. Thus, the methods and apparatus disclosed herein may advantageously clean, in a non-invasive manner, undesirable dental deposits from portions of the patient's mouth that may be inaccessible to conventional devices, and/or that may be inadequately cleaned by conventional devices.

Various details of pressure wave generators and fluid platforms may be found in U.S. patent application Ser. No. 11/737,710, filed Apr. 19, 2007, published Oct. 25, 2007, as U.S. Patent Publication No. 2007/0248932, entitled "APPARATUS AND METHODS FOR TREATING ROOT CANALS OF TEETH;" in U.S. patent application Ser. No. 12/945,791, filed Nov. 12, 2010, published May 19, 2011, as U.S. Patent Publication No. US 2011/0117517, entitled "LIQUID JET APPARATUS AND METHODS FOR DENTAL TREATMENTS;" U.S. patent application Ser. No. 13/279,199, filed Oct. 21, 2011, published Sep. 20, 2012, as U.S. Patent Publication No. 2012/0237893, titled "APPARATUS, METHODS, AND COMPOSITIONS FOR ENDODONTIC TREATMENTS;" in U.S. Provisional Patent Application No. 61/767,746, filed Feb. 21, 2013, entitled "APPARATUS AND METHODS FOR SEALING TEETH;" in U.S. Provisional Patent Application No. 61/624,177, filed Apr. 13, 2012, entitled "APPARATUS AND METHODS FOR CLEANING TEETH AND GINGIVAL POCKETS;" and in U.S. Provisional Patent Application No. 61/801,682, filed Mar. 15, 2013, entitled "APPARATUS AND METHODS FOR CLEANING TEETH AND GINGIVAL POCKETS," each of which is incorporated by reference herein in its entirety and for all purposes.

II. Example Features of the Disclosed Systems

A. Example Fluid Platforms

As explained herein, various fluid platforms 101 can be used to clean dental deposits from teeth 110, gums 109, and/or spaces between the teeth 110 and gums 109. Various components of such fluid platforms 101 are described herein. Note that the components of the fluid platforms 101 disclosed herein may be generally applicable and suitable for each embodiment disclosed herein, e.g., the embodiments of FIGS. 1A-12B. This disclosure should not be interpreted as limiting a particular feature of a fluid platform 101 to any particular embodiment disclosed herein, where suitable.

For example, a fluid platform 101 can be used to at least partially enclose the tooth 110, gums 109, pockets, etc., and can be used to maintain an enclosed volume (or chamber) at least partially filled (and in some arrangements, substantially filled) with liquid. In certain implementations, the fluid platform 101 can enable circulation of a treatment fluid near a region of a tooth 110. Further, in some arrangements, the fluid platform 101 can include components for enhancing aspiration, irrigation, and mixing. In some implementations, the fluid platform 101 can include embodiments of some or all of the following elements or features (and the elements or features disclosed above), which are intended to illustrate but not to limit the scope of the disclosure. Additional details of fluid platforms 101 that may be suitable for use with the embodiments disclosed herein may be found, e.g., in ¶¶ [0005], [0041]-[0049], [0058]-[0086] and various other portions of U.S. Patent Publication No. US 2012/0237893, published Sep. 20, 2012, which is incorporated by reference herein for all purposes.

1. Fluid Retainer or Cap

In some embodiments disclosed herein, the fluid platform 101 can include a fluid retainer configured to retain fluid in a treatment chamber or pocket. For example, the fluid retainer can be sized and shaped to at least partially or substantially enclose a portion of the tooth 110 and/or gums 109. In some embodiments, the cap can be coupled to or formed with a distal portion of the handpiece 108. The cap can include or define a chamber configured to retain treatment fluid at a treatment site, e.g., in gingival pockets in some embodiments. Liquid can be introduced into the chamber through a fluid inlet connected to, or disposed in or on, the handpiece 108. Waste treatment liquid can be removed through the fluid retainer by way of a fluid outlet and further into the handpiece 108. In various arrangements, the fluid retainer may be configured to cover a portion of a tooth, a whole surface of the tooth, and/or multiple teeth.

In some embodiments, the fluid retainer can include a clamp configured to attach to one or more teeth in a patient's mouth. The clamp can include multiple closable members biased to bear against the teeth 110 to secure the clamp to the teeth 110. The clamp can further include an impermeable material configured to retain a pool of treatment fluid.

In one embodiment, the path between the fluid retainer and the handpiece 108 (e.g., through the inlet and/or outlet) can include a permeable material through which liquid can flow. The fluid retainer can be used throughout the procedure and can be configured to withstand chemical exposure (such as irrigants introduced during the procedure). The fluid retainer can be formed of a flexible material in some embodiments. For example, the fluid retainer can be formed of an elastic material to at least partially, or substantially, enclose the tooth and/or gums. In some arrangements, the fluid retainer can include a sponge. The fluid retainer can include, for example, polyvinyl foam, polyethylene, polyvinyl alcohol (PVA), cellulose foam, silicone foam, etc. In other embodiments, the fluid retainer can comprise silicone, elastomer, rubber, latex, etc. In one embodiment, a material with substantially little acoustic dampening is chosen. By allowing only minimal or no acoustic dampening, the fluid retainer may not attenuate the pressure waves generated during the treatment procedure. In yet other embodiments, the fluid retainer can be made from one or more materials with different elasticities and/or degrees of firmness. It should be appreciated that the fluid retainers can have different shapes, depending on which tooth 110 is being treated (e.g., molar, incisor, canine, etc.) or the location of the treatment site on the tooth 110 (e.g., on a proximal surface, occlusal surface, lingual surface, buccal surface, etc.). In one embodiment, the fluid retainer can be part of, or integrally formed with, the handpiece 108. In another embodiment, the fluid retainer can be a separate piece from the handpiece 108, and can be mechanically coupled to a distal portion of the handpiece 108.

Additional details of fluid retainers, flow restrictors or caps that may be suitable for use with the embodiments disclosed herein may be found, e.g., in ¶¶ [0052]-[0053], [0115]-[0117] and various other portions of U.S. Patent Publication No. US 2011/0117517, published May 19, 2011; in ¶¶ [0040]-[0043], [0170]-[01 [0293]-[0299], [0316]-[0319] and various other portions of U.S. Patent Publication No. US 2012/0237893, published Sep. 20, 2012; and in FIG. 1 and the accompanying disclosure of U.S. Provisional Patent Application No. 61/767,746, filed Feb. 21, 2013, entitled "APPARATUS AND METHODS FOR SEALING TEETH," each of which is incorporated by reference herein for all purposes.

2. Components for Enhancing Aspiration and Irrigation

Some fluid platforms 101 can include various components that enhance aspiration and irrigation before, during, and/or after the treatment procedure. In some embodiments, treatment liquid can enter the treatment region near the tooth 110 via a fluid inlet, such as a treatment liquid inflow conduit. The fluid inlet can pass through or along the handpiece 108. Under steady state operation, the amount of liquid entering the at least partially enclosed volume can be substantially the same as the amount of liquid leaving the enclosed volume through the fluid outlet. In some embodiments, the fluid inlet can be driven by a pump, which can be controlled by the console 106. Furthermore, the fluid inlet can be the same as the active energy outlet 105 in some embodiments, such as in embodiments that employ a liquid jet device. Additional details of fluid inlets that may be suitable for use with the embodiments disclosed herein may be found, e.g., in ¶¶ [0075]-[0078] and various other portions of U.S. Patent Publication No. US 2012/0237893, published Sep. 20, 2012, which is incorporated by reference herein for all purposes.

As explained above, the fluid platforms 101 disclosed herein can also have a fluid outlet, e.g., an outflow conduit to transfer liquid out of the enclosed volume of the chamber, or directly out of the mouth, during the procedure. In some embodiments, waste treatment liquid may be allowed to spill directly into the patient's mouth. In other embodiments, however, waste treatment liquid (as well as removed material and byproduct gases) can be transferred through the fluid outlet, which can pass through or along the handpiece 108. As explained herein, the fluid outlet can be active or passive. In the case of a passive fluid outlet, the waste treatment liquid may move through the fluid outlet due to capillary forces, gravity, or because of a slight overpressure created in the enclosed volume or chamber. In the case of an actively pumped fluid outlet, the waste liquid can be transferred using a pump, suction, or other device that draws liquid out through the outlet. In one example, the fluid outlet is connected to the suction system and/or vacuum lines in the clinician's office. For example, in some embodiments, the inlet and outlet can be adjusted to maintain a balanced amount of fluid in the mouth and/or the fluid platform. Additional details of fluid outlets that may be suitable for use with the embodiments disclosed herein may be found, e.g., in ¶¶ [0079]-[0081] and various other portions of U.S. Patent Publication No. US 2012/0237893, published Sep. 20, 2012, which is incorporated by reference herein for all purposes.

As explained herein, the fluid platform 101 can also include one or more vents to regulate pressure of the treatment fluid. The vents can be disposed in a portion of the handpiece 108 in some arrangements, such as along a waste line or fluid outlet. The vents can take the form of a permeable or semi-permeable material (e.g., a sponge), openings, pores, or holes, etc. Additional details of vents that may be suitable for use with the embodiments disclosed herein may be found, e.g., in ¶¶ [0071]-[0073], [0082]-[0086], [0177]-[0194] and various other portions of U.S. Patent Publication No. US 2012/0237893, published Sep. 20, 2012, which is incorporated by reference herein for all purposes.

B. Handpiece

The systems 100 disclosed herein can include a handpiece 108, e.g., the handpieces disclosed herein with respect to FIGS. 1A through 12B. The handpiece 108 can be configured to apply the fluid platform 101 (e.g., the fluid retainer or cap) to the tooth 110 and/or to position the active energy outlet 105 relative to the treatment site. In some embodiments, the handpiece 108 can be used to create an at least partially or substantially enclosed volume or chamber as the handpiece 108 engages the fluid platform 101 with the tooth. Treatment liquids can be transferred into and out of the enclosed volume. In other embodiments, the handpiece 108 can be used to position a pressure wave generator or active energy outlet 105 near the treatment site.

In some embodiments, the handpiece 108 can include an elongated member having an energy outlet 105. The energy outlet 105 can be configured to clean dental deposits 125 from a tooth 110 and/or gums 109. The user can use the handpiece 108 to position the energy outlet 105 in his or her mouth and can activate a distal portion of the energy outlet 105 in the mouth.

In addition, the handpiece 108 can provide the operator, user or clinician with a handheld device to hold during the procedure. For example, the handpiece 108 can include user-friendly grips and a user-friendly shape to grasp. The clinician can manipulate the handpiece 108 to accurately position the fluid platform 101 and/or active energy outlet 105 at a desired position on or near the tooth 110. In addition, the handpiece 108 can allow the clinician to move or rotate the fluid platform 101 and active energy outlet 105 during the procedure so as to dispose the active energy outlet 105 at a desirable position relative to the treatment region in the mouth. Alternatively, the handpiece 108 can also provide a device for the operator to clamp or attach to the tooth 110 such that the handpiece 108 does not require substantial user intervention during the procedure. The handpiece 108 can be disposable (e.g., single-use), or the handpiece 108 can be reusable. In one embodiment, the handpiece 108 is disposable, but the active energy outlet 105 is reusable. The handpiece 108 can be formed of any suitable material. In some embodiments, the handpiece 108 can be formed of a plastic material. In other embodiments, the handpiece 108 can be formed of a metal. Additional details of handpieces that may be suitable for use with the embodiments disclosed herein may be found, e.g., in ¶¶ [0107], [0138]-[0142], [0156]-[0161] and various other portions of U.S. Patent Publication No. US 2012/0237893, published Sep. 20, 2012, which is incorporated by reference herein for all purposes.

C. Active Energy Outlets

An active energy outlet 105, or energy outlet, can be used in various disclosed embodiments to clean undesirable dental deposits 125 from a tooth 110 and/or gums 109, e.g., from outer or exterior surfaces of the tooth 110 and/or gums 109, or in pockets between the teeth 110 and gums 109. In some embodiments, the energy outlet 105 can comprise an elongated member having an active distal end portion. The active distal end portion can be activated by a user to apply energy to the treatment tooth 110 and/or gums 109 to remove deposits 125. In various embodiments, the energy outlet 105 can comprise two opposing plates configured to be applied over one or more teeth 110 and/or gums 109. Upon activation, energy can be output from the opposing plates to clean opposite surfaces of a tooth 110.

One type of energy outlet 105 is a pressure wave generator. As explained herein, the disclosed pressure wave generators can be configured to generate pressure waves with energy sufficient to clean undesirable dental deposits from a tooth, gum tissue, or spaces between the tooth and gums. The pressure wave generator can be a device that converts one form of energy into pressure waves within the treatment liquid. The pressure wave generator can induce, among other phenomena, fluid dynamic motion of the treatment liquid (e.g., in the chamber or mouth), fluid circulation, turbulence, and other conditions that can enable the cleaning of the tooth. The pressure wave generators disclosed in each of the figures described herein may be any suitable type of pressure wave generator.

The pressure wave generator can be used to clean dental deposits 125 by creating pressure waves that propagate through the treatment liquid, e.g., through treatment fluid retained at least partially retained in a fluid platform 101 (e.g., a fluid retainer). In some implementations, the pressure wave generator may also create cavitation, acoustic streaming, turbulence, etc. In various embodiments, the pressure wave generator can generate pressure waves or acoustic energy having a broadband power spectrum. For example, the pressure wave generator can generate acoustic waves at multiple different frequencies, as opposed to only one or a few frequencies. Without being limited by theory, it is believed that the generation of power at multiple frequencies can help to remove various types of organic and/or inorganic materials that have different material or physical characteristics at various frequencies.

The pressure wave generator (e.g., high-speed liquid jet, ultrasonic transducer, a laser fiber, etc.) can be placed at the desired location relative to the tooth 110 and/or gums 109. The pressure wave generator can create pressure waves within the liquid inside a substantially-enclosed volume and/or within fluid that circulates in a user's mouth or oral cavity. In general, the pressure wave generator can be sufficiently strong to remove organic and/or inorganic deposits 125 from teeth 110 and/or gums 109. In some embodiments, the pressure wave generator can be configured to avoid substantially breaking down or harming natural dentin and/or enamel.

For example, in some embodiments, the pressure wave generator can comprise a liquid jet device. The liquid jet can be created by passing high pressure liquid through an orifice. The liquid jet can create pressure waves within the treatment liquid. In some embodiments, the pressure wave generator comprises a coherent, collimated jet of liquid. The jet of liquid can interact with liquid in a substantially-enclosed volume (e.g., the chamber and/or the mouth of the user) and/or an impingement member to create the pressure waves. In addition, the interaction of the jet and the treatment fluid, as well as the interaction of the spray which results from hitting the impingement member and the treatment fluid, may assist in creating cavitation and/or other acoustic effects to clean the tooth.

In various embodiments, the liquid jet device can comprise a positioning member (e.g., a guide tube) having a channel or lumen along which or through which a liquid jet can propagate. The distal end portion of the positioning member can include one or more openings that permit the deflected liquid to exit the positioning member and interact with the surrounding environment in the tooth 110. In some treatment methods, the openings disposed at or near the distal end portion of the positioning member can be submerged in liquid that can be at least partially enclosed in a fluid platform 101 attached to or enclosing a portion of the tooth 110, gums 109, and or gingival pockets. In other embodiments, the openings disposed at or near the distal end portion of the positioning member can be submerged in a liquid that is within a subject's mouth or oral cavity. In some embodiments, the liquid jet can pass through the guide tube and can impact an impingement surface. The impact of the jet on the impingement surface can generate the pressure waves in some implementations. The flow of the submerged portion of the liquid jet (e.g., within a substantially filled fluid platform or within a subject's mouth or oral cavity) may generate a cavitation cloud within the treatment fluid. The creation and collapse of the cavitation cloud and/or the jet impacting the impingement surface may, in some cases, generate a substantial hydroacoustic field in or near the tooth, gums, and/or spaces between the tooth and gums. Further cavitation effects may be possible, including growth, oscillation, and collapse of cavitation bubbles. These (and/or other) effects may lead to efficient cleaning of the tooth. Additional details of a pressure wave generator that includes a liquid jet device may be found at least in ¶¶[0045]-[0050], [0054]-[0077] and various other portions of U.S. Patent Publication No. US 2011/0117517, published May 19, 2011, and in ¶¶[0136]-[0142] and various other portions of U.S. Patent Publication No. US 2012/0237893, published Sep. 20, 2012, each of which is incorporated by reference herein in its entirety and for all purposes.

As has been described, a pressure wave generator can be any physical device or phenomenon that converts one form of energy into pressure waves within the treatment fluid. Many different types of pressure wave generators (or combinations of pressure wave generators) are usable with embodiments of the systems and methods disclosed herein.

(i) Mechanical Energy

Pressure wave generators can include liquid jet devices, as explained above. Mechanical energy pressure wave generators can also include rotating objects, e.g. miniature propellers, eccentrically-confined rotating cylinders, a perforated rotating disk, etc. These types of pressure wave generators can also include vibrating, oscillating, or pulsating objects such as sonication devices that create pressure waves via piezoelectricity, magnetostriction, etc. In some pressure wave generators, electric energy transferred to a piezoelectric transducer can pressure waves in the treatment fluid. In some cases, the piezoelectric transducer can be used to create acoustic waves having ultrasonic frequencies.

(ii) Electromagnetic Energy

An electromagnetic beam of radiation (e.g., a laser beam) can propagate energy into a chamber, and the electromagnetic beam energy can be transformed into pressure waves as it enters the treatment fluid. In some embodiments, the laser beam can be directed into the chamber or space as a collimated and coherent beam of light. The collimated laser beam can be sufficient to generate pressure waves as the laser beam delivers energy to the fluid. Furthermore, in various embodiments, the laser beam can be focused using one or more lenses or other focusing devices to concentrate the optical energy at a location in the treatment fluid. The concentrated energy can be transformed into pressure waves sufficient to clean the undesirable dental deposits. In one embodiment, the wavelength of the laser beam or electromagnetic source can be selected to be highly absorbable by the treatment fluid in the chamber or mouth (e.g., water) and/or by the additives in the treatment fluid (e.g., nanoparticles, etc.). For example, at least some of the electromagnetic energy may be absorbed by the fluid (e.g., water) in the chamber, which can generate localized heating and pressure waves that propagate in the fluid. The pressure waves generated by the electromagnetic beam can generate photo-induced or photo-acoustic cavitation effects in the fluid. The electromagnetic radiation from a radiation source (e.g., a laser) can be propagated to the chamber by an optical waveguide (e.g., an optical fiber), and dispersed into the fluid at a distal end of the waveguide (e.g., a shaped tip of the fiber, e.g., a conically-shaped tip). In other implementations, the radiation can be directed to the chamber by a beam scanning system.

The wavelength of the electromagnetic energy may be in a range that is strongly absorbed by water molecules. The wavelength may in a range from about 300 nm to about 3000 nm. In some embodiments, the wavelength is in a range from about 400 nm to about 700 nm, about 700 nm to about 1000 nm (e.g., 790 nm, 810 nm, 940 nm, or 980 nm), in a range from about 1 micron to about 3 microns (e.g., about 2.7 microns or 2.9 microns), or in a range from about 3 microns to about 30 microns (e.g., 9.4 microns or 10.6 microns). The electromagnetic energy can be in the ultraviolet, visible, near-infrared, mid-infrared, microwave, or longer wavelengths.

The electromagnetic energy can be pulsed or modulated (e.g., via a pulsed laser), for example with a repetition rate in a range from about 1 Hz to about 500 kHz. The pulse energy can be in a range from about 1 mJ to about 1000 mJ. The pulse width can be in a range from about 1 μs to about 500 μs, about 1 ms to about 500 ms, or some other range. In some cases, nanosecond pulsed lasers can be used with pulse rates in a range from about 100 ns to about 500 ns. The foregoing are non-limiting examples of radiation parameters, and other repetition rates, pulse widths, pulse energies, etc. can be used in other embodiments.

The laser can include one or more of a diode laser, a solid state laser, a fiber laser, an Er:YAG laser, an Er:YSGG laser, an Er,Cr:YAG laser, an Er,Cr:YSGG laser, a Ho:YAG laser, a Nd:YAG laser, a CTE:YAG laser, a $CO_2$ laser, or a Ti:Sapphire laser. In other embodiments, the source of electromagnetic radiation can include one or more light emitting diodes (LEDs). The electromagnetic radiation can be used to excite nanoparticles (e.g., light-absorbing gold nanorods or nanoshells) inside the treatment fluid, which may increase the efficiency of photo-induced cavitation in the fluid. The treatment fluid can include excitable functional groups (e.g., hydroxyl functional groups) that may be susceptible to excitation by the electromagnetic radiation and which may increase the efficiency of pressure wave generation (e.g., due to increased absorption of radiation). During some treatments, radiation having a first wavelength can be used (e.g., a wavelength strongly absorbed by the liquid, for instance water) followed by radiation having a second wavelength not equal to the first wavelength (e.g., a wavelength less strongly absorbed by water) but strongly absorbed by another element, e.g. dentin, or nanoparticles added to solution. For example, in some such treatments, the first wavelength may help create bubbles in the fluid, and the second wavelength may help disrupt the tissue.

The electromagnetic energy can be applied to the chamber for a treatment time that can be in a range from about one to a few seconds up to about one minute or longer. A treatment procedure can include one to ten (or more) cycles of applying electromagnetic energy to the tooth. The fluid platform 101 can be used to circulate a fluid in the chamber during the treatment process, which advantageously may inhibit heating of the tooth 110 (which may cause discomfort to the patient). The fluid platform 101 can include a fluid platform 101 (e.g., a fluid retainer or cap) to assist retaining fluid in the chamber. The fluid platform 101 can inhibit splashback of fluid, which can occur by hydraulic self-ejection during certain pulsed laser treatments. The circulation of treatment fluid (e.g., water with a tissue dissolving agent) by the fluid platform 101 can bring fresh treatment fluid to tissue and organic matter as well as flush out dissolved material from the treatment site. In some treatments using electromagnetic radiation, circulation of the treatment fluid can increase the effectiveness of the cleaning (as compared to a treatment with little or no fluid circulation).

In some implementations, electromagnetic energy can be added to other pressure wave generation modalities. For example, electromagnetic energy can be delivered to a chamber in which a mechanical energy pressure wave generator (e.g., a liquid jet) is used to generate the acoustic waves.

(iii) Acoustic Energy

Acoustic energy (e.g., ultrasonic, sonic, audible, and/or lower frequencies) can be generated from electric energy transferred to, e.g., an ultrasound or other transducer or an ultrasonic tip (or file or needle) that creates pressure waves in the treatment fluid. The ultrasonic or other type of acoustic transducer can comprise a piezoelectric crystal that physically oscillates in response to an electrical signal or a magnetostrictive element that converts electromagnetic energy into mechanical energy. The transducer can be disposed in the treatment fluid, for example, in the fluid inside the chamber. As explained herein with respect to FIGS. 13A-13B, for example, ultrasonic or other acoustic devices used with the embodiments disclosed herein are preferably broadband and/or multi-frequency devices. For example, unlike the power spectra of the conventional ultrasonic transducer shown in FIG. 13B, ultrasonic or other acoustic devices used with the disclosed embodiments preferably have broadband characteristics similar to those of the power spectra of FIG. 13A (acoustic power of a liquid jet device).

(iv) Further Properties of Some Pressure Wave Generators

A pressure wave generator can be placed at a desired location with respect to the tooth 110. The pressure wave generator 110 creates pressure waves within the fluid inside the chamber (the generation of pressure waves may or may not create or cause cavitation). The pressure waves propagate throughout the fluid inside the chamber, with the fluid in the chamber serving as a propagation medium for the pressure waves. The pressure waves can also propagate through tooth material (e.g., dentin). It is believed, although not required, that as a result of application of a sufficiently high-intensity pressure wave, acoustic cavitation may occur. The collapse of cavitation bubbles may induce, cause, or be involved in a number of processes described herein such as, e.g., sonochemistry, tissue dissociation, tissue delamination, sonoporation, and/or removal of calcified structures. In some embodiments, the pressure wave generator can be configured such that the pressure waves (and/or cavitation) do not substantially break down natural dentin in the tooth 110. The pressure wave field by itself or in addition to cavitation may be involved in one or more of the abovementioned processes.

In some implementations, the pressure wave generator generates primary cavitation, which creates pressures waves, which may in turn lead to secondary cavitation. The secondary cavitation may be weaker than the primary cavitation and may be non-inertial cavitation. In other implementations, the pressure wave generator generates pressure waves directly, which may lead to secondary cavitation.

The energy source that provides the energy for the pressure wave generator can be located outside the handpiece 108, inside the handpiece 108, integrated with the handpiece 108, etc.

Additional details of pressure wave generators that may be suitable for use with the embodiments disclosed herein may be found, e.g., in ¶¶ [0191]-[0217], and various other portions of U.S. Patent Publication No. US 2012/0237893, published Sep. 20, 2012, which is incorporated by reference herein for all purposes.

Other active energy outlets may be suitable for use with the disclosed embodiments. For example, a fluid motion source can be disposed at a distal portion of a handpiece and/or can be coupled to a fluid platform in some arrangements. The fluid motion source can be configured to create movement of the fluid in a chamber or space (e.g., a chamber or space between the fluid platform 101 and the tooth 110, and/or an oral cavity of a subject's mouth), turbulence in the fluid in the chamber, circulation of the treatment fluid in the chamber and/or produce other dynamics in the fluid in the chamber. For example, the fluid motion source and/or the fluid platform 101 can include one or more inlets that are configured to inject fluid near the tooth to be treated. In addition, mechanical stirrers and other devices can be used to enhance fluid motion and cleaning. The fluid motion source can improve the circulation of the treatment fluid in a chamber and/or the patient's mouth, which can enhance the removal of dental deposits. For example, as explained below, faster mechanisms of reactant delivery such as "macroscopic" liquid circulation may be advantageous in some of the embodiments disclosed herein.

III. Cleaning Teeth and Gingival Pockets

Figure 1B:
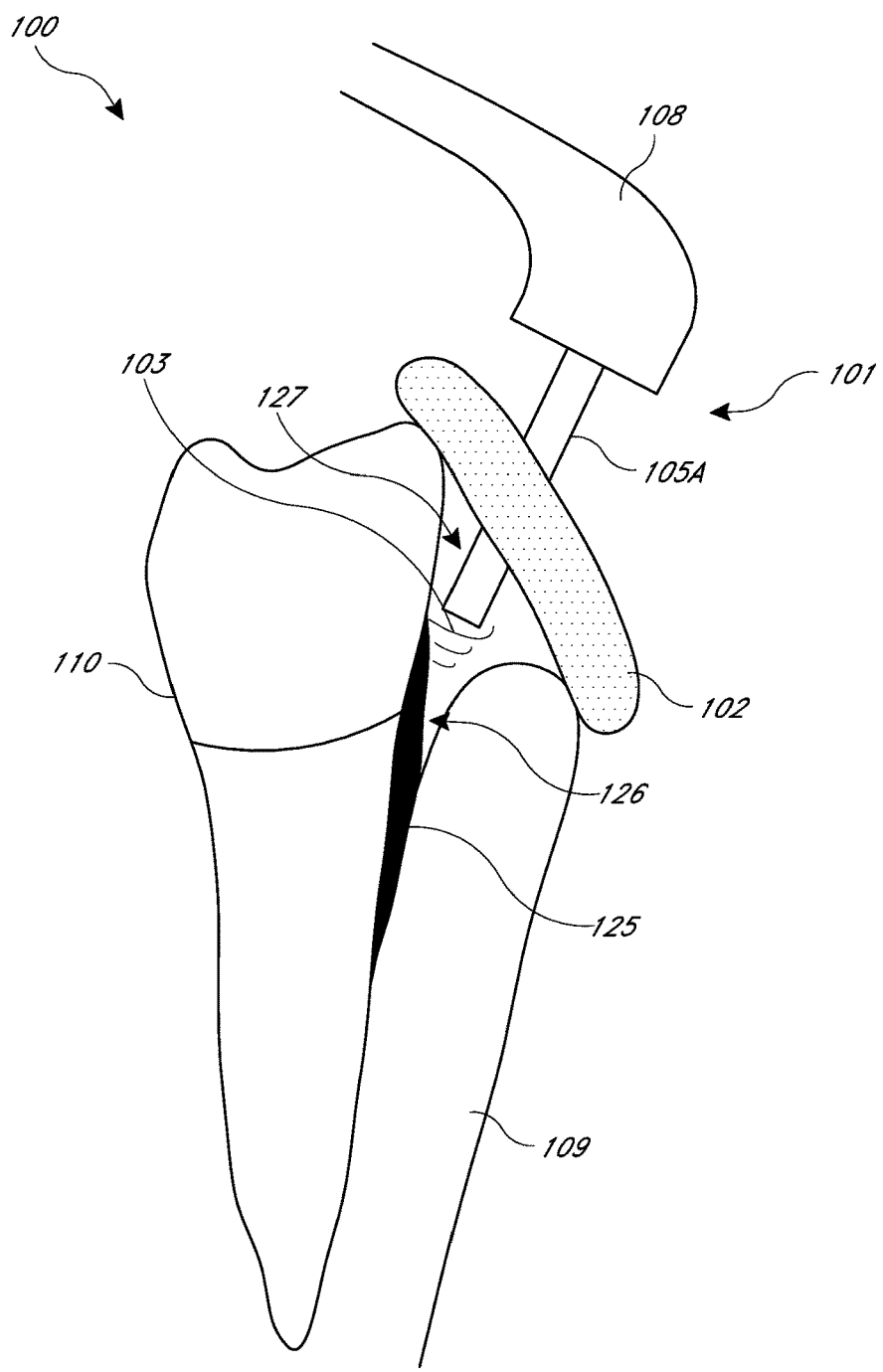
FIG. 1B is a schematic side view illustrating a dental apparatus having a fluid platform coupled to a treatment tooth and a portion of the gums near the tooth.

FIG. 1B is a schematic side view illustrating the dental system 100 having a fluid platform 101 coupled to a treatment tooth 110 and a portion of the gums 109 near the tooth 110. The system 100 can further include a handpiece 108, a pressure wave generator 105A, and a fluid retainer 102 (e.g., cap) configured to substantially enclose a chamber 127 between the fluid retainer 102, the gum tissue 109 and the treatment tooth 110 that remains at least partially filled with liquid during treatment procedure. In some embodiments, the chamber 127 between the gum tissue 109 and the treatment tooth 110 remains substantially filled with treatment liquid during treatment. The treatment liquid can be supplied by the pressure wave generator 105A in some embodiments (such as when the pressure wave generator 105A is a liquid jet device), or the treatment liquid can be supplied to the chamber 127 by a separate fluid introducer.

As shown in FIG. 1B, the chamber 127 can include at least a portion of a gingival pocket 126, e.g., the gingival sulcus. The illustrated pocket 126 may in general include the space between the tooth 110 and/or gums 109. If the pocket 126 progresses to a certain depth between the gums 109 and the tooth 110, a clinician may diagnose the pocket 126 as a periodontal pocket. If such a deep gingival pocket forms, organic and/or inorganic matter, e.g., dental deposits, may be disposed in the pocket, which can be difficult to treat using conventional treatment methods, such as using a toothbrush or other mechanical cleaning tool. For example, in FIG. 1B, gingival plaque or another type of dental deposit 125 may form on portions of the tooth 110 and/or gums 109, e.g., in the pocket 126. If the deposits 125 are formed deeply in the pocket 126 or space between the tooth 110 and gums 109, then it can be difficult to reach and clean the deposits 125 using, e.g., a toothbrush. If untreated, the deposits may progress and can cause tooth decay and/or gum disease.

In some embodiments, the pressure wave generator 105A can be coupled to or disposed near a distal portion of the handpiece 108. The fluid retainer 102 can be coupled to the pressure wave generator 105A and/or the handpiece 108. For example, in some embodiments, the pressure wave generator 105A can be disposed through the fluid retainer 102, such that a distal portion of the pressure wave generator 105A is positioned in the chamber 127. The clinician can use the handpiece 108 to manipulate the pressure wave generator 105A and the fluid retainer 102 to a portion of the patient's oral cavity for treatment. For example, the clinician can manipulate the handpiece 108 to dispose the fluid retainer 102 on portions of the tooth 110 and the gums 109 near the tooth 110. The fluid retainer 102 can be sized and shaped to at least partially or substantially enclose a portion of the tooth 110 and gums 109. Although the fluid retainer 102 of FIG. 1B is shown as being coupled to both the tooth 110 and the gums 109, in some arrangements, the fluid retainer 102 can be coupled only to the tooth 110 and/or only to the gums 109 during the treatment procedure. In some arrangements, the clinician can couple the fluid retainer 102 to the tooth 110 and/or gums 109 by pressing the fluid retainer 102 against the tooth 110 and/or gums 109. In other arrangements, an adhesive or sealant can be used to couple the fluid retainer 102 to the tooth 110 and/or gums 109.

It should be appreciated that, in some embodiments, the fluid retainer 102 may not provide a full liquid seal between the fluid retainer 102, the tooth 110, and the gums 109. Although some treatment fluid may be allowed to leak out from the chamber 127, in such embodiments, the fluid retainer 102 can be configured to retain enough treatment fluid in the chamber 127 such that sufficient pressure waves may be generated and propagated through the treatment fluid to substantially remove the dental deposits 125. Indeed, in various arrangements, sufficient treatment fluid can be supplied at a rate to replace any liquid that leaks or escapes from the chamber 127. In other arrangements, however, the fluid retainer 102 can provide a liquid seal that retains substantially all provided treatment liquid within the chamber 127. For example, the coupling force applied to the fluid retainer 102 may be sufficiently high to seal the chamber 127, and/or a sealant or adhesive may be applied to seal the fluid retainer 102 to the tooth 110 and/or gums 109.

For example, as shown in FIG. 1B, the fluid retainer 102 can at least partially or substantially enclose the chamber 127, which can include the pocket 126 between the tooth 110 and gums 109. Treatment fluid can be provided within the chamber 127 between the fluid retainer 102 and the tooth 110 and/or gums 109. In various embodiments, the chamber 127 can be at least partially filled with a liquid during treatment of the tooth 110. In some embodiments, for example, the chamber 127 between the fluid retainer 102 and the tooth 110 and gums 109 can be substantially filled with liquid during treatment. For example, the chamber 127 between the fluid retainer 102 and the tooth 110 and/or gums 109 can be filled above about 30% of the volume of the chamber 127, above about 50% of the volume of the chamber 127, above about 60% of the volume of the chamber 127, above about 75% of the volume of the chamber 127, above about 90% of the volume of the chamber 127, about 100% of the volume of the chamber 127, etc. In other embodiments, the treatment fluid can substantially fill the gingival pocket 126, but may not fill a substantial portion of the remainder of the chamber 127, e.g., the portion of the chamber 127 outside the gingival pocket 126.

A distal portion of the pressure wave generator 105A can be at least partially submerged in the treatment fluid in some embodiments. In other embodiments, the pressure wave generator 105A can be disposed outside the treatment fluid. The distal portion of the pressure wave generator 105A can be disposed outside the pocket 126 in some arrangements; in other arrangements, the distal portion of the pressure wave generator 105A can be disposed in a portion of the pocket 126. The pressure wave generator 105A can be activated inside the substantially enclosed treatment area to at least partially clean dental deposits from the teeth, gums, and/or spaces between the teeth and gums, including, e.g., stains, calculus, caries, biofilm, etc. For example, the pressure wave generator 105A can clean deposits in the gingival sulcus and/or periodontal pockets. The pressure wave generator 105A can clean teeth relatively quickly. For example, in some embodiments, the pressure wave generator 105A can be activated for less than about 20 minutes to clean the teeth and/or gums, depending on the amount of debris and/or deposit, and the location and extend of the treatment region. In particular, the pressure wave generator 105A can be activated for a time period in a range of about 0.5 minutes to about 15 minutes to substantially remove deposits that form on the teeth, gums, and/or spaces between the teeth and gums.

As shown in FIG. 1B, the pressure wave generator 105A can generate pressure waves 103 that propagate through the treatment fluid in the chamber 127. The pressure waves 103 can reach the dental deposits 125 formed on the tooth 110 and/or the gums 109. Without being limited by theory, it is believed, although not required, that by applying sufficiently high-intensity pressure waves 103, acoustic cavitation may occur. The collapse of cavitation bubbles may induce, cause, or be involved in a number of processes such as, e.g., sonochemistry, tissue dissociation, tissue delamination, sonoporation, etc., which may effectively lead to effective cleaning of deposits formed on a tooth, gums, or spaces between the teeth and gums. The pressure wave field by itself may also be involved in one or more of the above-mentioned processes. In some arrangements, the generation of pressure waves may or may not create or cause cavitation. In some embodiments, the pressure waves 103 can propagate through the fluid that at least partially or substantially fills the chamber 127 of the fluid retainer 102. The pressure waves 103 can interact with the dental deposits 125 of the tooth 110 and/or gums 109 to substantially remove the undesirable deposits. In some embodiments, the liquid that at least partially or substantially fills the chamber 127 can be a degassed liquid, which may improve cavitation and reduce the presence of gas bubbles in some treatments.

Figure 2:
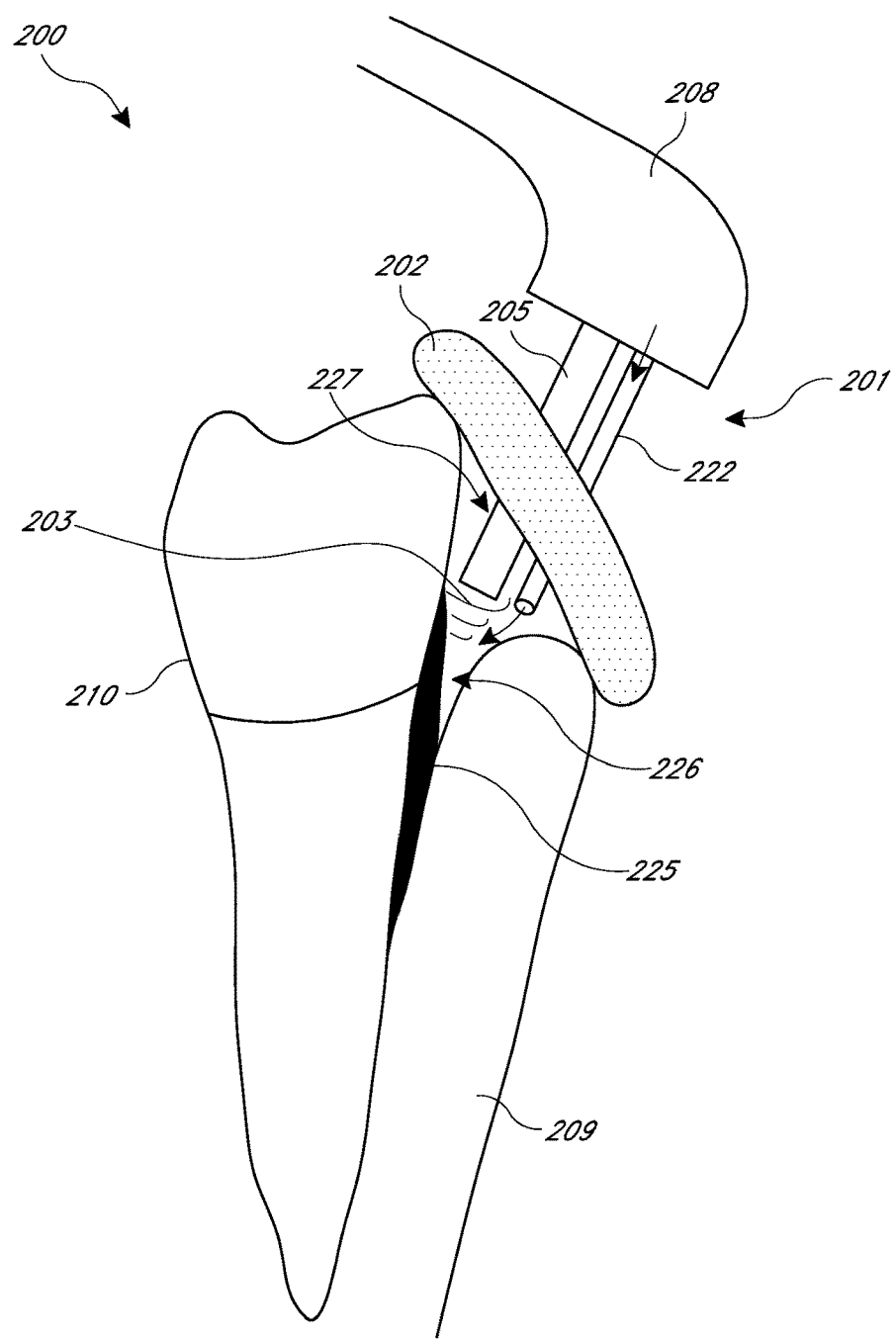
FIG. 2 is a schematic side view illustrating a dental apparatus having a fluid platform that includes an active fluid inlet.

FIG. 2 is a schematic side view illustrating a dental system 200 having a fluid platform 201 coupled to a treatment tooth 210 and a portion of the gums 209 near the tooth. As with FIG. 1B, an undesirable dental deposit 225 may be formed on the tooth 210 and/or the gums 209. In FIG. 2, reference numerals similar to those of FIG. 1B have been used to designate similar components and have been incremented by 100 relative to FIG. 1B. The foregoing description of those components should apply to the components of FIG. 2, unless otherwise noted.

For example, as in FIG. 1B, the system 200 can include a handpiece 208, a fluid retainer 202 or cap, and a pressure wave generator 205. The fluid retainer 202 can be coupled to a distal portion of the handpiece 208 and, when applied to the tooth 210 and/or gums 209, can define a chamber 227 that can be at least partially filled with a liquid during treatment of the tooth 210. For example, in some arrangements, the chamber 227 can be substantially filled with liquid during treatment (which can be a degassed liquid in some embodiments). The fluid retainer 202 can be applied to the tooth 210 without forming a full liquid seal in some arrangements. As with FIG. 1B, the fluid retainer 202 of FIG. 2 can be coupled to portions of the tooth 210 and/or the gums 209. As shown in FIG. 2, the chamber 227 can comprise a pocket 226 formed between the tooth 210 and the gums 209. As with FIG. 1B, the undesirable dental deposits 225 may be deposited on the tooth 210, gums 209, and/or in the pocket 226 between the tooth 210 and the gums 209.

Unlike the embodiment of FIG. 1B, the fluid platform 201 can include an active inlet 222 configured to dispense treatment liquid into a substantially enclosed treatment area, e.g., into the chamber 227. The active inlet 222 can be in fluid communication with a fluid reservoir and/or a pump configured to drive treatment fluid through conduits of the active inlet 222 and into the chamber 227 defined at least in part by the fluid retainer 202. The active inlet 222 can be configured to at least partially, or substantially, fill the chamber 227. The pressure wave generator 205 can be activated inside the liquid-filled chamber 227 to clean undesirable dental deposits, e.g., stains, calculus, caries, biofilm, etc. The pressure wave generator 205 and/or the fluid inlet 222 can cause fluid motion inside the treatment space, e.g., in the chamber 227, which can act to remove the dental deposits 225 formed on the tooth 210 and/or gums 209. In some arrangements, excess fluid entering the chamber 227 can flow out of the chamber 227 through gaps between the fluid retainer 202 and the tooth 210 and/or gums 209, such that the fluid platform 201 is an open fluid system. In other arrangements, an outlet can be provided to provide for the egress of waste fluid. In some embodiments, as shown in FIG. 2, the fluid inlet 222 is separate from the pressure wave generator 205. In other embodiments, the pressure wave generator can also act as a fluid inlet. In addition, the active inlet 222 can be configured such that any liquid that escapes from the chamber 227 through gaps between the fluid retainer 202 and the tooth 210 or gums 209 is replaced by the active inlet 222.

Figure 3:
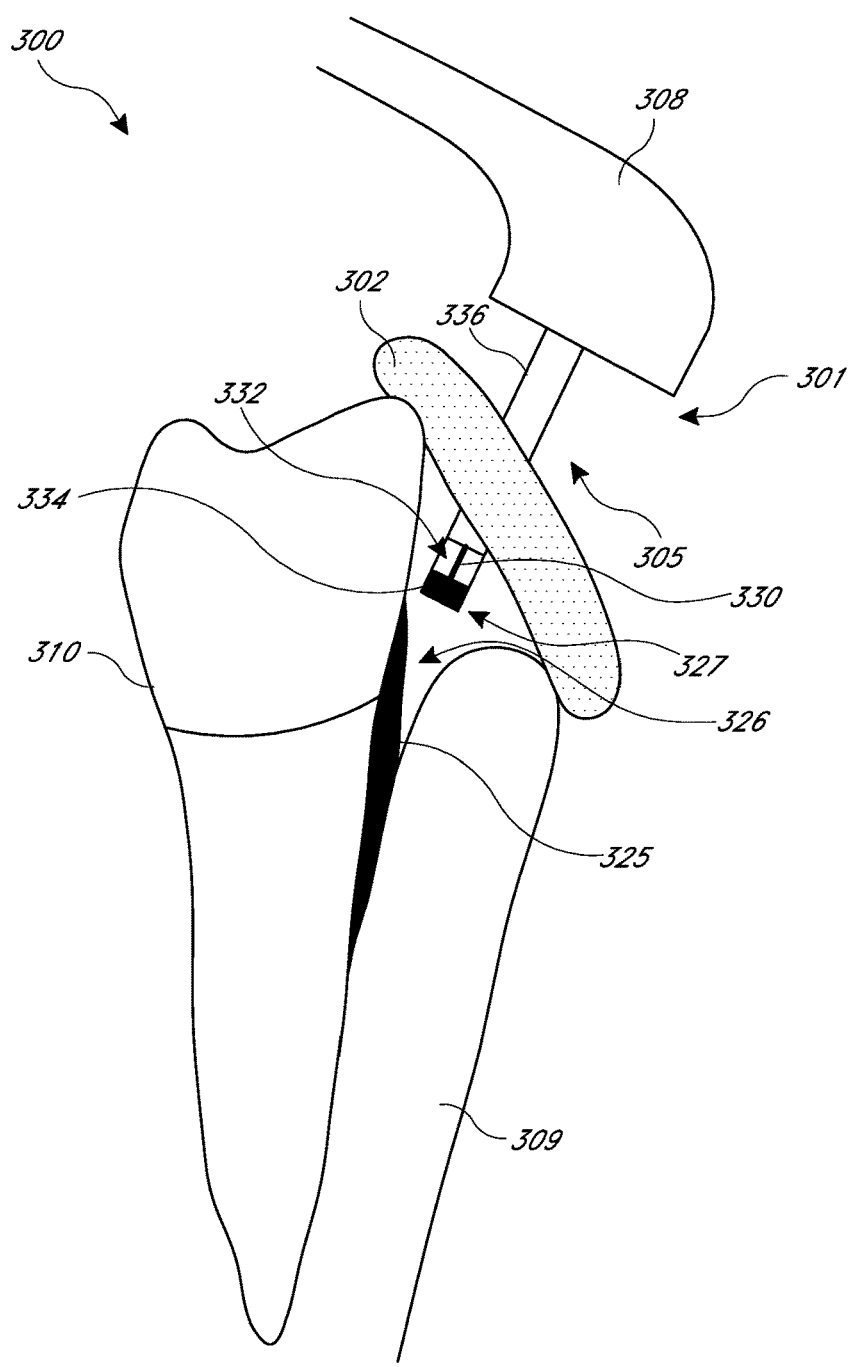
FIG. 3 is a schematic side view illustrating a dental apparatus having a fluid platform that includes a pressure wave generator comprising a liquid jet.

FIG. 3 is a schematic side view illustrating a dental system 300 having a fluid platform 301 and a pressure wave generator 305 comprising a liquid jet 330. An undesirable dental deposit 325 may be formed on the tooth 310 and/or the gums 309. In FIG. 3, reference numerals similar to those of FIGS. 1B-2 have been used to designate similar components and have been incremented by 100 relative to FIG. 2. The foregoing description of those components should apply to the components of FIG. 3, unless otherwise noted. The system 300 can include a handpiece 308, a fluid retainer 302 or cap, and a pressure wave generator 305. The fluid retainer 302 can be coupled to a distal portion of the handpiece 308 and, when applied to the tooth 310 and/or gums 309, can define a chamber 327 that can be at least partially filled with a liquid during treatment of the tooth 310. The flow retainer 302 can be used to at least partially or substantially enclose the space between gum tissue 309 and the treatment tooth 310 that remains at least partially filled with liquid during treatment. For example, in some arrangements, the chamber 327 can be substantially filled with liquid during treatment (which can be a degassed liquid in some embodiments). As with FIGS. 1B-2, the fluid retainer 302 of FIG. 3 can be coupled to portions of the tooth 310 and/or the gums 309. As shown in FIG. 3, the chamber 327 can comprise a pocket 326 formed between the tooth 310 and the gums 309. The undesirable dental deposits 325 may be deposited on the tooth 310, gums 309, and/or the pocket 326 between the tooth 310 and the gums 309.

As explained herein, the pressure wave generator 305 can comprise a liquid jet 330. The liquid jet 330 can be a coherent, collimated liquid jet. In some embodiments, for example, the jet 330 can be formed by an orifice through which a highly-pressurized liquid flows. The jet 330 can pass along a guide tube 336 and can impact an impingement member 334. The impingement member 334 can be a plate or other suitable impingement surface disposed near a distal portion of the guide tube 336. The jet 330 can hit or impact the impingement member 334. In some arrangements, the jet 330 can impact the impingement member 334 when the impingement member 334 is submerged in the treatment fluid. When the jet 330 impacts the impingement member 334, acoustic waves 303 can be generated and can propagate through the treatment fluid and can interact with, and substantially remove, the undesirable dental deposits 325, as explained herein.

In addition, in some embodiments, the liquid jet 330 can act as an active liquid inlet (similar to the inlet 222 of FIG. 2, for example) to dispense liquid into the substantially enclosed treatment area, e.g., into the chamber 327. The liquid jet 330 can also act as a source of fluid motion (e.g., a liquid motion generator), which may further enhance the cleaning procedure. For example, the pressure wave generator 305 can further comprise an opening 332 near a distal portion of the pressure wave generator 305. As shown in FIG. 3, the opening 332 can be disposed proximal the impingement member 334 in some arrangements. Liquid from the jet 330 may spray or pass through the opening 332 after impacting the impingement member 334. The liquid passing or spraying through the opening 332 may act to supply treatment fluid to the chamber 327 in some embodiments. Furthermore, the spray of liquid from the opening 332 to the chamber 327 may assist in providing fluid motion in the chamber 327, which may assist in cleaning undesirable deposits 325 from the mouth.

Figure 4:
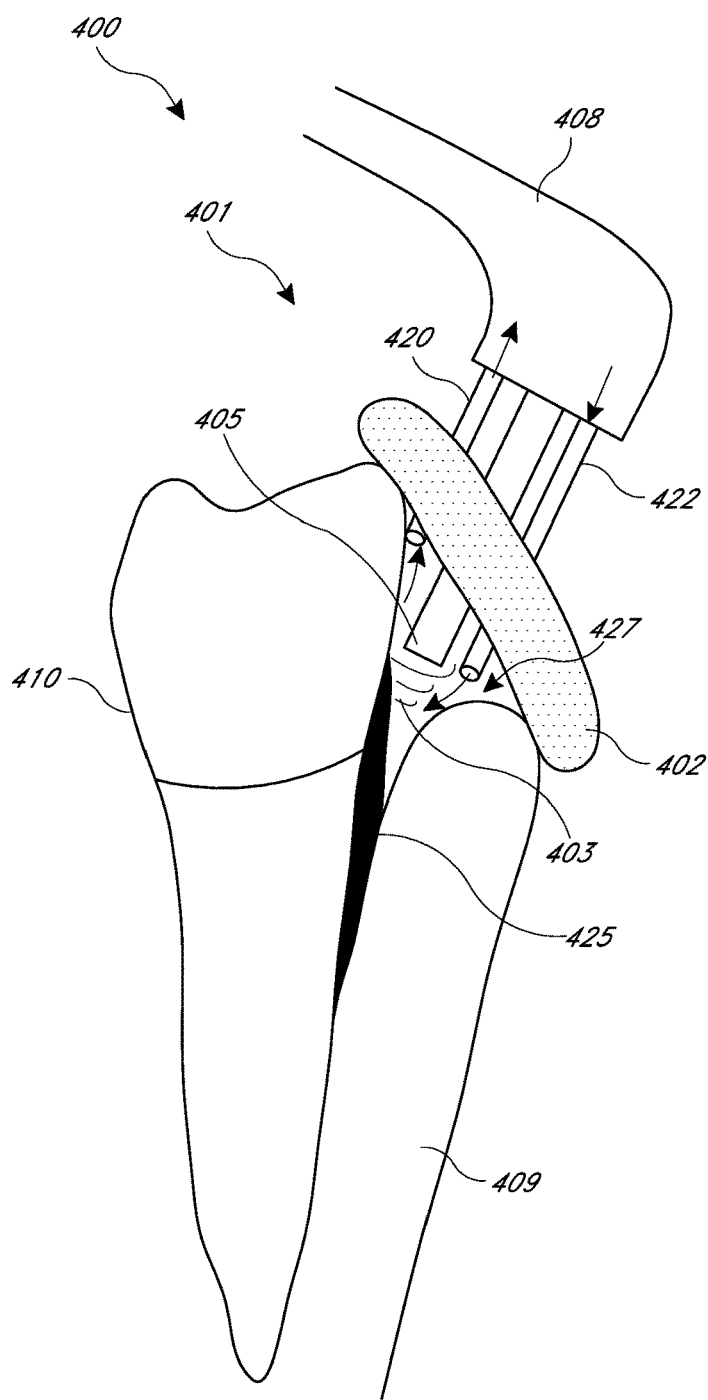
FIG. 4 is a schematic side view illustrating a dental apparatus having a fluid platform that includes an active fluid inlet and a fluid outlet.

FIG. 4 is a schematic side view illustrating a dental system 400 having a fluid platform 401 that includes an active fluid inlet 422 and a fluid outlet 420. An undesirable dental deposit 425 may be formed on the tooth 410 and/or the gums 409. In FIG. 4, reference numerals similar to those of FIGS. 1B-3 have been used to designate similar components and have been incremented by 100 relative to FIG. 3. The foregoing description of those components should apply to the components of FIG. 4, unless otherwise noted. As with FIGS. 1B-3, the system 400 can include a handpiece 408, a fluid retainer 402 or cap, and a pressure wave generator 405. The fluid retainer 402 can be used to substantially enclose the space between the gum tissue 409 and the treatment tooth 410 which can form a chamber 427 that remains at least partially, or substantially, filled with liquid during treatment. The pressure wave generator 405 can be activated inside the liquid-filled chamber 427 to generate pressure waves 403 that at least partially clean undesirable dental deposits 425, such as stains, calculus, caries, biofilm, and debris disposed in the gingival sulcus and periodontal pockets.

As with the embodiment of FIG. 2, the active fluid inlet 422 can dispense treatment liquid into the substantially enclosed treatment area, e.g., the chamber 427. The pressure wave generator 405 and/or the fluid inlet 422 can also induce fluid motion inside the treatment space, which can assist in removing the undesirable deposits 425. Further, the fluid inlet 422 can be configured to supply treatment fluid to the chamber 427 at a desirable rate to ensure that the appropriate amount of treatment liquid is maintained in the chamber 427 during treatment.

The fluid outlet 420 can comprise a waste fluid line configured to remove waste fluid from the substantially enclosed treatment space, e.g., the chamber 427. The fluid outlet 420 can be incorporated to allow waste liquid to exit the fluid retainer 402 into a hose which can be connected to a collection canister or a drain. The outlet 420 can be a passive outlet or an active outlet. For a passive fluid outlet 420, in some cases the waste treatment liquid moves through a conduit due to capillary forces, gravity, or because of a slight overpressure created in the substantially enclosed volume. For an actively pumped fluid outlet 420, the waste liquid can be transferred using a pump, suction, or other device that draws liquid out through an outflow conduit. In some arrangements, for example, the fluid outlet 420 can be connected to the suction system and/or vacuum lines in the clinician's office.

Figure 5:
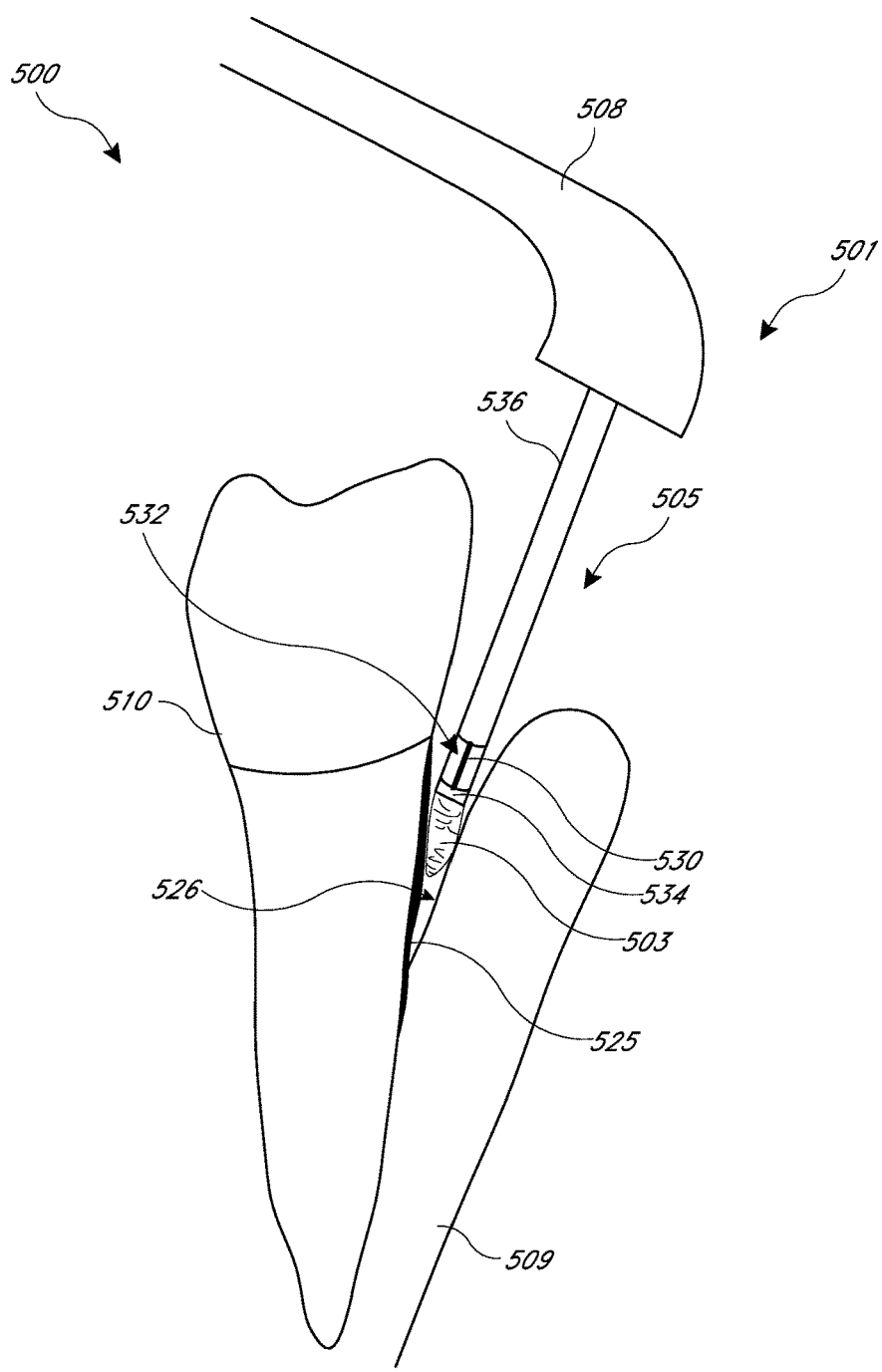
FIG. 5 is a schematic side view illustrating a dental apparatus having a fluid platform that includes a liquid jet apparatus.

FIG. 5 is a schematic side view illustrating a dental system 500 having a fluid platform 501 that includes a liquid jet apparatus 505 configured to remove dental deposits 525 from a treatment tooth 510, gums 509, and/or pockets 526 between the tooth 510 and gums 509. In FIG. 5, reference numerals similar to those of FIGS. 1B-4 have been used to designate similar components and have been incremented by 100 relative to FIG. 4. The foregoing description of those components should apply to the components of FIG. 5, unless otherwise noted. As with FIGS. 1B-4, the system 500 can include a handpiece 508. The liquid jet device 505 can couple to a distal portion of the handpiece 508, such that a clinician can maneuver the liquid jet device 505 to a region of the patient's mouth to be treated. In some embodiments, such as the embodiment of FIG. 5, there may be no fluid retainer or cap to assist in retaining fluid in a chamber near the tooth 510 and/or gums 509. For example, as shown in FIG. 5, a distal portion of the liquid jet device 505 can be sized and shaped to be positioned in or near the pockets 526 between the tooth 510 and gums 509.

The liquid jet device 505 can act as a pressure wave generator, as described herein, and/or the liquid jet device 505 can act as a fluid motion source. The liquid jet apparatus 505 can include a guide tube 536 having a channel through which a liquid jet 530 can pass. For example, as explained above, high-pressure liquid can pass through an orifice to form a coherent, collimated liquid jet that can pass along the guide tube 536. The jet 530 can impact an impingement member 534, which can generate pressure waves 503 in or near the pockets 526 between the tooth 510 and the gums 509. The liquid jet device 505 can also include an opening 532 near the distal portion of the liquid jet device 505. The opening 532 can be sized and shaped to allow liquid from the liquid jet 530 to spray or pass through the opening 532 after impacting the impingement member 534. Therefore, as explained above, the opening 532 in the guide tube 536 can also act as an active inlet to supply treatment fluid to the treatment tooth 510 in various arrangements.

In the embodiment of FIG. 5, the generated pressure waves 503 and/or the liquid passing through the opening 532 can act to at least partially clean deposits 525, e.g., stains, calculus, caries, and biofilms from the tooth 510 and/or gums 509, and debris or deposits in the gingival sulcus and periodontal pockets. Although the example system 500 shown in FIG. 5 does not include a fluid retainer, the pressure waves 503 can propagate through fluid in or near the pocket 526 to clean the deposits 525. Furthermore, without being limited by theory, in some arrangements, liquid passing from the guide tube 536 through the opening 532 and into the pocket 526 may act as a medium through which the pressure waves 503 can propagate to the deposits 525. In addition, in some embodiments, the liquid passing from the guide tube 536 through the opening 532 may act to improve fluid motion near the deposits 525. The generated pressure waves 503 and/or the circulated fluid in the pocket 526 may act to remove the deposits 525 from the tooth 510 and/or gums 509.

IV. Fluid Platforms for Coupling to One or More Teeth

Figure 6A:
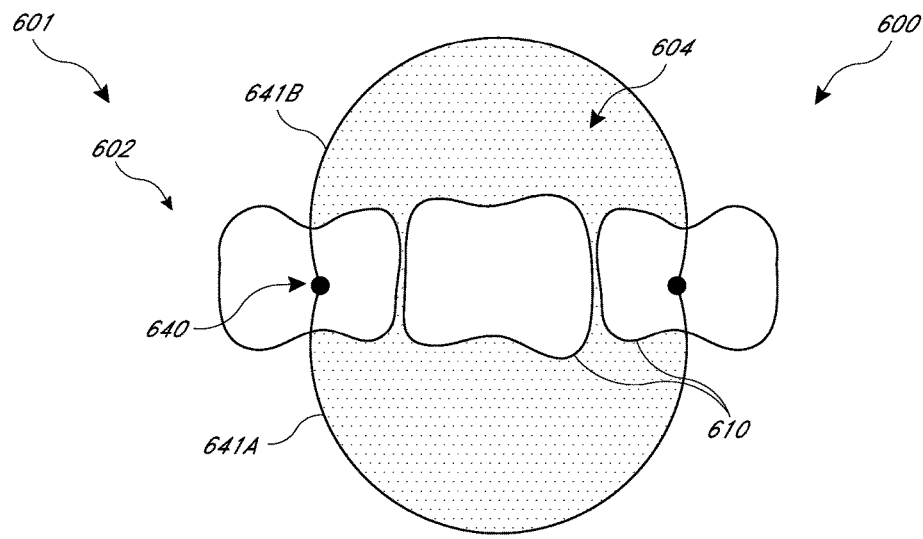
FIG. 6A is a top plan view of a dental apparatus that includes a fluid platform having a clamp configured to attach to one or more teeth, according to one embodiment.
Figure 6B:
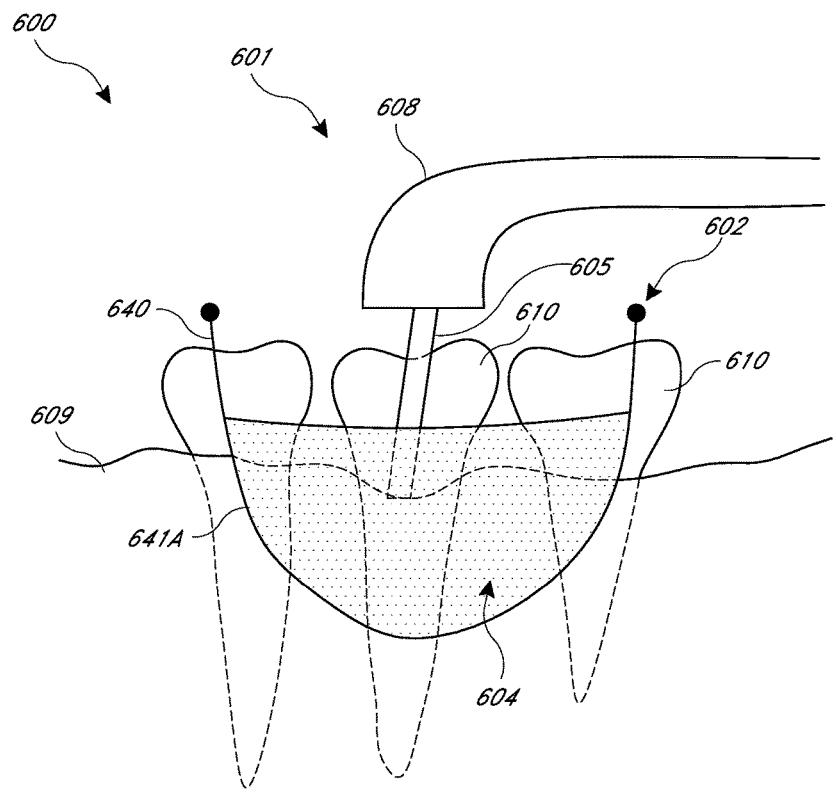
FIG. 6B is a schematic side view of the apparatus shown in FIG. 6A.

FIG. 6A is a top plan view of a dental system 600 that includes a fluid platform 601 having a fluid retainer 602 (e.g., a clamp 640 and a reservoir 604) configured to attach to one or more teeth 610 to retain a pool of treatment liquid. FIG. 6B is a schematic side view of the apparatus 600 shown in FIG. 6A. In FIGS. 6A-6B, reference numerals similar to those of FIGS. 1B-5 have been used to designate similar components and have been incremented by 100 relative to FIG. 5. The foregoing description of those components should apply to the components of FIGS. 6A-6B, unless otherwise noted. The system 600 shown in FIGS. 6A-6B can be used to clean one or more teeth 610 and/or gums 609 in a treatment region of the mouth. As explained herein, conventional dental treatment techniques may not effectively clean teeth to remove all or substantially all of the dental deposits that may form on the teeth and/or gums. The system 600 of FIGS. 6A-6B can generate pressure waves in the pool of treatment fluid retained in the reservoir 604 to remove all or substantially all the dental deposits formed on teeth 610 and/or gums 609. Advantageously, the pressure waves can clean portions of the teeth 610 and/or gums 609 that are remote from a pressure wave generator 605. For example, deposits located within gaps, cracks, crevices, etc. can be cleaned by pressure waves that propagate through the treatment fluid in the pool.

The system 600 can include the fluid retainer 602, a handpiece 608 and a pressure wave generator 605 coupled to a distal portion of the handpiece 608, as explained above. The fluid retainer 602 can include a clamp 640 that defines or forms a reservoir 604 configured to retain fluid. The clamp 640 can be used to at least partially enclose and seal the one or more treatment teeth 610. For example, the clamp 640 can be used to maintain the reservoir 604 at least partially filled with a pool of treatment fluid while providing access to the treatment handpiece 608, which can be positioned on or near the treatment tooth 610. The clamp 640 can be any suitable clamp. For example, the clamp 640 can include a first closable member 641A and a second closable member 641B. The first and second closable members 641A, 641B can be inwardly biased (e.g., biased towards one another) such that the clinician can apply the first and second closable members 641A and 641B on opposite sides of the one or more treatment teeth 610. When the clinician releases the clamp 640, the first and second closable members 641A and 641B can bear against the treatment teeth 610 and provide an at least partially enclosed and/or sealed reservoir 604 configured to be at least partially, or substantially, filled with treatment fluid. Each closable member 641A, 641B can also include a material that is impermeable to the treatment fluid such that, when the closable members 641A and 641B are clamped to the teeth 610 and/or gums 609, the impermeable material can define or form the reservoir 604 into which treatment fluid can be supplied.

The pressure wave generator 605 can be coupled to or disposed at the distal portion of the handpiece 608. As shown in FIG. 6B, for example, the distal portion of the pressure wave generator 605 can be submerged in the pool of treatment fluid retained in the reservoir 604. For example, the distal portion of the pressure wave generator 605 can be disposed in the reservoir 604 on either side of the teeth 610 in FIGS. 6A-6B, e.g., in the reservoir 604 formed by the first and/or second closable members 641A, 641B on opposing sides of the teeth 610. The pressure wave generator 605 can be activated to generate pressure waves. The pressure waves can propagate through the treatment fluid in the reservoir 604 to clean deposits from the teeth 610 and/or gums 609.

In addition, as explained above, the fluid platform 601 can include other components not illustrated in FIGS. 6A-6B, including, e.g., a fluid inlet, a fluid outlet, an additional fluid motion source, etc. For example, as explained above, the fluid inlet can be configured to supply treatment fluid to the pool 604 such that the inlet is able to resupply any fluid that leaks out of the pool 604 formed by the clamp 640. Furthermore, although the clamp 640 described herein with reference to FIGS. 6A-6B includes two closable members 641A and 641B, it should be appreciated that any other fluid platform may be suitable, including fluid platforms that form the pool 604 in alternate ways.

Figure 6C:
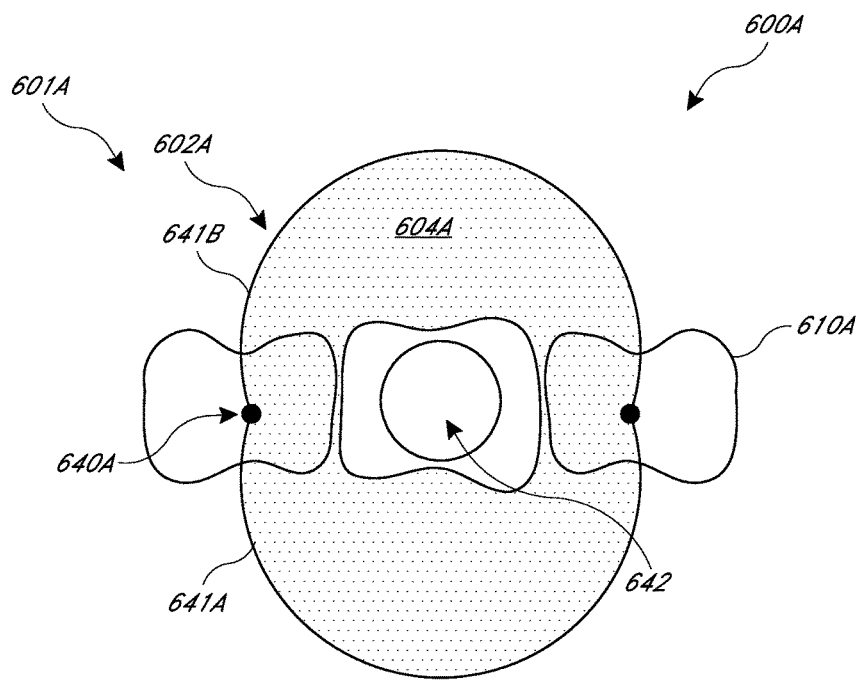
FIG. 6C is a top plan view of a dental apparatus that includes a fluid platform having a clamp configured to attach to one or more teeth, according to another embodiment.
Figure 6D:
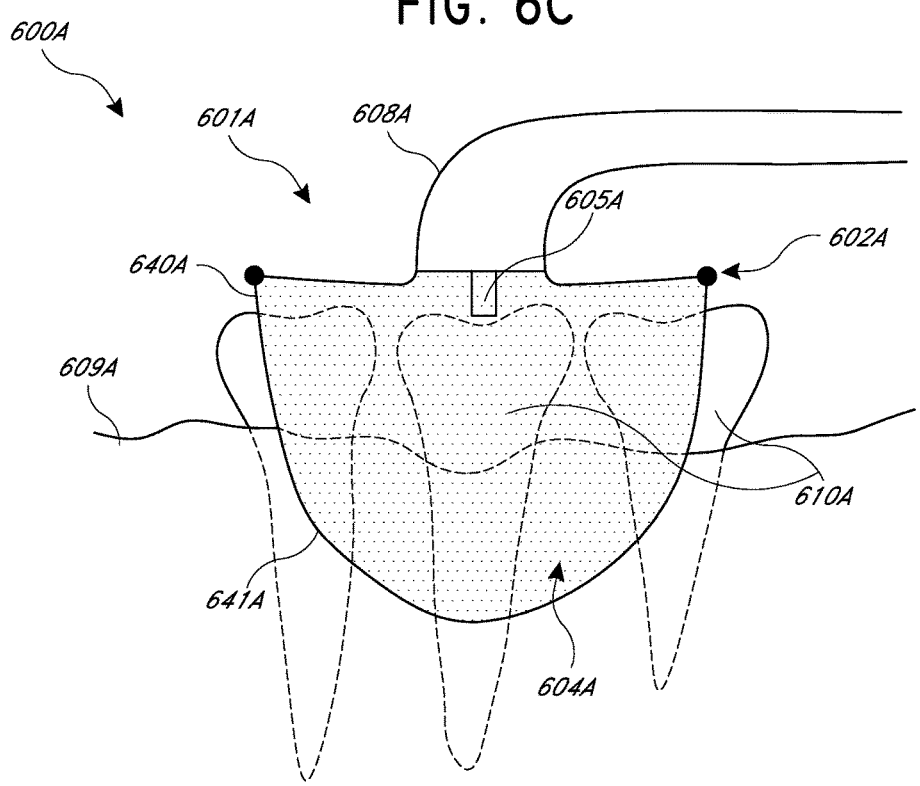
FIG. 6D is a schematic side view of the apparatus shown in FIG. 6C.

FIG. 6C is a top plan view of a dental system 600A that includes a fluid platform 601A having a fluid retainer 602A, in accordance with another embodiment. The fluid retainer 602A can include a clamp 640A configured to attach to one or more teeth 610A to form a reservoir 604A configured to be at least partially, or substantially, filled with treatment liquid. FIG. 6D is a schematic side view of the apparatus 600A shown in FIG. 6C. In FIGS. 6C-6D, reference numerals similar to those of FIGS. 6A-6B have been used to designate similar components and have been appended by "A" relative to FIGS. 6A-6B. The foregoing description of those components should apply to the components of FIGS. 6C-6D, unless otherwise noted. For example, as described above relative to FIGS. 6A-6B, the system 600A can include the fluid retainer 602A, a handpiece 608A, and a pressure wave generator 605A coupled to the handpiece 608A. The fluid retainer 602A can include a clamp 640A having closable members 641A and 641B that are configured to form a reservoir 604A that can be filled with a pool of treatment liquid. The clamp 640A can be used to at least partially enclose and seal the one or more treatment teeth 610A and to maintain the reservoir 604A at least partially, or substantially, filled with fluid.

The clamp 640A of FIGS. 6C-6D can also be configured to couple to the handpiece 608A, such that the clinician can attach the handpiece 608A to the clamp 640A. For example, in FIGS. 6C-6D, the clamp 640A can be coupled to a distal portion of the handpiece 608A. The clinician can couple the handpiece 608A to the clamp 640A before attaching the clamp 640A to the treatment teeth 610A in some arrangements. In other arrangements, however, the clinician can couple the handpiece 608A to the clamp 640A after attaching the clamp 640A to the treatment teeth 610A. As shown in FIGS. 6C-6D, the fluid platform 601A can include an aperture 642 through which the handpiece 608A can be coupled. For example, the pressure wave generator 605A and the distal portion of the handpiece 608A can be positioned in the aperture 642 and secured by any suitable securement mechanism, including, but not limited to, a snap-on mechanism, a threading mechanism, an adhesive, etc.

The distal portion of the pressure wave generator 605A can therefore be disposed within the reservoir 604A formed by the clamp 640A. The pressure wave generator 605A can be disposed through the aperture 642 above a tooth to be treated, as shown in FIG. 6D. In some embodiments, the distal portion of the pressure wave generator 605A can be submerged in the treatment fluid in the reservoir 604A. The pressure wave generator 605A can be activated to generate pressure waves that can propagate through the pool of treatment fluid retained in the reservoir 604A and can remove dental deposits formed on the teeth 610A and/or gums 609A. As with FIGS. 6A-6B, the fluid platform 601A can also include a fluid inlet, a fluid outlet, and/or a separate fluid motion source in various embodiments.

V. Systems for Cleaning Teeth and Gums

Daily teeth cleaning devices, such as toothbrushes, floss, mouthwash, etc., may not be effective at cleaning substantially all the undesirable deposits that form on teeth, gums, and/or spaces between the teeth and gums. Furthermore, to properly clean teeth and gums, it can be important to brush and/or floss for several minutes, multiple times every day. Users may not properly brush or floss their teeth, and/or they may not brush or floss for as long as needed, or as frequently as needed, to remove debris and deposits that form on the teeth and/or gums. Accordingly, there is a demand for providing improved methods and apparatus for cleaning teeth and gums, including improved daily teeth and mouth cleaning devices.

Figure 7A:
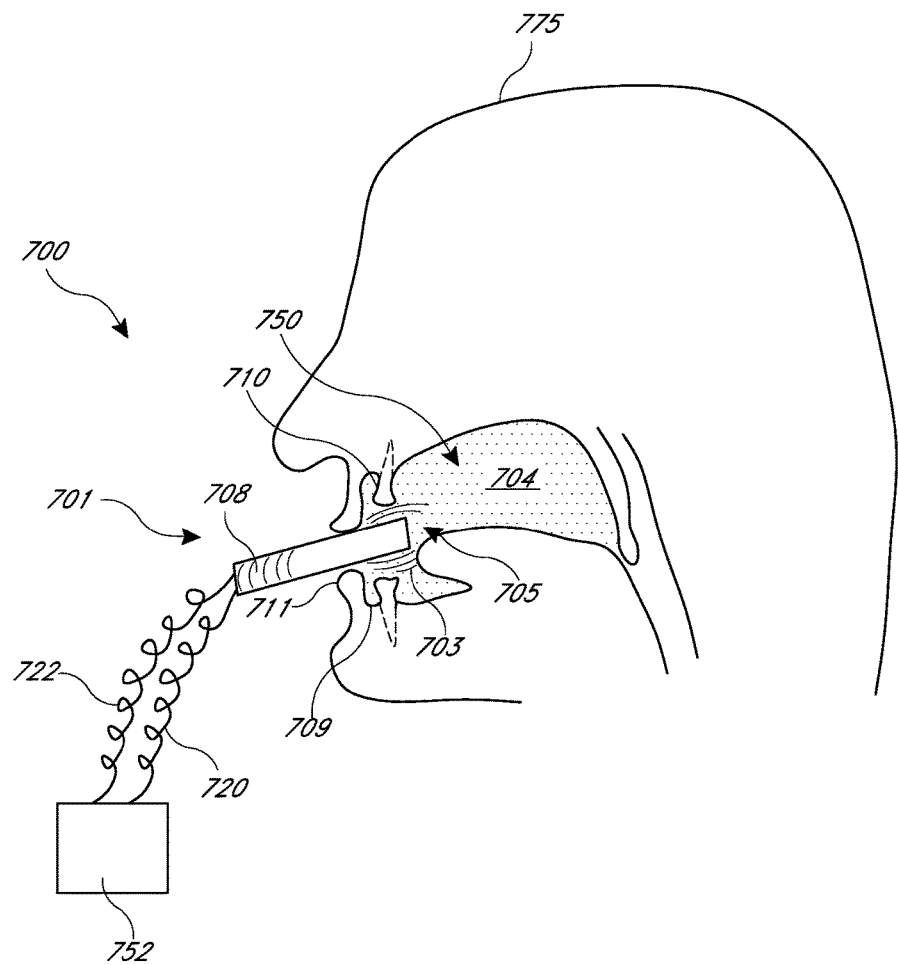
FIG. 7A is a schematic side view of a dental apparatus that includes a fluid platform configured to be inserted into a patient's mouth to substantially clean dental deposits from teeth and gums, according to one embodiment.

FIG. 7A is a schematic side view of a dental system 700 that includes a mouthpiece 701 configured to be inserted into a mouth 704 of a user 775 to substantially clean dental deposits from teeth 710 and gums 709. As above, the system 700 can clean dental deposits such as stains, calculus, caries, biofilms, etc. from teeth 710 and/or gums 709, and debris and deposits in the gingival sulcus and periodontal pockets. The mouthpiece 701 can include a handpiece 708, an active energy outlet 705, a fluid inlet line 722, and a fluid outlet line 720. The handpiece 708 can be part of the mouthpiece and can be used to manipulate the mouthpiece 701 in the mouth of the user. The energy outlet 705 can include one or more of a pressure wave generator (such as the pressure wave generators described herein), a fluid motion source configured to circulate fluid in the mouth 704, and/or a liquid ejector configured to eject liquid into the mouth 704. In addition, the apparatus 700 can include a fluid treatment system 752. The fluid treatment system 752 can include one or more pumps, reservoirs, mixers, sensors, and other components that are configured to prepare the treatment fluid, drive the fluid through the inlet line 722, and dispose of waste fluid received from the outlet line 720.

The system 700 can be held in a hand of the user 775. To clean the mouth 704 of the user 775, including, e.g., the user's teeth 710, gums 709, and other mouth surfaces, the user 775 can insert a distal portion of the energy outlet 705 into the mouth 704 using the handpiece 708. The user can enclose his or her lips 711 around a portion of the handpiece 708, e.g., a portion of the handpiece 708 proximal of the distal portion of the energy outlet 705. Enclosing the lips 711 about the handpiece 708 can substantially seal the mouth 704 such that liquid supplied in the mouth 704 is substantially retained. Treatment liquid 750 can be pumped or otherwise supplied through the inlet line 722 and can at least partially, or substantially, fill the mouth 704. Once the mouth is adequately filled with treatment liquid 750, the energy outlet 705 can be activated to remove deposits from surfaces of the mouth, including surfaces of the teeth 710 and/or gums 709. For example, pressure waves 703 generated by a pressure wave generator of the energy outlet 705 can propagate through the treatment liquid 750 in the mouth and can remove deposits from the teeth 710 and gums 709. In some arrangements, the user 775 may not bite down on the handpiece 708 using his or her teeth 710. Further, in some embodiments, the user 775 can move the energy outlet 705 within the mouth 704 (e.g., by rotating or translating the distal portion of the energy outlet 705 relative to the mouth 704). Moving the energy outlet 705 in the mouth 704 can act to apply varying intensities of the pressure waves 703 at various portions of the mouth 704 and/or can act to induce the motion of fluid 750 in the mouth 704. During the procedure, the outlet line 720 can remove excess treatment fluid 750 or waste fluid, while the inlet line 720 maintains the mouth 704 substantially filled with treatment liquid 750.

The system 700 disclosed in FIG. 7A can advantageously clean deposits from the teeth 710 and/or gums 709 without the use of a toothbrush, floss, mouthwash, or other conventional dental cleaning items. By using the energy outlet 705 to generate pressure waves 703 through the treatment liquid 750, the system 700 can remove deposits that are formed on mouth surfaces that are difficult to reach using conventional dental devices. Furthermore, the use of the pressure wave generator can clean the mouth 704 in a short amount of time and in a non-invasive manner. In some arrangements, for example, the pressure wave generator of the energy outlet 705 can be activated for less than about 20 minutes. For example, in some cases, the pressure wave generator can be activated for a time period in a range of about 0.5 minutes to about 15 minutes to substantially remove undesirable dental deposits from the mouth 704.

Figure 7B:
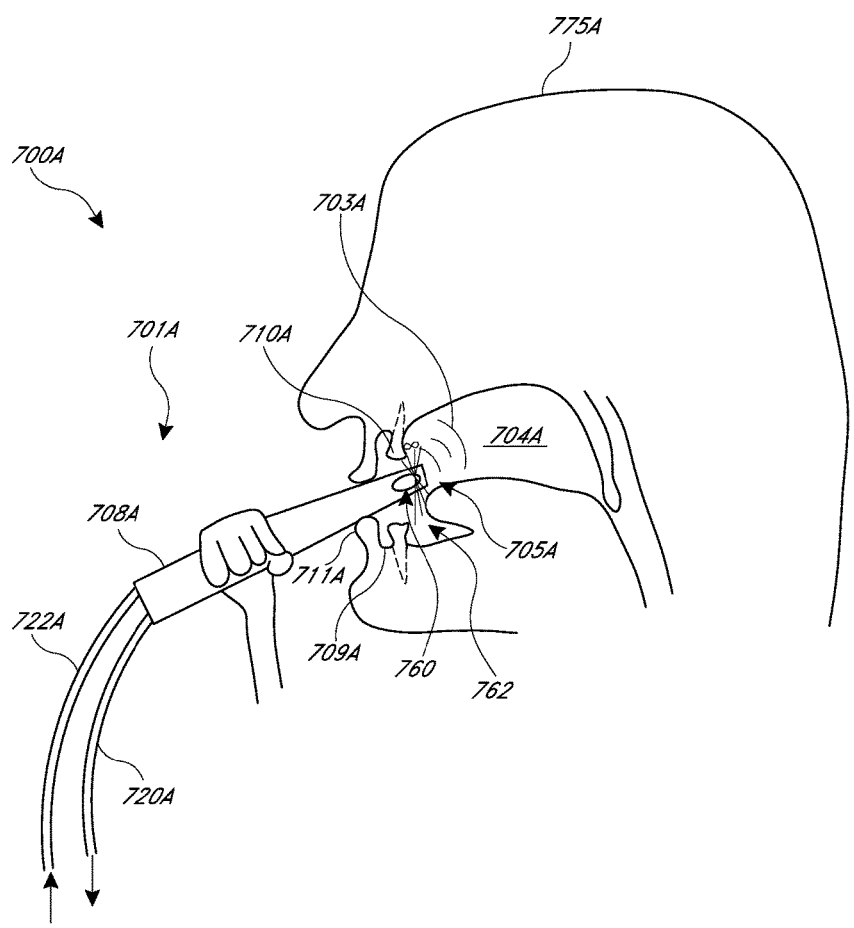
FIG. 7B is a schematic side view of a dental apparatus that includes a fluid platform configured to be inserted into a mouth of a user to substantially clean dental deposits from teeth and gums, according to another embodiment.

FIG. 7B is a schematic side view of a dental system 700A that includes a mouthpiece 701A configured to be inserted into a mouth 704A of a user 775A to substantially clean dental deposits from teeth 710A and gums 709A, according to another embodiment. In FIG. 7B, reference numerals similar to those of FIG. 7A have been used to designate similar components and have been appended by the letter "A" relative to FIG. 7A. The foregoing description of those components should apply to the components of FIG. 7B, unless otherwise noted. For example, as with FIG. 7A, the mouthpiece 701A of FIG. 7B can include a handpiece 708A, an energy outlet 705A, a fluid inlet line 722A, and a fluid outlet line 720A.

Unlike the embodiment of FIG. 7A, however, in FIG. 7B, the mouth 704A of the user 775A may not be filled with treatment fluid prior to activating the energy outlet 705A. For example, the handpiece 708A can include an opening 760 near the distal portion of the energy outlet 705A. In the system 700A of FIG. 7B, the user 775A can enclose his or her lips 711A about a portion of the handpiece 708A to seal the mouth 704A around the handpiece 708A. The energy outlet 705A can be activated such that a pressure wave generator is activated and treatment fluid 762 is ejected from the opening 760 into the mouth 704A. The energy outlet 705A can generate pressure waves 703A, while the fluid 762 that passes through the opening 760 of the handpiece 708A can increase the fluid motion in the mouth 704A. In some embodiments, the pressure waves 703A may propagate through the liquid 762 that is ejected through the opening 760 in the handpiece 708A.

For example, in some embodiments, the user 775A can move the distal portion of the energy outlet 705A around the inside of the mouth 704A and along the surfaces of the teeth 710A. The fluid 762 ejected from the opening 760A may be sprayed or otherwise flowed over the teeth 710A and surfaces in the mouth 704A, and may increase the motion of fluid in the mouth 704A. In some embodiments, as the energy outlet 705A is moved within the mouth 704A, generated pressure waves 703A may propagate from the energy outlet 705A to the surfaces of the teeth 710A and/or gums 709A. In some arrangements, the pressure waves 703A may propagate through the treatment liquid 762 that circulates through the mouth 704A (e.g., the liquid 762 that is circulated as it passes through the opening 760 of the handpiece 708A), and may couple to the teeth 710A and/or gums 709A to remove undesirable dental deposits. In some embodiments, at least some treatment fluid may be supplied to the mouth 704A before activating the system 700A.

Figure 8:
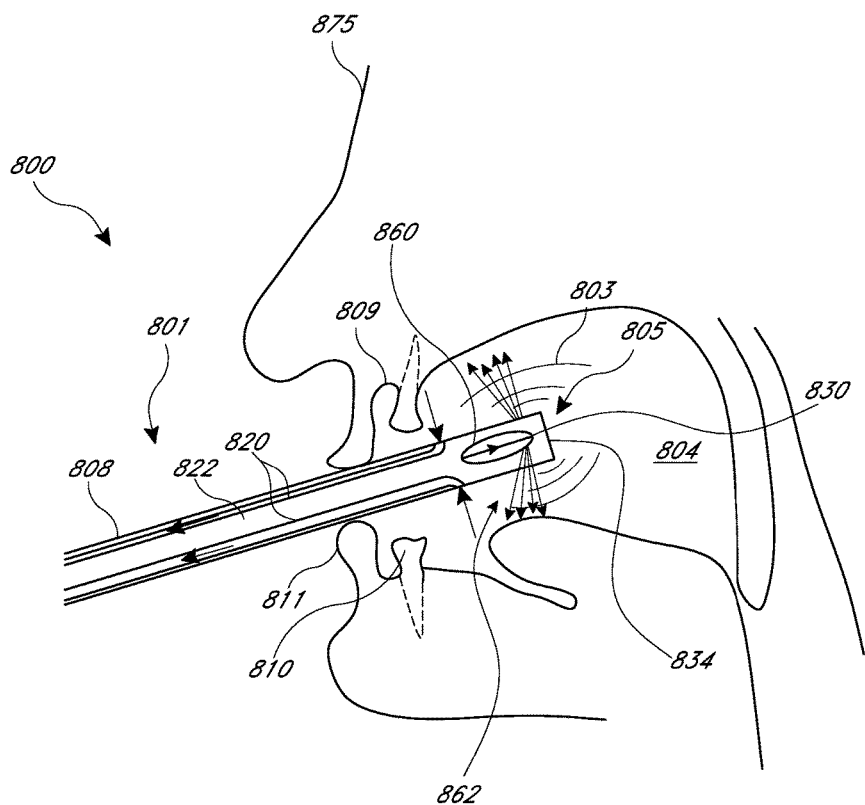
FIG. 8 is a schematic side view of a dental apparatus comprising a fluid platform having a liquid jet device configured to be inserted into a mouth of a user to substantially clean dental deposits from teeth and gums.

FIG. 8 is a schematic side view of a dental system 800 comprising a mouthpiece 801 having an energy outlet 805 configured to be inserted into a mouth 804 of a user 875 to clean dental deposits from the user's teeth 810, gums 809, and/or other surfaces of the mouth 804. In FIG. 8, reference numerals similar to those of FIGS. 7A-7B have been used to designate similar components and have been incremented by 100 relative to FIGS. 7A-7B. The foregoing description of those components should apply to the components of FIG. 8, unless otherwise noted. For example, as with FIGS. 7A-7B, the mouthpiece 801 of FIG. 8 may include a handpiece 808, an energy outlet 805 that can act as a pressure wave generator and/or a fluid motion source, a fluid inlet line 822, and a fluid outlet line 820. In the embodiment of FIG. 8, for example, the energy outlet 805 comprises a liquid jet device.

As with FIGS. 7A-7B, a distal portion of the energy outlet 805 can be inserted into the user's mouth 804, and the user 875 can enclose his or her lips 811 about a portion of the handpiece 808 to seal the mouth 804 around the handpiece 808. In some embodiments, at least some treatment fluid can be supplied to the mouth 804 before activating the energy outlet 805 to at least partially fill the mouth 804. In other embodiments, no treatment fluid can be supplied before activating the energy outlet 805.

The user can activate the system 800, and treatment liquid 862 can pass through the inlet line 822. As explained above, a liquid jet 830 can be formed by passing high-pressure liquid through an orifice in the handpiece 808. The jet 830 can pass through the inlet line 822 (which can pass along a channel of a guide tube) and can impact an impingement surface 834 disposed near a distal portion of the energy outlet 805. Pressure waves 803 can be generated when the jet 830 impacts the impingement surface 834. Furthermore, as explained above, treatment liquid 862 can be ejected or sprayed through an opening 860 near the distal portion of the energy outlet 805. As explained above with respect to, e.g., FIG. 7B, the fluid 862 that is sprayed or ejected through the opening 860 can improve fluid motion in the mouth 804. As above, waste fluid can be withdrawn from the mouth 804 through the fluid outlet lines 820.

In some embodiments, the user 875 can move the distal portion of the energy outlet 805 within the mouth 804, e.g., along surfaces of the teeth 810. In other embodiments, the user 875 can hold the energy outlet 805 still within the mouth 804. As explained above, the pressure waves 803 may propagate from the energy outlet 805 and couple to the teeth 810 and/or gums 809 to remove dental deposits. Furthermore, in some arrangements, the pressure waves 803 may propagate through the treatment fluid 862 that is ejected from the opening 860 and may couple to the teeth 810 and/or gums 809 to remove undesirable dental deposits. The treatment fluid 862 may enhance the cleaning by increasing the degree of fluid motion in the mouth 804 during the treatment procedure. Thus, as explained herein with respect to FIG. 8, the liquid jet device (e.g., the energy outlet 805) can advantageously act as a pressure wave generator, a fluid motion source, and an inlet for allowing the treatment fluid to enter the mouth 804.

Figure 8A:
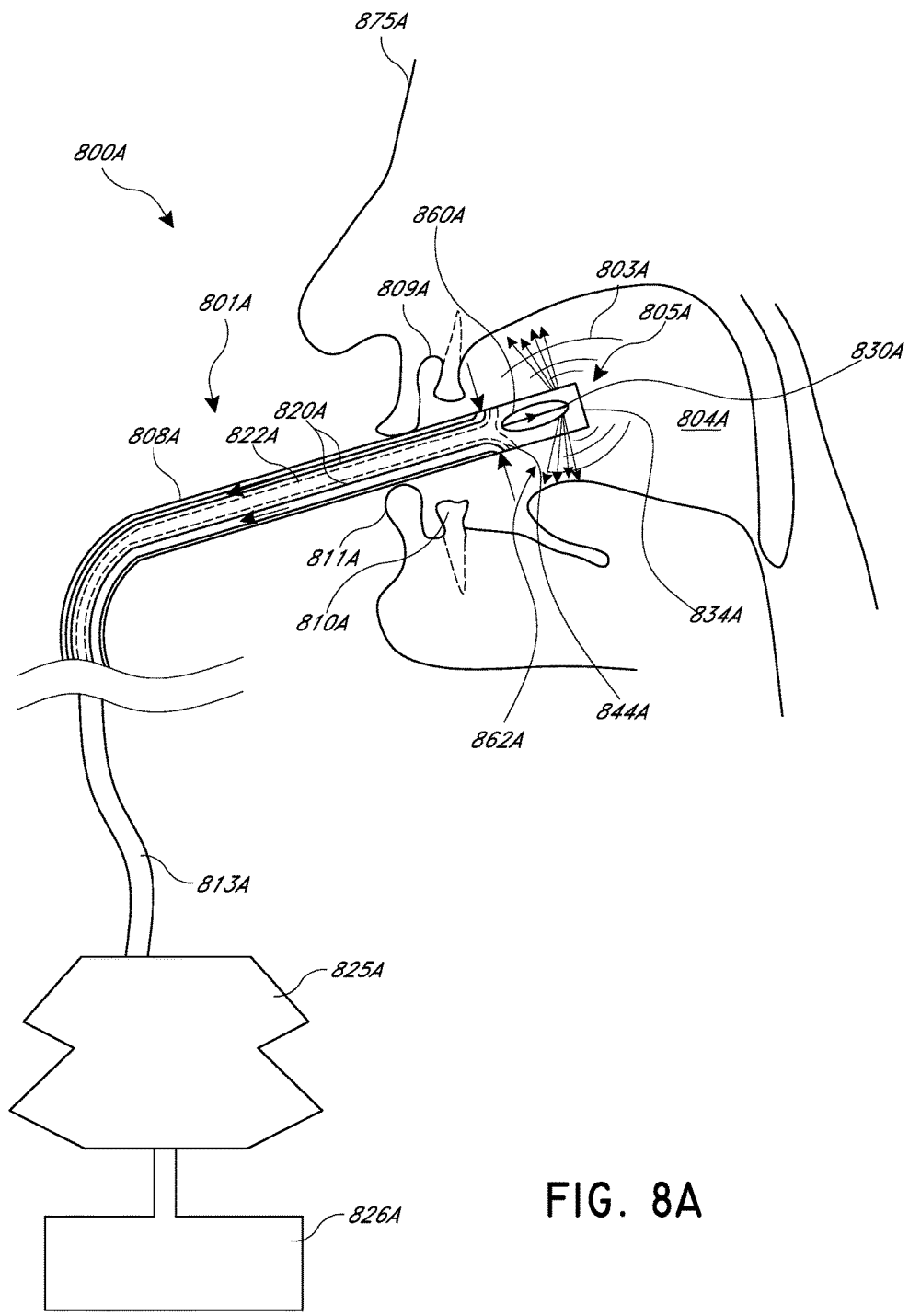
FIG. 8A is a schematic side view of a dental apparatus comprising a fluid platform, an active energy outlet and a pump configured to supply fluid to a mouth of a subject.

FIG. 8A is a schematic side view of a dental system 800A comprising a mouthpiece 801A having an energy outlet 805A configured to be inserted into a mouth 804A of a user 875A to clean dental deposits from the user's teeth 810A, gums 809A, and/or other surfaces of the mouth 804A. In FIG. 8A, reference numerals similar to those of FIG. 8 have been used to designate similar components and have been appended with the letter "A" relative to FIG. 8. The foregoing description of those components should apply to the components of FIG. 8A, unless otherwise noted. For example, as with FIG. 8, the mouthpiece 801A of FIG. 8A may include a handpiece 808A, an energy outlet 805A that can act as a pressure wave generator and/or a fluid motion source, a fluid inlet line 822A, and a fluid outlet line 820A. The fluid inlet line 822A can terminate at one or more fluid ports 844A. In the embodiment of FIG. 8A, for example, the energy outlet 805A comprises a liquid jet device. As with FIG. 8, the user 875A can close his or her lips about a distal portion of the energy outlet 805A and can activate the outlet 805A in the mouth 804A to substantially remove dental deposits from the teeth 810A and gums 809A.

In addition, FIG. 8A illustrates a pump 825A that is in fluid communication with the active energy outlet 805A by way of conduits 813A and ports 844A, which can transport fluid to and/or from the mouth 804A (e.g., at low volumetric movement) and the distal portion of the active energy outlet 805A. The pump 825A can be in communication with a control mechanism 826A which can be configured to control the operation of the pump 825A. The ports 844A can be large enough to supply relatively large volumes of treatment fluid to the mouth 804A. In some embodiments, the pump 825A can comprise a variable volume displacement pump, e.g., a bellow, or any other suitable pumping apparatus. The pump 825A can be in fluid communication with one or more fluid sources, e.g., fluid reservoirs. Alternatively, multiple pumps can be provided to pump fluid into the mouth 804A. The control mechanism 826A can operate the pump 825A. At the low frequency phase, the pump 826A operates at a low frequency, high displacement mode. In the high frequency phase, the pump 826A operates at a high frequency, low displacement mode. For example, the control mechanism 826A can operate the pump 825A (e.g., a bellow mechanism) to move the fluid in and out of the ports 844A in an oscillatory manner. The frequency of the oscillations may vary throughout the treatment. Advantageously, the ports 844A can allow for inflow and outflow of fluid to and from the mouth. In some arrangements, fluid can flow into and out of the same port, while in other arrangements, a particular port may be configured only for inflow or only for outflow. As explained herein, the control mechanism 826A can be configured to balance the amount of treatment liquid that flow into and out of the ports 844A.

In the system 800A of FIG. 8A, for example, the active energy outlet 805A can include a pressure wave generator (e.g., a liquid jet 830A and impingement member 834A) and a fluid motion source. The fluid motion source can comprise, e.g., the ports 844A, which in turn can be in fluid communication with the pump 825A by way of the conduits 813A. For example, treatment fluid can be supplied from one or more reservoirs and can be pumped through the conduits 813A and inlet line 822A by the pump 825A to the distal portion of the active energy outlet 805A. Treatment fluid 862A can exit the ports 844A and enter the mouth 804A. The ports 844A can be sized to allow relatively large volumes of fluid to enter the mouth 804A, which can generate large-scale fluid displacement. The pump 825A operation can vary both in terms of displacement as well as the frequency at which it operates.

As explained above, various treatment procedures can include one or more treatment phases. In each treatment phase, energy can be applied at a different frequency or band of frequencies. As explained above, the different frequencies can interact with the treatment fluid to clean dental deposits of varying sizes. For example, in some arrangements, lower frequency waves, or band of lower frequency waves, can remove relatively large dental deposits, and higher frequency waves, or band of higher frequency waves, can remove relatively small deposits, e.g., small deposits that may be formed in small spaces, cracks, crevices, irregular tooth surfaces, etc.

In the embodiment of FIG. 8A, for example, both the pressure wave generator (e.g., the liquid jet device) and the fluid motion source (e.g., the ports 844A which are in fluid communication with the pump 825A) can be operated in various frequency ranges. In a first example treatment procedure, a first low frequency phase may be activated and a second high frequency phase may be activated. In other embodiments, these phases can be performed substantially concurrently, or overlap. In this example, in the low frequency phase, the pressure wave generator can be inactivated, and the pump 825A may be activated at low frequencies. For example, the pump 825A may supply fluid through the inlet line 822A to the mouth 804A through the ports 844A at low frequencies to repeatedly move fluid in and out of the mouth to create low frequency and large volume fluid motion, while the pressure wave generator (e.g., jet device) is turned off. The low frequency action of the pump 825A may act to induce hydrodynamic motion in the treatment fluid and can generate large volumetric movement of fluid in the mouth 804A. Such low frequency, large volumetric fluid movement can act to remove relatively large dental deposits from the mouth 804A. In the second, high frequency phase, the pump 825A may be turned off, and the pressure wave generator (e.g., jet or other type of pressure wave generator) may be activated to produce relatively high frequencies. For example, the high frequency pressure waves generated by the pressure wave generator may act to remove relatively small deposits from small spaces, cracks, irregular surfaces, etc. The high frequency pressure waves may also induce small-scale volumetric movement of the fluid to assist the cleaning procedure.

In a second example treatment procedure, a first low frequency phase can be activated and a second high frequency phase can be activated. In some embodiments, these phases can be performed sequentially. In other embodiments, these phases can be performed substantially concurrently, or overlap. In this example, as with the first example procedure, in the low frequency phase, the pump 825A (which can be in fluid communication with a fluid motion source, such as ports 844A) may be activated, while the pressure wave generator is inactivated. As with the first example, the low frequency fluid motion may induce large-volume fluid movement to clean large deposits from the mouth 804A. However, unlike the first example, in the second example, the high frequency phase can be activated by activating both the pump 825A and the pressure wave generator (e.g., the liquid jet device). For example, in the high frequency phase of the second example, the pump 825A can supply fluid into and out of the mouth, and the pressure wave generator can generate relatively high frequency pressure waves in the treatment fluid. The high frequency pressure waves and the low volumetric fluid movement can act to remove relatively small deposits from the mouth 804A, e.g., small deposits and debris from small spaces, cracks, irregular surfaces, etc. Unlike the low frequency phase, in the high frequency phase of the second example, the amount of fluid displacement in the mouth 804A may be smaller than in the low frequency phase of the first example. Still, the fluid movement during the high frequency phase may assist in removing the undesirable dental deposits from the mouth 804A.

In a third example treatment procedure, a first, low frequency phase can be activated, and a second, high frequency phase can be activated. Unlike the first and second examples, however, in the low frequency phase of the third example, both the pump 825A (e.g., fluid motion source) and the pressure wave generator may both be activated at low frequencies. The large-scale fluid displacement generated by the pump 825A can act to induce large-volumetric fluid motion to remove large deposits. In the high frequency phase of the third example, as with high frequency phase of the second example, both the pump 825A (which can be in fluid communication with a fluid motion source, such as ports 844A) and the liquid jet 830A (e.g., pressure wave generator) may be activated at high frequencies to remove small deposits.

In a fourth example treatment procedure, a first, low frequency phase can be activated, and a second, high frequency phase can be activated. Unlike the first, second, and third treatment examples, however, only the pump 825A may be used to generate fluid movement in the treatment liquid, e.g., there need not be a separate pressure wave generator. For example, the pump 825A (which may be a bellow-type device), can include one or more moving elements that provide movement of the fluid into and out of the mouth in an oscillatory manner. In the low frequency phase, for example, the pump 825A may supply fluid through the inlet line 822A to the mouth 804A through the ports 844A at low frequencies to repeatedly move fluid in and out of the mouth to create low frequency and large volume fluid motion. The low frequency action of the pump 825A may act to induce hydrodynamic motion in the treatment fluid and can generate large volumetric movement of fluid in the mouth 804A. Such low frequency, large volumetric fluid movement can act to remove relatively large dental deposits from the mouth 804A. In the high frequency phase, the pump 825A may be activated at high frequencies to produce pressure waves in the treatment fluid at a correspondingly high frequency, and such pressure waves will propagate through the inlet line 822A into the mouth 804A. The high frequency pressure waves can remove relatively small deposits from the mouth 804A, e.g., small deposits and debris from small spaces, cracks, irregular surfaces, etc. The controller 826A can operate the pump 825A. At the low frequency phase, the pump 826A operates at a low frequency, high displacement mode. In the high frequency phase, the pump 826A operates at a high frequency, low displacement mode. As explained above, the amount of treatment liquid in the user's mouth during the treatment procedure (e.g., during a cleaning phase at any suitable frequency range and flow rate) can be balanced, e.g., the amount of inflow and outflow can be maintained to be about equal.

Further, it should be appreciated that while the pressure wave generator of FIG. 8A includes a liquid jet device, the treatment procedures and apparatus disclosed with respect to FIG. 8A may also be suitable with other types of pressure wave generators. In addition, although the examples described above describe two phases (e.g., high and low frequency phases), as explained above, a treatment procedure can include any number of intermediate frequency phases to assist in cleaning the deposits from the mouth. Further, the treatment procedure can include multiple sequences of the low and high frequency phases. For example, one procedure could activate a low frequency phase, a high frequency phase, a low frequency phase, a high frequency phase, and a low frequency phase.

Figure 8B:
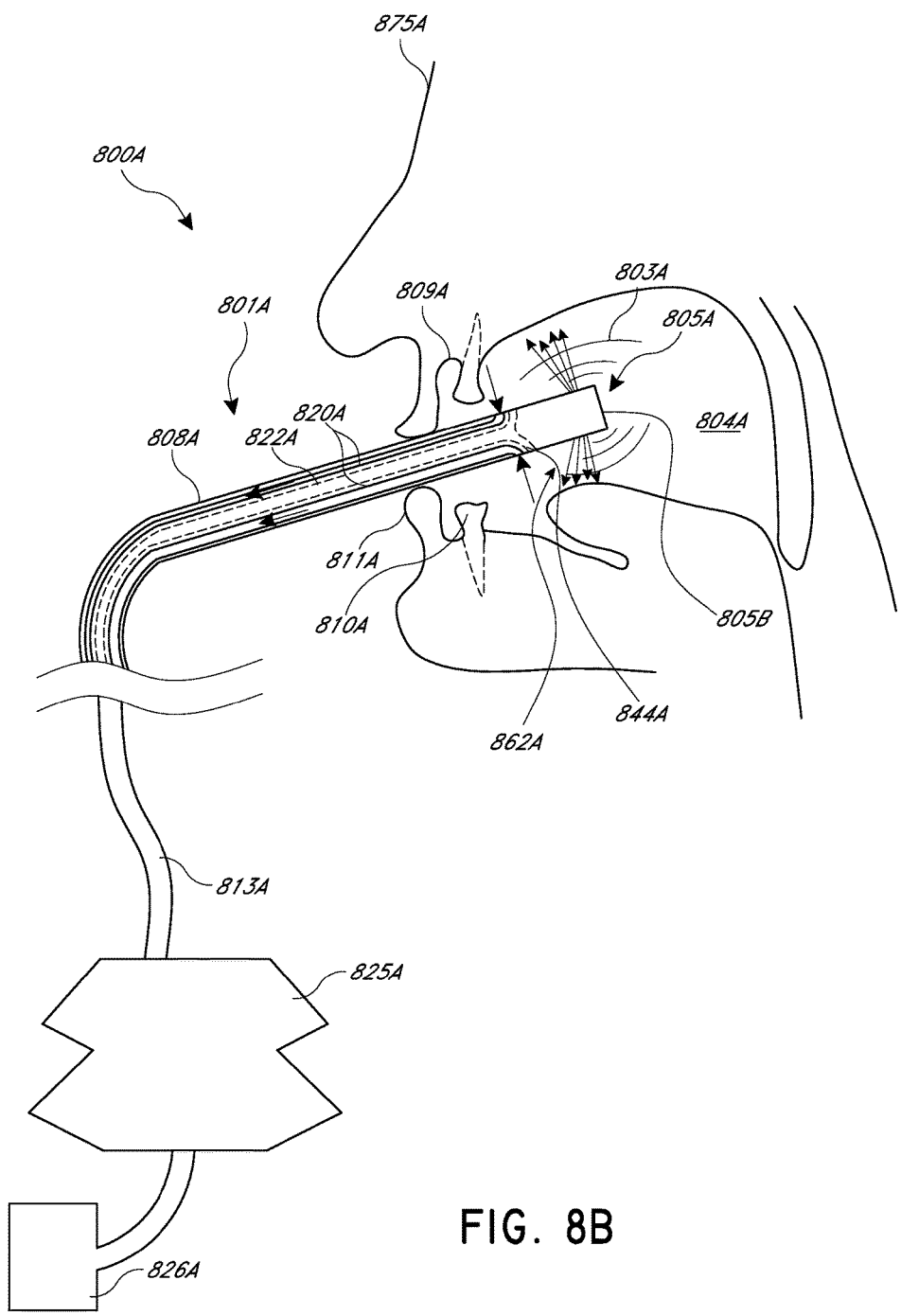
FIG. 8B is a schematic side view of a dental apparatus according to various embodiments.

For example, FIG. 8B illustrates another embodiment of a system 800A, which is similar to the embodiment of FIG. 8A. In FIG. 8B, reference numerals similar to those of FIG. 8A have been used to designate similar components. The foregoing description of those components should apply to the components of FIG. 8B, unless otherwise noted. For example, the active energy outlet 805A can include a pressure wave generator 805B and a fluid motion source, e.g., fluid ports 844A, which can be in fluid communication with a pump 825A. As illustrated in FIG. 8B, the pressure wave generator 805B can be any suitable pressure wave generator as described in detail herein. The pump 825A can be in communication with a control mechanism 826A which can be configured to control the operation of the pump 825A. The pump 825A operation can vary both in terms of displacement as well as the frequency at which it operates. As with FIG. 8A, both the pressure wave generator 805B and the fluid motion source (e.g., the ports 844A, which can be in fluid communication with the pump 825A) can be operated in various frequency ranges. The pressure wave generator 805B and the pump 825A can operate at high, low, and intermediate frequencies. As explained above, the various treatment procedures can include one or more treatment phases operating at various frequencies. Further, as explained herein, the amount of treatment liquid in the user's mouth during the treatment procedure (e.g., during a cleaning phase at any suitable frequency range and flow rate) can be balanced, e.g., the amount of inflow and outflow can be maintained to be about equal. Advantageously, the ports 844A can allow for inflow and outflow of fluid to and from the mouth. In some arrangements, fluid can flow into and out of the same port, while in other arrangements, a particular port may be configured only for inflow or only for outflow. As explained herein, the control mechanism 826A can be configured to balance the amount of treatment liquid that flow into and out of the ports 844A.

Figure 8D:
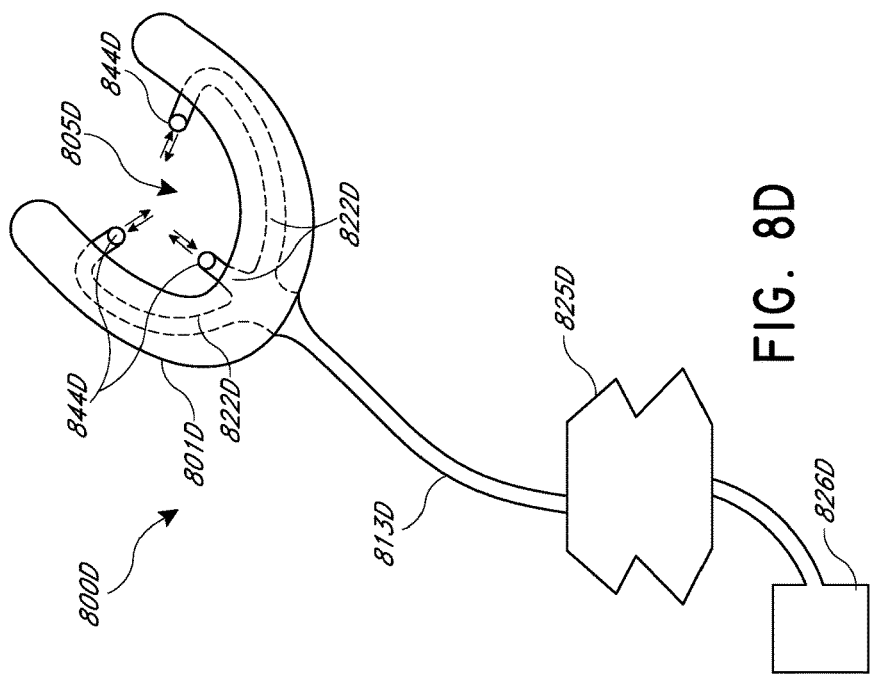
FIG. 8D is a schematic perspective view of a dental system, in accordance with yet another embodiment.
Figure 8C:
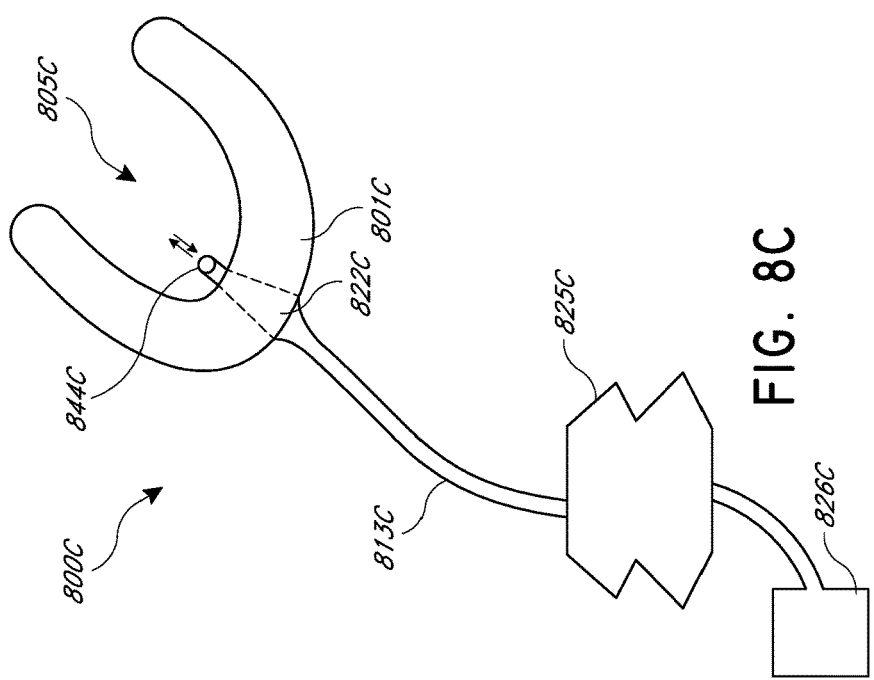
FIG. 8C is a schematic perspective view of a dental system, in accordance with an additional embodiment.

With reference to FIG. 8C, another embodiment of a dental system 800C is illustrated. In FIG. 8C, reference numerals similar to those of FIGS. 8A-8B have been used to designate similar components and have been appended with the letter "C" relative to FIGS. 8A-8B. The foregoing description of those components should apply to the components of FIG. 8C, unless otherwise noted. The dental system 800C can include an active energy outlet 805C and a mouthpiece 801C sized and shaped to be inserted into a mouth of a subject. As shown in FIG. 8C, for example, the mouthpiece 801C is shaped to substantially conform to a maxillary or a mandibular arch of a mammal. In particular, the mouthpiece 801C can be shaped to conform to a bottom row of teeth and/or a top row of teeth.

The active energy outlet 805C can be incorporated into the mouthpiece 801C in the embodiment of FIG. 8C. For example, as with the embodiments of FIGS. 8A-8B, the active energy outlet 805C can comprise a fluid motion source that includes one or more fluid ports 844C. In FIG. 8C, a single port 844C is provided to supply relatively large volumes of fluid, e.g., treatment liquid, to the mouth, although in other embodiments, any suitable number of ports may be provided. The port 844C can be in fluid communication with a fluid delivery line 822C disposed on, in, or near the mouthpiece 801C. The fluid delivery line 822C can in turn be in fluid communication with a pump 825C by way of one or more conduits 813C. A control mechanism 826C can be configured to control the operation of the pump 825C. As in the embodiments of FIGS. 8A-8B, for example, the pump 825C can be a bellows-type pump in various arrangements.

During a treatment procedure, the control mechanism 826C can cause the pump 825C to deliver fluid to or from the mouthpiece 801C by way of the one or more conduits 813C. For example, the fluid delivery line 822C can be formed within the interior of the mouthpiece 801C and can fluidly communicate with the one or more conduits 813C. The fluid delivery line 822C can deliver fluid from the conduits 813C to and/or from the mouth through the port 844C. As shown in FIG. 8C, for example, the mouthpiece 801C can include the single port 844C disposed near a central portion of the mouthpiece 801C. In FIG. 8C, for example, the mouthpiece 801C can be substantially symmetric about a central axis, and the port 844C can be located along or near that central axis. Thus, in the embodiment of FIG. 8C, the control mechanism 826C and the pump 825C can deliver fluid through the conduits 813C to the mouthpiece 801C. The fluid delivery line 822C of the mouthpiece 801C can deliver treatment fluid to and/or from the mouth by way of the port 844C.

Although the port 844C is illustrated in FIG. 8C as extending past a curved, concave portion of the mouthpiece 801C, the port 844C can instead be formed through or near any other suitable surface of the mouthpiece 801C. For example, in some embodiments, the port 844C can be disposed on a top or bottom surface of the mouthpiece 801C. In various embodiments, the mouthpiece 801C can include one or more walls extending from a central surface, e.g., similar to the mouthpiece 1101 illustrated in FIGS. 11A-11D and/or the mouthpiece 1201 illustrated in FIGS. 12A-12B, explained in more detail below. As an example, two walls can extend upwards from the central surface and can be spaced apart by a separation distance sufficient to receive one of more teeth between the two upwardly-extending walls (e.g., to receive teeth in an upper row of teeth). Two walls can also extend downwards from the central surface and can be spaced apart by a separation distance sufficient to receive one of more teeth between the two downwardly-extending walls (e.g., to receive teeth in a lower row of teeth). In such embodiments, the port 844A can be formed through the wall(s) and/or through the central surface. The mouthpiece 801C can be shaped to loosely fit in the mouth in some embodiments, e.g., such that a space can be maintained between the port 844C and mouth surfaces. For example, the mouthpiece 801C can be shaped to provide separation between the port 844C and the teeth and/or gums so as to prevent the teeth and/or gums from occluding the port 844C.

In some embodiments, a first wall can extend upwards from a front portion of the mouthpiece 801C, and a second wall can extend downwards from the front portion of the mouthpiece 801C. One or more ports can be formed in the first and second walls to deliver fluid to and from the mouth. The user can bite or rest her teeth on or adjacent a back portion of the mouthpiece 801C to provide separation between the port(s) and front surfaces of the user's teeth and/or gums. The ports in the walls can deliver fluid to and from the mouth to clean front surfaces of the user's teeth and/or gums, and/or surfaces between adjacent teeth.

In some embodiments, a first wall can extend upwards from a back portion of the mouthpiece 801C, and a second wall can extend downwards from the back portion of the mouthpiece 801C. One or more ports can be formed in the first and second walls to deliver fluid to and from the mouth. The user can bite or rest her teeth on or adjacent a front portion of the mouthpiece 801C to provide separation between the port(s) and back surfaces of the user's teeth and/or gums. The ports in the walls can deliver fluid to and from the mouth to clean back surfaces of the user's teeth and/or gums, and/or surfaces between adjacent teeth. Although some embodiments described herein contemplate a wall extending upwardly and a wall extending downwardly from the mouthpiece, in other embodiments, a single wall can extend from the mouthpiece and can be used on either a top row of teeth or a bottom row of teeth.

It should be appreciated that the port 844C may be disposed at any suitable location on or near the mouthpiece 801C. For example, the port 844C can be positioned to direct liquid directly against a surface of the teeth and/or gums. In other arrangements, the port 844C can be positioned to direct liquid into other portions of the oral cavity, e.g., behind the teeth, and the fluid motion and/or pressure waves can act to clean the teeth. In some arrangements, the mouthpiece 801C can be formed as a unitary structure. For example, the mouthpiece 801C can be formed of an elastic or plastic material, such as any suitable biocompatible polymer.

The active energy outlet 805C can be activated by a user of the system 800C. In some embodiments, the user can activate the active energy outlet 805C to initiate the cleaning procedure by biting the mouthpiece 801C to engage a switch formed in or coupled to the mouthpiece 801C. In other embodiments, the user can activate the fluid motion source to initiate cleaning by manually engaging a switch outside the mouth, e.g., on an external user console or on the control mechanism 826C. In some embodiments, the user can switch between treatment phases, e.g., the user can vary the frequency of the oscillatory fluid movement. In other embodiments, the control mechanism 826C can automatically vary the frequency of the oscillatory fluid movement.

In some embodiments, the control mechanism 826C can be configured to generate oscillatory pressures and oscillatory movement of fluid to and from the mouth through the port 844C at variable frequencies. Thus, fluid can be delivered to the mouth through the port 844C and can be removed from the mouth through port 844C in a cycle having a frequency that can vary during the treatment procedure. As explained above with respect to the embodiments of FIGS. 8A-8B, the system 800C of FIG. 8C can be used to clean teeth and/or gums in one or more treatment phases. For example, the system 800C of FIG. 8C can be configured to perform the fourth example treatment procedure described above with respect to FIG. 8A, e.g., the example procedure in which only the pump 825A is used to provide the low- and high-frequency phases. Thus, in FIG. 8C, there need not be a pressure wave generator separate from the pump 825C. During a treatment procedure, the active energy outlet 805C (e.g., the fluid motion source such as port 844C) can be configured to create oscillatory movement of fluid to and from the mouth at a first frequency range during a first treatment phase and at a second frequency range during a second treatment phase. In some embodiments, the second frequency range can include frequencies that are higher than the frequencies in the first frequency range. For example, the first frequency range can include frequencies in a range of about 0.1 Hz to about 20 KHz. The second frequency range can include frequencies in a range of about 20 KHz to about 1,000 KHz.

As explained above, in various embodiments, the treatment phases can be performed sequentially. For example, the first treatment phase at the first frequency range can be performed, and the second treatment phase at the second frequency range can be performed after the first treatment phase, or vice versa. At the lower frequencies (e.g., in the first treatment phase in this example), a larger volume of fluid can move to and from the mouth, and at the higher frequencies of oscillation (e.g., in the second treatment phase in this example), a smaller volume of fluid can move to and from the mouth. The large-scale volumetric fluid movement at lower frequencies may act to clean larger dental deposits and debris, while the smaller-scale volumetric fluid movement at higher frequencies may act to clean smaller dental deposits and debris, such as deposits within small spaces, cracks, crevices, irregular surfaces, etc. In the embodiment of FIG. 8C, moreover, degassed liquid can be used as the treatment fluid to enhance the cleaning of the teeth and/or gums.

In some embodiments, the control mechanism 826C can be configured to create oscillatory movement of fluid to and from the mouth at frequencies that increase over time from a first frequency in the first frequency range to a second frequency in the second frequency range. Thus, in some arrangements, the frequency of oscillation of the volumetric fluid movement can continuously increase as the procedure progresses. In some embodiments, however, the treatment phases can at least partially overlap. In addition, in some embodiments, the control mechanism 826C can be configured to randomly change the frequencies of the oscillatory movement of fluid to and from the mouth to enhance cleaning. The amount of treatment liquid in the user's mouth during the treatment procedure (e.g., during a cleaning phase at any suitable frequency range and flow rate) can be balanced, e.g., the amount of inflow and outflow can be maintained to be about equal. Advantageously, the port 844C can allow for inflow and/or outflow of fluid to and from the mouth. In some arrangements, fluid can flow into and out of the same port, while in other arrangements, a particular port may be configured only for inflow or only for outflow. As explained herein, the control mechanism 826C can be configured to balance the amount of treatment liquid that flows into and out of the port 844C.

FIG. 8D illustrates a dental system 800D similar to the system 800C of FIG. 8C. In FIG. 8D, reference numerals similar to those of FIG. 8C have been used to designate similar components and have been appended with the letter "D" relative to FIG. 8C. The foregoing description of those components should apply to the components of FIG. 8D, unless otherwise noted. For example, as with FIG. 8C, the system 800D of FIG. 8D can include a mouthpiece 801D and an active energy outlet 805D. The active energy outlet 805D can comprise a fluid motion source that includes a plurality of ports 844D that are in fluid communication with a pump 825D by way of multiple fluid delivery lines 822D and one or more fluid conduits 813D. A control mechanism 826D can be configured to control the operation of the pump 825D. The one or more conduits 813D can provide fluid communication between the pump 825D and the mouthpiece 801D, and the fluid delivery lines 822D can provide fluid communication between the conduits 813D and the ports 844D.

Unlike the system 800C of FIG. 8C, multiple fluid delivery lines 822D are disposed on, in, or near the mouthpiece 801D in FIG. 8D, as opposed to the single delivery line 822C illustrated in FIG. 8C. In particular, three fluid delivery lines 822D provide fluid communication between the conduits 813D and three corresponding fluid ports 844D. As shown in FIG. 8D, for example, a central delivery line can be disposed near a central portion of the mouthpiece 801D, and two auxiliary delivery lines can be disposed near respective side portions of the mouthpiece 801D. Thus, as illustrated in FIG. 8D, the three fluid ports 844D are spaced apart from and angled relative to one another. In such arrangements, it can be advantageous to deliver fluid to and from the mouth at different orientations to enhance the cleaning of the teeth and/or gums. In other embodiments, any other suitable number of ports 844D can be used. For example, two ports 844D can be used, or more than three ports 844D can be used.

As with FIG. 8C, the control mechanism 826D can be configured to create oscillatory movement of fluid to and from the mouth through the ports 844D at variable frequencies. Thus, fluid can be delivered to the mouth through the ports 844D and can be removed from the mouth through the ports 844D in a cycle having a frequency that can vary during the treatment procedure. As above, one or more treatment phases can be performed by varying the frequency of the oscillatory fluid movement. For example, low-frequency, high-volume fluid movement can be effective at cleaning relatively large dental deposits and debris, and high-frequency, low-volume fluid movement can be effective at cleaning relatively small dental deposits and debris. As above, the amount of treatment liquid in the user's mouth during the treatment procedure (e.g., during a cleaning phase at any suitable frequency range and flow rate) can be balanced, e.g., the amount of inflow and outflow can be maintained to be about equal. Advantageously, the ports 844D can allow for inflow and outflow of fluid to and from the mouth. In some arrangements, fluid can flow into and out of the same port, while in other arrangements, a particular port may be configured only for inflow or only for outflow. As explained herein, the control mechanism 826D can be configured to balance the amount of treatment liquid that flow into and out of the port 844D.

FIG. 9 is a schematic side view of a mouthpiece 901 configured to be inserted into a mouth of a user to clean deposits from teeth, gums, and other surfaces of the mouth. In particular, the mouthpiece 901 illustrated in FIG. 9 may be used in accordance with the embodiments disclosed above in FIGS. 7A, 7B, and 8-8D. In particular, the mouthpiece 901 can include a handpiece 908, a fluid inlet line 922, a fluid outlet line 920, an energy outlet 905, and an energy conduit 963 configured to convey energy to the energy outlet 905. As explained above with respect to FIGS. 7A-8D, a user can enclose his or her lips about the handpiece 908. The energy outlet 905 can be activated to clean dental deposits from the teeth, gums, and other surfaces in the mouth. The energy outlet 905 can comprise any suitable energy outlet, such as a pressure wave generator, a fluid motion source, an active fluid inlet, etc. For example, in various embodiments, the energy outlet 905 can comprise a liquid jet device, a laser, liquid streams, a piezoelectric transducer, etc.

FIGS. 10A-10D are schematic side views of various types of fluid platforms that can be used in accordance with the embodiment illustrated in FIG. 9. For example, FIG. 10A illustrates a mouthpiece 1001 that includes a handpiece 1008, an energy outlet 1005, an energy conduit 1063, a fluid inlet line 1022, and a fluid outlet line 1020. As shown in FIG. 10A, treatment liquid passing along the inlet line 1022 can enter the user's mouth by way of an inlet opening 1023.

Waste fluid can enter the outlet line 1020 by way of an outlet opening 1021. Treatment fluid entering the mouth can at least partially fill the mouth in some embodiments. Furthermore, the liquid that enters the mouth can also be able to pass through an opening 1060 disposed near a distal portion of the energy outlet 1005.

In the embodiment of FIG. 10A, the energy outlet 1005 can be configured to form a laser beam 1031. For example, the energy conduit 1063 can supply energy to the handpiece 1008, which can generate the laser beam 1031 using any suitable method known to those having skill in the art. The laser beam 1031 can impinge on a distal portion of the energy outlet 1005 and can interact with the treatment liquid passing through an opening 1060 in the energy outlet 1005. The laser beam 1031 may thereby act as a pressure wave generator and can generate pressure waves sufficient to induce fluid cavitation near the teeth and/or gums to be treated to remove dental deposits from the mouth. The mouthpiece 1001 can also include a fluid motion source (not shown) in addition to the inlet line 1022 and outlet line 1020.

As with FIG. 10A, FIG. 10B illustrates a mouthpiece 1001A that includes a handpiece 1008A, an energy outlet 1005A, a fluid inlet line 1022A, a fluid outlet line 1020A, and an outlet opening 1021A. Unlike the embodiment of FIG. 10A, however, the energy outlet 1005A can be configured to form a plurality of liquid streams 1062 that can pass through one or more liquid inlet openings 1023A. The liquid streams 1062 can be formed under high fluid pressure and can be used to generate pressure waves in the mouth, to induce fluid motion in the mouth, and/or to inject treatment fluid in the mouth. As with FIG. 10A, the outlet opening 1021A can receive waste fluid, which can pass along the fluid outlet line 1020A.

Turning to FIG. 10C, a mouthpiece 1001B can include a handpiece 1008B, an energy outlet 1005B, a fluid inlet line 1022B, a fluid outlet line 1020B, and an outlet opening 1021B. Unlike FIGS. 10A-10B, however, the energy outlet 1005B of FIG. 10C can be configured to form a liquid jet 1030. For example, as explained above, high-pressure liquid can pass through an orifice in the handpiece 1008B to form a coherent, collimated liquid jet. The jet 1030 can pass along a channel of a guide tube or handpiece 1008B and can impact an impingement surface 1034 near a distal portion of the energy outlet 1005B. As explained herein, when the jet 1030 impacts the impingement surface 1034, pressure waves can be generated. Furthermore, an opening 1060B can be disposed near the distal portion of the energy outlet 1005B. Treatment liquid 1062B that impacts the impingement surface 1034 can exit the handpiece 1008B through the opening 1060B. As above, when the treatment liquid 1062B is ejected or sprayed through the opening 1060B and into the mouth, fluid motion in the mouth may be enhanced, which can improve the cleaning process in some arrangements. Thus, the energy outlet 1005B (e.g., a liquid jet device) may act as a pressure wave generator, a fluid motion source, and/or an active fluid inlet.

FIG. 10D illustrates a mouthpiece 1001C that includes a handpiece 1008C, an energy outlet 1005C, a fluid inlet line 1022C, a fluid outlet line 1020C, an outlet opening 1021C, and an inlet opening 1023C. In addition, an opening 1060C can be provided near a distal portion of the energy outlet 1005C. Unlike the embodiments of FIGS. 10A-10C, however, the energy outlet 1005C of FIG. 10D includes a vibrating object 1064 disposed near the distal portion of the energy outlet 1005C. For example, in some embodiments, the vibrating object 1064 can be an ultrasonic tip, a piezoelectric transducer, a mechanical stirrer, etc. The vibrating object 1064 can act as a pressure wave generator configured to generate pressure waves sufficient to remove dental deposits from the user's teeth and/or gums. In addition, as explained herein, the mouthpiece 1001C can also include a fluid motion source, in addition to the inlet line 1022C and outlet line 1020C.

Figure 11A:
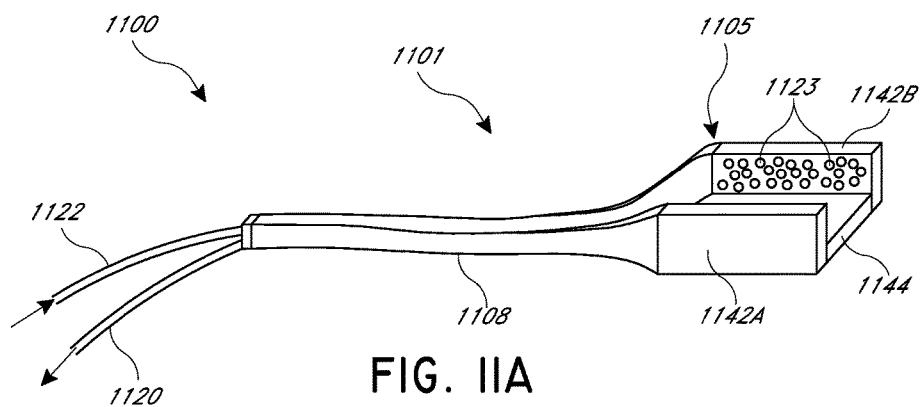
FIGS. 11A-11D illustrate a dental apparatus configured to remove undesirable dental deposits from a user's mouth, according to another embodiment.
Figure 11C:
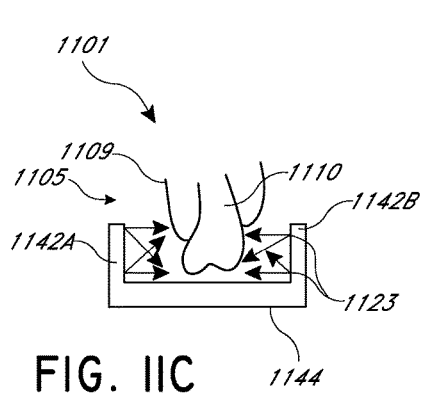
Figure 11D:
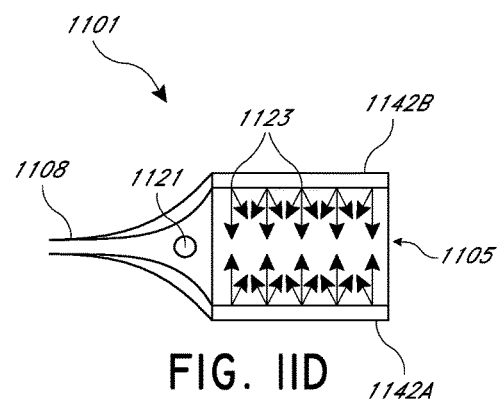
Figure 11B:
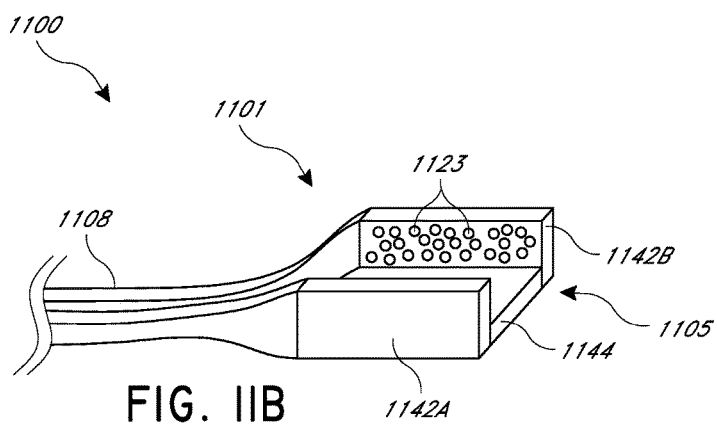

FIGS. 11A-11D illustrate a dental system 1100 configured to remove undesirable dental deposits from a user's mouth, including cleaning stains, calculus, caries, biofilms, etc. from the teeth and/or gums, and removing deposits from the gingival sulcus and periodontal pockets. In particular, FIG. 11A is a three-dimensional perspective view of the dental system 1100. FIG. 11B is a magnified perspective view of the system 1100 shown in FIG. 11A. FIG. 11C is a schematic front view of a mouthpiece 1101 configured for use with the apparatus 1100, and FIG. 11D is a top plan view of the mouthpiece 1101 of FIG. 11C.

The system 1100 of FIGS. 11A-11D can include the mouthpiece 1101, a fluid inlet line 1122, and a fluid outlet line 1120, a handpiece 1108 and an active energy outlet 1105 (e.g., a pressure wave generator) disposed near a distal portion of the handpiece 1108. The active energy outlet 1105 can include a first plate 1142A and a second plate 1142B spaced apart from the first plate 1142A. Although the first and second plates 1142A, 1142B of FIGS. 11A-11D are illustrated as being substantially planar, it should be appreciated that the plates 1142A, 1142B can be any suitable shape, and can be curved to fit a portion of the mouth to be treated. The first and second plates 1142A, 1142B can be coupled by a connector 1144. The connector 1144 can mechanically couple the first and second plates 1142A, 1142B and can physically separate the plates 1142A, 1142B by a separation distance. The separation distance can be larger than at least a width of a tooth to be treated. Each of the plates 1142A, 1142B can include a plurality of orifices 1123 sized and shaped to eject liquid. For example, liquid passing through the inlet line 1122 can flow to the active energy outlet 1105 under high pressure and can be ejected through the orifices 1123 as liquid jets. Thus, each orifice 1123 can be configured to form a liquid jet in some implementations.

The active energy outlet 1105 can be inserted into the mouth and can be sealed with the user's lips, as explained above with respect to FIGS. 7A-8D. In some embodiments, the system 1100 can at least partially, or substantially, fill the user's mouth with a treatment liquid. The user can position one or more teeth 1110 and/or portions of the gums 1109 between the first and second plates 1142A, 1142B. For example, the user can use the handpiece 1108 to manipulate the active energy outlet 1105 over the one or more teeth 1110 and gums 1109. For example, as shown in FIG. 11C, the first and second plates 1142A, 1142B can be applied near lingual and buccal surfaces of the tooth, respectively. The active energy outlet 1105 can be activated to emit energy from the orifices 1123. For example, in FIGS. 11A-11D, a liquid jet can be formed at each orifice 1123. The liquid jet may interact directly with the tooth 1110 and/or gums 1109 in some arrangements to clean the deposits from the tooth 1110 and/or gums 1109. For example, the jets may induce fluid motion (e.g., circulation, turbulence, etc.) which can help remove the deposits. In addition, the jets emitted from the orifices 1123 may generate pressure waves when the jets impact the tooth 1110, gums 1109, and/or another intervening impingement surface (not shown in FIGS. 11A-11D).

During the procedure, in some embodiments, an outlet opening 1121 can remove excess fluid from the mouth and convey the excess or waste fluid to the outlet line 1120, while maintaining the mouth substantially filled with treatment liquid. Thus, the system 1100 of FIGS. 11A-11D can generate sufficient pressure waves and/or induce sufficient fluid motion to at least partially or substantially remove dental deposits from a user's mouth, including cleaning stains, calculus, caries, and biofilms, and removing deposits from the gingival sulcus and periodontal pockets. Furthermore, although the active energy outlet 1105 of FIG. 11 includes a plurality of liquid jets, other pressure wave generators may be suitable. For example, pressure waves may be generated by energy emitted at the orifices 1123 using a plurality of vibrating objects, laser beams, etc. The mouthpiece 1101 of FIGS. 11A-11D can be used with any suitable treatment procedure disclosed herein, including, e.g., the procedures described above with respect to FIGS. 8 and 8A-8D. For example, for use with the procedures described in conjunction with FIGS. 8C-8D, the orifices 1123 can be used as the ports 844C/844D described above to deliver fluid to and from the mouth. As above, the fluid can be delivered to and from the mouth by way of the orifices 1123 in an oscillatory pattern that may vary during the procedure. Any suitable number of orifices 1123 may be used. For example, although numerous orifices 1123 are illustrated in FIGS. 11A-11D, only one, two, or three orifices 1123 may be used in various embodiments.

Figure 12A:
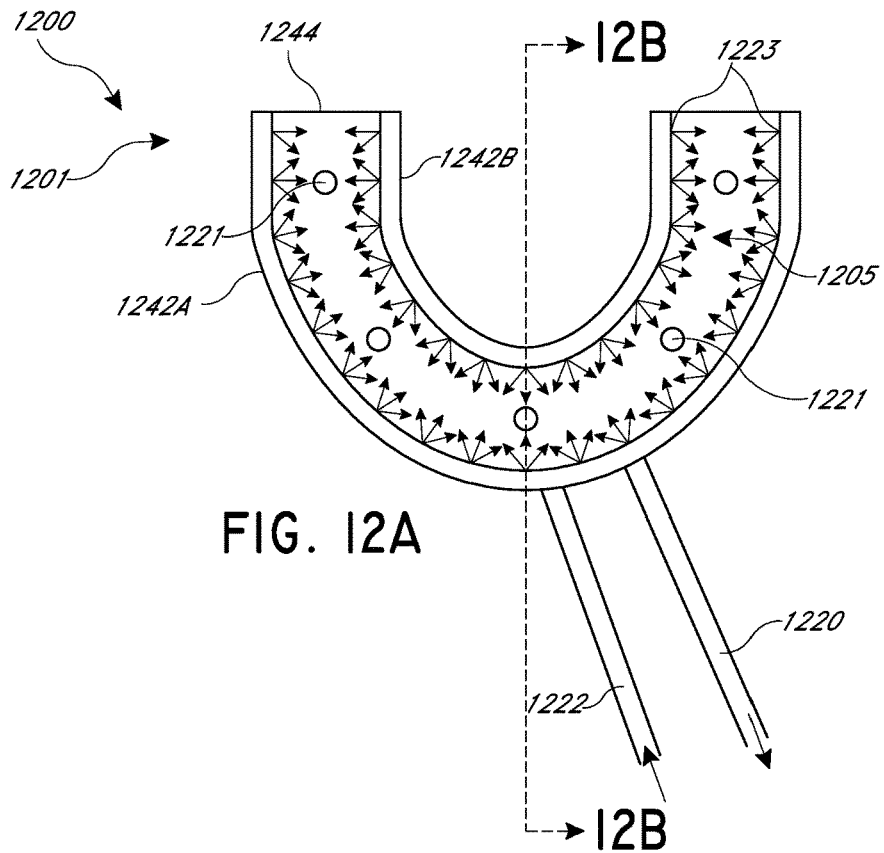
FIG. 12A is a top plan view of a dental apparatus configured to remove undesirable dental deposits from a user's mouth, according to yet another embodiment.
Figure 12B:
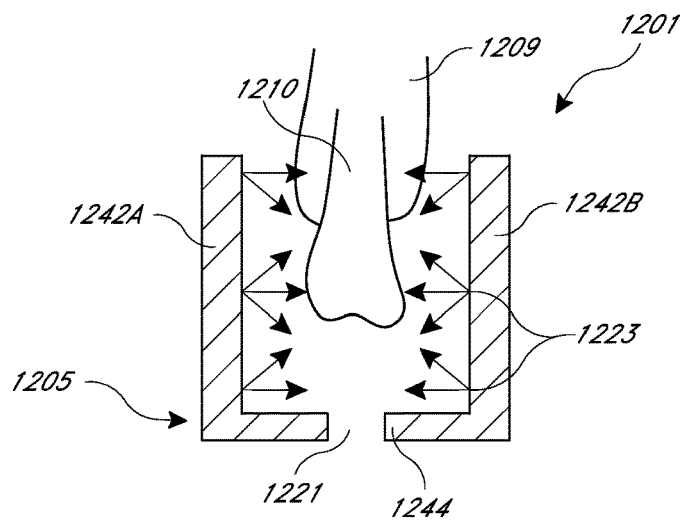
FIG. 12B is a side cross-sectional view of the apparatus of FIG. 12A, taken along line 12B-12B.

FIG. 12A is a top plan view of a dental system 1200 configured to remove undesirable dental deposits from a user's mouth. FIG. 12B is a side cross-sectional view of the system 1200 of FIG. 12A, taken along line 12B-12B. The apparatus 1200 can include a mouthpiece 1201 that comprises an active energy outlet 1205. As with the active energy outlet 1105 disclosed in FIGS. 11A-11D, the pressure wave generator 1205 of FIGS. 12A-12B can include a first plate 1242A and a second plate 1242B spaced apart from the first plate 1242A. A connector 1244 can couple the first and second plates 1242A, 1242B, and can separate the first and second plates 1242A, 1242B by a separation distance. A plurality of outlet openings 1221 can be provided in the connector 1244. Waste fluid can be withdrawn from the mouth by way of the outlet openings 1221, which can convey the waste fluid to a fluid outlet line 1220.

As in FIGS. 11A-11D, each plate 1242A, 1242B can include a plurality of orifices 1223. Treatment fluid can pass through a fluid inlet line 1222 at high pressures. When the liquid passes through the orifices 1223, a liquid jet can be formed at each orifice 1223. As explained above with reference to FIGS. 11A-11D, pressure waves generated by the liquid jets and/or enhanced fluid motion may clean dental deposits from one or more teeth 1210 and/or gums 1209.

Unlike the system 1100 of FIGS. 11A-11D, however, the active energy outlet 1205 of FIGS. 12A-12B can be shaped to conform to all or part of the maxillary or mandibular arch. Thus, the user or a clinician can place the mouthpiece 1201 over one or more teeth along the maxillary or mandibular arch. In some embodiments, for example, the mouthpiece 1201 can be applied over all the teeth along the top or bottom of the user's mouth. Upon activating the active energy outlet 1205, all the teeth that are disposed between the plates 1242A, 1242B can be substantially cleaned using the apparatus 1200 of FIGS. 12A-12B. Advantageously, the system 1200 of FIGS. 12A-12B can clean all the teeth on the top or bottom rows of teeth substantially simultaneously without requiring a toothbrush. The mouthpiece 1201 of FIGS. 12A-12B can be used with any suitable treatment procedure disclosed herein, including, e.g., the procedures described above with respect to FIGS. 8 and 8A-8D. For example, for use with the procedures described in conjunction with FIGS. 8C-8D, the orifices 1223 can be used as the ports 844C/844D described above to deliver fluid to and from the mouth. As above, the fluid can be delivered to and from the mouth by way of the orifices 1223 in an oscillatory pattern that may vary during the procedure. Any suitable number of orifices 1223 may be used. For example, although numerous orifices 1223 are illustrated in FIGS. 12A-12B, only one, two, or three orifices 1223 may be used in various embodiments.

VI. Treatment Solutions

The treatment solutions disclosed herein can be any suitable fluid, including, e.g., water, saline, etc. In some embodiments, the treatment solution can be degassed, which may improve cavitation and/or reduce the presence of gas bubbles in some treatments. In some embodiments, the dissolved gas content can be less than about 1% by volume. Various chemicals can be added to treatment solution, including, e.g., tissue dissolving agents (e.g., NaOCl), disinfectants (e.g., chlorhexidine), anesthesia, fluoride therapy agents, EDTA, citric acid, and any other suitable chemicals. For example, any other antibacterial, decalcifying, disinfecting, mineralizing, or whitening solutions may be used as well. Various solutions may be used in combination at the same time or sequentially at suitable concentrations. In some embodiments, chemicals and the concentrations of the chemicals can be varied throughout the procedure by the clinician and/or by the system to improve patient outcomes.

One example of a treatment solution comprises water or saline with 0.3% to 6% NaOCl. In some methods, tissue dissolution and dental deposit removal in the presence of NaOCl may not occur when the NaOCl concentration is less than 1%. In some treatment methods disclosed herein, tissue dissolution and dental deposit removal can occur at smaller (or much smaller) concentrations.

VII. Enhancing the Cleaning of Teeth and/or Gums

As explained above, a pressure wave generator can remove dental deposits by propagating pressure waves through a propagation medium to the treatment region, which can include one or more teeth and/or gums. Without being limited by theory, a few potential ways that the pressure waves clean undesirable dental deposits are presented below. Note that these principles, and the principles described above, may be generally applicable for each embodiment disclosed herein, e.g., each of the embodiments of FIGS. 1-12B.

Pressure waves generated by the pressure wave generator may interact with undesirable dental deposits, such as diseased and damaged hard tissue as well as soft tissues, food debris, dental calculus, plaque, biofilms, caries, and bacteria inside the mouth. The generated pressure waves can be tuned to have no or minimal (negligible) effect on healthy dentin and enamel. When the pressure waves remove the dental deposits and reach healthy dentin or enamel, the tissue removal action stops or slows down such that the healthy tooth matter is maintained. Thus, as compared with conventional mechanical treatments, the disclosed pressure wave generators can advantageously remove dental deposits in a non-invasive manner and without damaging healthy tooth matter.

In some arrangements, cavitation may be induced by the generated pressure waves. Upon irradiation of a liquid (e.g., water) with high intensity pressure waves (e.g., sound or ultrasound), acoustic cavitation may occur. The oscillation or the implosive collapse of small cavitation bubbles can produce localized effects, which may further enhance the cleaning process, e.g., by creating intense, small-scale localized heat, shock waves, and/or microjets and shear flows. Therefore, in some treatment methods, acoustic cavitation may be responsible for or involved in enhancing the chemical reaction, sonochemistry, sonoporation, soft tissue/cell/bacteria dissociation, delamination and breakup of biofilms.

For example, if the treatment liquid contains chemical(s) that act on the target dental deposits (e.g., stains, caries, dental calculs, plaque, bacteria, biofilms, etc.), the pressure waves (acoustic field) and/or the subsequent acoustic cavitation may enhance the chemical reaction via agitation and/or sonochemistry. Furthermore, sonoporation, which is the process of using pressure waves (e.g., acoustic field, ultrasonic frequencies) and/or the subsequent acoustic cavitation to modify the permeability of the bacterial cell plasma membrane, may also expedite the chemical reaction that removes the microorganisms from the tooth. It should also be appreciated that generated pressure waves, and/or the subsequent acoustic cavitation of certain frequencies, may result in cellular and bacterial rupture and death (e.g., lysis) as well as removal of decayed and weakened dentin and enamel. The cellular and bacterial rupture phenomenon may kill bacteria which might otherwise reinfect the gingival pockets and/or the oral cavity.

Generated pressure waves and/or the subsequent acoustic cavitation may also loosen the bond between the structure of the deposits (e.g., calculus, biofilm, caries, etc.), and/or the pressure waves may dissociate the deposits. In some cases, pressure waves and/or acoustic cavitation may loosen the bond between the cells and the dentin and/or delaminate the tissue from the tooth. Furthermore, the pressure waves and/or the subsequent acoustic cavitation may act on decayed hard tissue (which may be relatively weak and loosely connected) through vibrations and/or shock waves, and/or the microjets created as a result of cavitation bubble implosion, to remove decayed hard tissue from other healthy portions of the tooth.

Some properties can be adjusted or selected in various embodiments to enhance the cleaning process. For example, liquid properties such as, e.g., surface tension, boiling or vapor temperature, or saturation pressure can be adjusted or selected by the clinician to improve the cleaning process. Furthermore, the dissolved gas content of the treatment liquid can be adjusted or selected to reduce the energy loss of pressure waves that are created by hydrodynamic cavitation or other sources. As explained herein, for example, the treatment liquid can be degassed, which may help preserve the energy of the pressure waves and may increase the efficiency of the system.

In some arrangements, liquid circulation (e.g., convection) can enhance the cleaning of dental deposits from a diseased tooth. Due to relatively short time scales of the reaction process as compared to that of diffusion mechanisms, a faster mechanism of reactant delivery such as "macroscopic" liquid circulation may be advantageous in some of the embodiments disclosed herein. For example, liquid circulation with a time scale comparable to (and preferably faster than) that of chemical reaction may help replenish the reactants at the chemical reaction front and/or may help to remove the reaction byproducts from the reaction site. The convective time scale, which may relate to effectiveness of the convection process, can be adjusted and/or optimized depending on, e.g., the location and characteristics of the source of circulation. Furthermore, it should be appreciated that the introduction of liquid circulation generally does not eliminate the diffusion process, which may still remain effective within a thin microscopic layer at the chemical reaction front. Liquid circulation can also cause a strong irrigation in the treatment site (e.g. plaque inside the deep pocket) and may therefore result in loosening and/or removing larger pieces of debris (e.g. gingival plaque) from the treatment site.

In some arrangements, various properties can be adjusted to enhance liquid circulation, e.g., in the chamber of the cap. For example, the source of circulation relative to the location of the treatment site can be adjusted. The geometry of the space surrounding the source of circulation and treatment site can also be varied (e.g., to clean gingival deep pockets, etc.). It should also be appreciated that circulation may be affected by the viscosity of the treatment liquid and/or the mechanism of action of the source of circulation. For example, the circulation source, such as a jet of liquid ejected through the inlet opening, a stirrer such as a propeller or a vibrating object, etc., can be selected to enhance circulation of the treatment fluid. In some aspects, the input power of the source of liquid circulation can also be adjusted, such as the source of a pump that drives a liquid jet in some embodiments.

Various reaction chemistries can be adjusted or designed to improve the dental deposit cleaning process. For example, to enhance the dissolution of organic tissue, a tissue dissolving agent (e.g., a mineralization therapy agent, EDTA, sodium hypochlorite—NaOCl) can be added to the treatment liquid. The agent may react with various components at the treatment site. In some cases, tissue dissolution may be a multi-step process. The agent may dissolve, weaken, delaminate or dissociate organic and/or inorganic matter, which may result in better patient outcomes. The chemical reaction can modify the physical characteristics of the treatment solution locally (e.g., reducing the local surface tension via saponification), which may assist in the penetration of the treatment liquid into gaps and small spaces in the treatment sits or to remove bubbles formed during the chemical reaction.

In some embodiments, sodium hypochlorite can be used in the treatment fluid. In embodiments that include sodium hypochlorite in the treatment solution, it should be appreciated that sodium hypochlorite breaks down into hypochlorous acid and sodium hydroxide. The hypochlorous acid may react with free amino acids in the tissue to form N-chloro amino acids. The N-chloro amino acides are strong oxidizing agents that may have a higher antiseptic activity than sodium hypochlorite.

In some embodiments, the cavitation dynamics that result from the generated pressure waves can be modified by adjusting the chemicals used in the treatment fluid. For example, the chemical(s) in the fluid may affect the surface tension of the solution, which in turn may change the cavitation phenomenon. For example, a solution of an inorganic chemical such as, e.g., sodium hypochlorite in water, may increase the ion concentration in the solution which may increase the surface tension of the solution. Increasing the surface tension may advantageously result in stronger cavitation in some cases, which can enhance the cleaning action of the procedure. In some cases, the magnitude of a cavitation inception threshold may increase with increasing surface tension, and the cavitation inducing mechanism (e.g., pressure wave generator) may need to generate waves that are sufficiently intense to pass the threshold in order to have inception of cavitation bubbles. Without being limited by theory, however, it is believed that once the cavitation threshold is passed, increased surface tension may typically result in stronger cavitation. For example, the solution of sodium hypochlorite in water can result in the following equilibrium reaction, which may increase the ionic concentration of the liquid and therefore may improve cavitation in some arrangements.

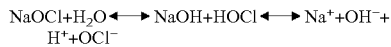

In some embodiments, accelerated bubble removal from the treatment site may be arranged. For example, in some methods, a chemical, such as NaOCl, may cause saponification. The removal of bubbles created or trapped inside the treatment site may be accelerated due to local reduction of surface tension at the chemical reaction front as a result of local saponification. Although in some methods it may be desirable to have a relatively high surface tension at the pressure wave source (e.g., the pressure wave generator), inside the treatment site it may be beneficial to have locally reduced surface tension to accelerate bubble removal. The accelerated bubble removal phenomenon may happen as tissue dissolving agent(s) react with the tissue. For example, sodium hypochlorite can act as a solvent to degrade fatty acids and to transform them into fatty acid salts (soap) and glycerol (alcohol) that can reduce the surface tension of the remaining solution at the chemical reaction front.

Other properties or variables can be adjusted or selected to enhancing the cleaning procedure. For example, a chemical reaction rate can be adjusted for each chemical reaction, which may determine the overall speed of reaction. In some cases, for example, the temperature can be adjusted to adjust the reaction rate. In addition, a concentration of reactants can be an important factor that may affect the time for the reaction to complete, e.g., the time to complete the cleaning of the carious region. For instance, a 5% NaOCl solution generally may be more aggressive than a 0.5% NaOCl solution and may tend to dissolve tissue faster. In some cases, a reactant refreshment rate can be adjusted. For example, bubbles may form and stay at the chemical reaction front (e.g., due to surface tension forces) and may act as barriers at the chemical reaction front impeding or preventing fresh reactants from reaching the reaction front. The circulation of the treatment liquid can help remove the bubbles and the reaction byproducts, and may replace them with fresh treatment liquid.

In some embodiments, the introduction of heat can increase the chemical reaction rate. Heat can be introduced into the system through a variety of source(s). For example, the treatment fluid can be preheated using any suitable heating technique. Further, heat can be generated from cavitation or from other internal or external dissipative sources. In some arrangements, heat can be produced from exothermic chemical reactions that may further enhance or increase reaction rates, which can increase the speed of the cleaning process.

In some arrangements, sonication can occur. For example, upon irradiation of a liquid (e.g. water) with high intensity pressure waves (including, e.g., sonic or ultrasonic waves) acoustic cavitation may occur. The oscillation and/or implosive collapse of the cavitation bubbles can produce intense local heating and high pressures with short lifetimes. Experimental results have shown that at the site of the bubble collapse, the temperature and pressure may reach around 5000 K and 1000 atm, respectively. This phenomenon, known as sonochemistry, can create extreme physical and chemical conditions in otherwise cold liquids. Sonochemistry, in some cases, has been reported to enhance chemical reactivity by as much as a millionfold. Such high temperatures and pressures may assist in removing dental deposits from the tooth. In yet other aspects, however, when acoustic cavitation does not occur (or occurs at a relatively low amplitude), the vibration and agitation of reactants, due to the pressure waves, may enhance the chemical reaction as it assists in replacing the byproducts by fresh reactants. The pressure waves generated by the pressure wave generator can therefore effectively and quickly remove dental deposits from the tooth to be treated.

VIII. Examples of Acoustic Power Generated by Pressure Wave Generators

Figure 13A:
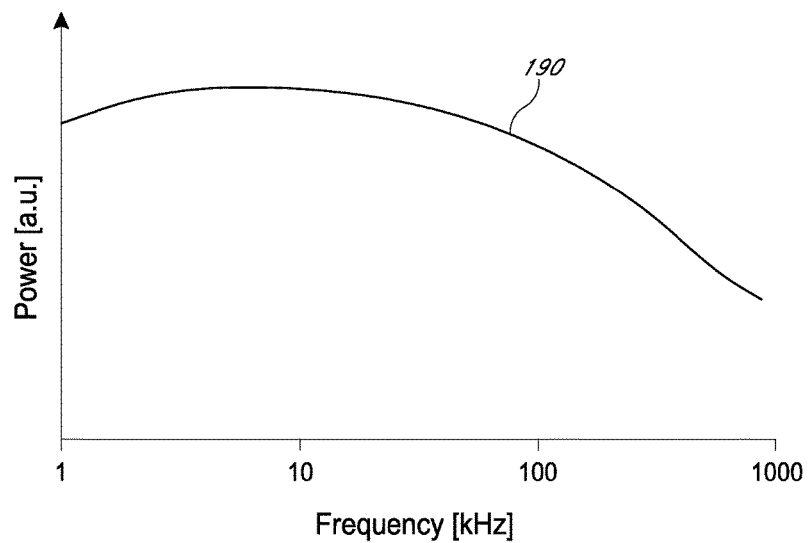
FIGS. 13A and 13B are graphs that schematically illustrate possible examples of acoustic power that could be generated by different embodiments of the pressure wave generator.
Figure 13B:
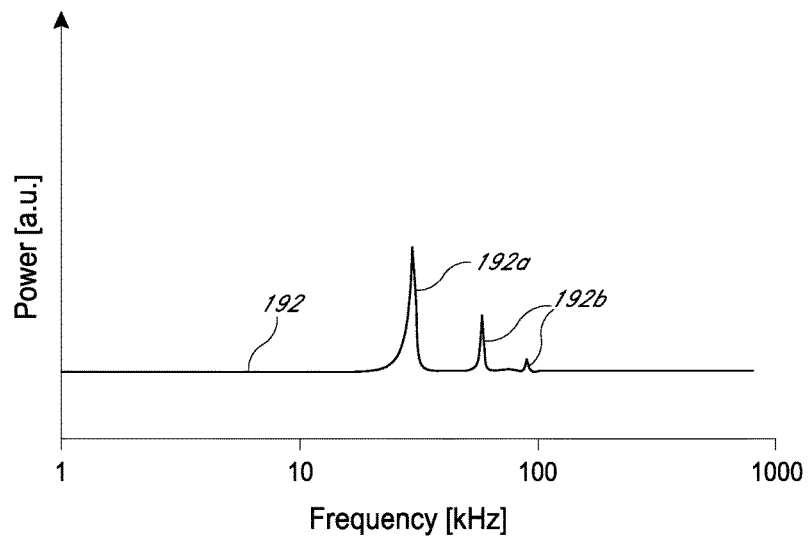

FIGS. 13A and 13B are graphs that schematically illustrate possible examples of acoustic power that could be generated by different embodiments of the pressure wave generator. These graphs schematically show acoustic power (in arbitrary units) on the vertical axis as a function of acoustic frequency (in kHz) on the horizontal axis. The acoustic power in the tooth may influence, cause, or increase the strength of effects including, e.g., acoustic cavitation (e.g., cavitation bubble formation and collapse, microjet formation), acoustic streaming, microerosion, fluid agitation, fluid circulation, sonoporation, sonochemistry, and so forth, which may act to dissociate organic material in or on the tooth and effectively clean the organic and/or inorganic materials and dental deposits. In various embodiments, the pressure wave generator can produce an acoustic wave including acoustic power (at least) at frequencies above: about 1 Hz, about 0.5 kHz, about 1 kHz, about 10 kHz, about 20 kHz, about 50 kHz, about 100 kHz, or greater. The acoustic wave can have acoustic power at other frequencies as well (e.g., at frequencies below the aforelisted frequencies).

The graph in FIG. 13A represents a schematic example of acoustic power generated by a liquid jet impacting a surface disposed within a chamber on or around the tooth that is substantially filled with liquid and by the interaction of the liquid jet with fluid in the chamber. This schematic example shows a broadband spectrum 190 of acoustic power with significant power extending from about 1 Hz to about 1000 kHz, including, e.g., significant power in a range of about 1 kHz to about 1000 kHz (e.g., the bandwidth can be about 1000 kHz). The bandwidth of the acoustic energy spectrum may, in some cases, be measured in terms of the 3-decibel (3-dB) bandwidth (e.g., the full-width at half-maximum or FWHM of the acoustic power spectrum). In various examples, a broadband acoustic power spectrum can include significant power in a bandwidth in a range from about 1 Hz to about 500 kHz, in a range from about 1 kHz to about 500 kHz, in a range from about 10 kHz to about 100 kHz, or some other range of frequencies. In some implementations, a broadband spectrum can include acoustic power above about 1 MHz. In some embodiments, the pressure wave generator can produce broadband acoustic power with peak power at about 10 kHz and a bandwidth of about 100 kHz. In various embodiments, the bandwidth of a broadband acoustic power spectrum is greater than about 10 kHz, greater than about 50 kHz, greater than about 100 kHz, greater than about 250 kHz, greater than about 500 kHz, greater than about 1 MHz, or some other value. In some cleaning methods, acoustic power between about 1 Hz and about 200 kHz, e.g., in a range of about 20 kHz to about 200 kHz may be particularly effective at cleaning teeth. The acoustic power can have substantial power at frequencies greater than about 1 kHz, greater than about 10 kHz, greater than about 100 kHz, or greater than about 500 kHz. Substantial power can include, for example, an amount of power that is greater than 10%, greater than 25%, greater than 35%, or greater than 50% of the total acoustic power (e.g., the acoustic power integrated over all frequencies). In some arrangements, the broadband spectrum 190 can include one or more peaks, e.g., peaks in the audible, ultrasonic, and/or megasonic frequency ranges.

The graph in FIG. 13B represents a schematic example of acoustic power generated by an ultrasonic transducer disposed in a chamber on or around the tooth that is substantially filled with liquid. This schematic example shows a relatively narrowband spectrum 192 of acoustic power with a highest peak 192a near the fundamental frequency of about 30 kHz and also shows peaks 192b near the first few harmonic frequencies. The bandwidth of the acoustic power near the peak may be about 5 to 10 kHz, and can be seen to be much narrower than the bandwidth of the acoustic power schematically illustrated in FIG. 13A. In other embodiments, the bandwidth of the acoustic power can be about 1 kHz, about 5 kHz, about 10 kHz, about 20 kHz, about 50 kHz, about 100 kHz, or some other value. The acoustic power of the example spectrum 192 has most of its power at the fundamental frequency and first few harmonics, and therefore the ultrasonic transducer of this example may provide acoustic power at a relatively narrow range of frequencies (e.g., near the fundamental and harmonic frequencies). The acoustic power of the example spectrum 190 exhibits relatively broadband power (with a relatively high bandwidth compared to the spectrum 192), and the example liquid jet can provide acoustic power at significantly more frequencies than the example ultrasonic transducer. For example, the relatively broadband power of the example spectrum 190 illustrates that the example jet device provides acoustic power at these multiple frequencies with energy sufficient to break the bonds between the decayed and healthy material so as to substantially remove the decayed material from the carious region.

It is believed, although not required, that acoustic waves having broadband acoustic power (see, e.g., the example shown in FIG. 13A) can generate acoustic cavitation or other means of cleaning and disinfection that is more effective at cleaning teeth (including cleaning, e.g., undesirable dental deposits in or on the tooth) than cavitation generated by acoustic waves having a narrowband acoustic power spectrum (see, e.g., the example shown in FIG. 13B). For example, a broadband spectrum of acoustic power can produce a relatively broad range of bubble sizes in the cavitation cloud and on the surfaces on the tooth, and the implosion of these bubbles may be more effective at disrupting tissue than bubbles having a narrow size range. Relatively broadband acoustic power may also allow acoustic energy to work on a range of length scales, e.g., from the cellular scale up to the tissue scale. Accordingly, pressure wave generators that produce a broadband acoustic power spectrum (e.g., some embodiments of a liquid jet) can be more effective at tooth cleaning for some treatments than pressure wave generators that produce a narrowband acoustic power spectrum. In some embodiments, multiple narrowband pressure wave generators can be used to produce a relatively broad range of acoustic power. For example, multiple ultrasonic tips, each tuned to produce acoustic power at a different peak frequency, can be used. As used herein, broadband frequencies and broadband frequency spectrum is defined regardless of secondary effects such as harmonics of the main frequencies and regardless of any noise introduced by measurement or data processing (e.g., FFT); that is, these terms should be understood when only considering all main frequencies activated by the pressure wave generator.

Figure 14:
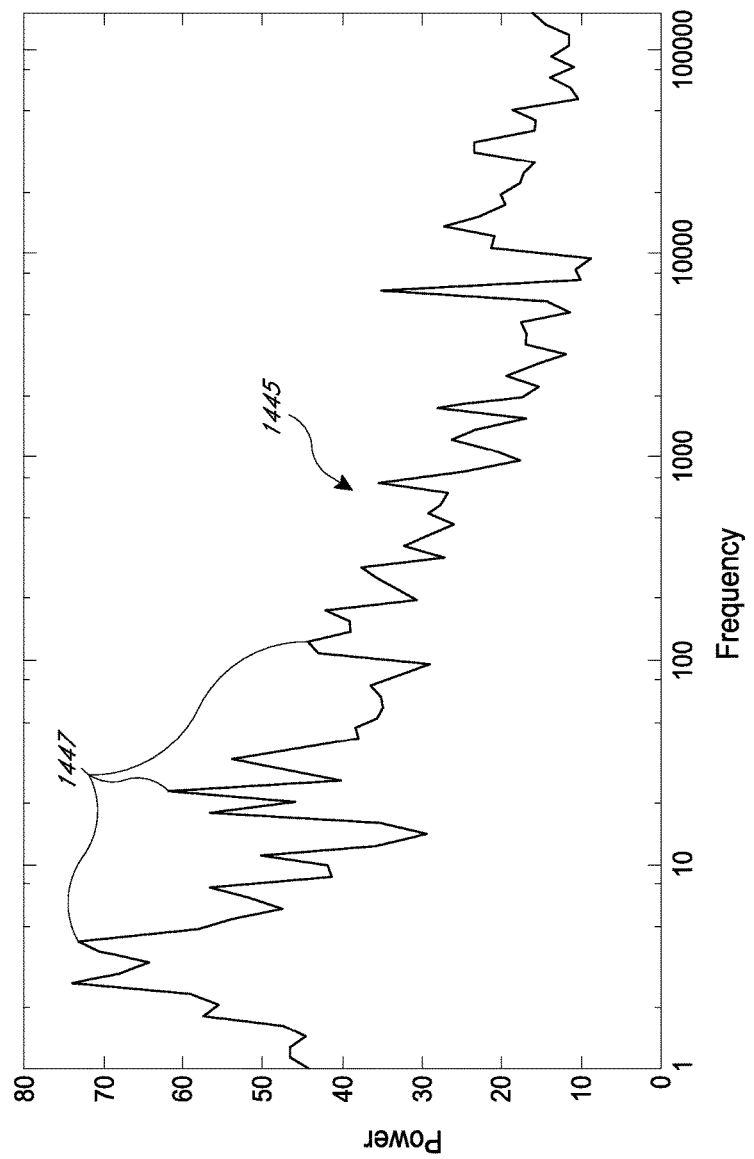
FIG. 14 is a graph of an acoustic power spectrum generated at multiple frequencies by a pressure wave generator.

FIG. 14 is a graph of an acoustic power spectrum 1445 generated at multiple frequencies by the pressure wave generators disclosed herein. For example, the spectrum 1445 in FIG. 14 is an example of acoustic power generated by a liquid jet impacting a surface disposed within a chamber on, in, or around the tooth that is substantially filled with liquid and by the interaction of the liquid jet with fluid in the chamber. The spectrum 1445 of FIG. 14 represents acoustic power detected by a sensor spaced apart from the source of the acoustic energy, e.g., the pressure wave generator. The data was acquired inside an insulated water tank data when the distance between the power wave generator and the hydrophone (e.g., sensor) being about 8 inches. The vertical axis of the plot represents a measure of acoustic power: Log $(P_{acoustic}^2)$, referred to herein as "power units". The units of $P_{acoustic}$ in the measurement were µPa (micro Pascal). Thus, it should be appreciated that the actual power at the source may be of a different magnitude because the sensor is spaced from the acoustic power generator. However, the general profile of the power spectrum at the source should be the same as the spectrum 1445 detected at the sensor and plotted in FIG. 14. It should also be understood that, although the plot shows frequencies only up to 100 KHz, the power above 100 KHz was greater than zero—the data just was not plotted. It should further be noted that, as would be appreciated by one skilled in the art, the plot and the values would also depend on other parameters, such as, for example, the size and shape of the tank in which data was acquired, the insulation of the inner surface of the tank, the relative distance between the source (e.g., power wave generator), and the free water surface of the tank. As shown in FIG. 14, the spectrum 1445 can include acoustic power at multiple frequencies 1447, e.g., multiple discrete frequencies. In particular, the spectrum 1445 illustrated in FIG. 14 includes acoustic power at frequencies in a range of about 1 Hz to about 100 KHz. The acoustic power can be in a range of about 10 power units to about 80 power units at these frequencies. In some arrangements, the acoustic power can be in a range of about 30 power units to about 75 power units at frequencies in a range of about 1 Hz to about 10 kHz. In some arrangements, the acoustic power can be in a range of about 10 power units to about 30 power units at frequencies in a range of about 1 KHz to about 100 kHz.

Pressure wave generators that generate acoustic power associated with the spectrum 1445 of FIG. 14 can advantageously and surprisingly clean undesirable deposits and decayed matter from exterior surfaces of teeth. As explained above, the generation of power at multiple frequencies can help to remove various types of organic and/or inorganic materials that have different material or physical characteristics, and/or different bonding strengths at various frequencies. For example, some undesirable deposits may be removed from the teeth and/or gums at relatively low acoustic frequencies, while other deposits may be removed from the teeth and/or gums at relatively high acoustic frequencies, while still other deposits may be removed at intermediate frequencies between the relatively low and relatively high frequencies. As shown in FIG. 14, lower frequency cleaning phases can be activated at higher powers, and higher frequency cleaning phases can be activated at lower powers. In other embodiments, low frequency cleaning phases may be activated at relatively low powers, and high frequency cleaning phases may be activated at relatively high powers. Pressure wave generators that generate acoustic power at multiple frequencies (e.g., multiple discrete frequencies) are capable of cleaning undesirable dental deposits and decayed matter from exterior surfaces of teeth.

In the embodiments disclosed herein, treatment procedures can be activated to generate acoustic power at various frequency ranges. For example, as explained above, some treatment phases may be activated at lower frequencies, and other treatment phases may be activated at higher frequencies. The pressure wave generators disclosed herein can be adapted to controllably generate acoustic power at any suitable frequencies 1447 of the spectrum 1445. For example, the pressure wave generators disclosed herein can be adapted to generate power at multiple frequencies 1447 simultaneously, e.g., such that the delivered acoustic power in a particular treatment procedure can include a desired combination of individual frequencies. For example, in some procedures, power may be generated across the entire frequency spectrum 1445. In some treatment phases, the pressure wave generator can deliver acoustic power at only relatively low frequencies, and in other treatment phases, the pressure wave generator can deliver power at only relatively high frequencies, as explained herein. Further, depending on the desired treatment procedure, the pressure wave generator can automatically or manually transition between frequencies 1447 according to a desired pattern, or can transition between frequencies 1447 randomly.

IX. Degassed Treatment Fluids

As will be described below, the treatment fluid (and/or any of solutions added to the treatment fluid) can be degassed compared to normal liquids used in dental offices. For example, degassed distilled water can be used (with or without the addition of chemical agents or solutes).

(1) Examples of Possible Effects of Dissolved Gases in the Treatment Fluid

In some procedures, the treatment fluid can include dissolved gases (e.g., air). For example, the fluids used in dental offices generally have a normal dissolved gas content (e.g., determined from the temperature and pressure of the fluid based on Henry's law). During cleaning procedures using a pressure wave generator, the acoustic field of the pressure wave generator and/or the flow or circulation of fluids in the chamber can cause some of the dissolved gas to come out of solution and form bubbles.

The bubbles can block small passageways or cracks or surface irregularities in the tooth, and such blockages can act as if there were a "vapor lock" in the small passageways. In some such procedures, the presence of bubbles may at least partially block, impede, or redirect propagation of acoustic waves past the bubbles and may at least partially inhibit or prevent cleaning action from reaching, for example, dental deposits such as stains, calculus, caries, biofilms, plaque, tartar, etc. from the tooth or from the gingival sulcus, periodontal pockets, gums etc., or other organic and/or inorganic materials. The bubbles may block fluid flow or circulation from reaching these difficult-to-reach, or otherwise small, regions, which may prevent or inhibit a treatment solution from reaching these areas of the tooth.

In certain procedures, cavitation is believed to play a role in cleaning the tooth. Without wishing to be bound by any particular theory, the physical process of cavitation inception may be, in some ways, similar to boiling. One possible difference between cavitation and boiling is the thermodynamic paths that precede the formation of the vapor in the fluid. Boiling can occur when the local vapor pressure of the liquid rises above the local ambient pressure in the liquid, and sufficient energy is present to cause the phase change from liquid to a gas. It is believed that cavitation inception can occur when the local ambient pressure in the liquid decreases sufficiently below the saturated vapor pressure, which has a value given in part by the tensile strength of the liquid at the local temperature. Therefore, it is believed, although not required, that cavitation inception is not determined by the vapor pressure, but instead by the pressure of the largest nuclei, or by the difference between the vapor pressure and the pressure of the largest nuclei. As such, it is believed that subjecting a fluid to a pressure slightly lower than the vapor pressure generally does not cause cavitation inception. However, the solubility of a gas in a liquid is proportional to pressure; therefore lowering the pressure may tend to cause some of the dissolved gas inside the fluid to be released in the form of gas bubbles that are relatively large compared to the size of bubbles formed at cavitation inception. These relatively large gas bubbles may be misinterpreted as being vapor cavitation bubbles, and their presence in a fluid may have been mistakenly described in certain reports in the literature as being caused by cavitation, when cavitation may not have been present.

In the last stage of collapse of vapor cavitation bubbles, the velocity of the bubble wall may even exceed the speed of sound and create strong shock waves inside the fluid. The vapor cavitation bubble may also contain some amount of gas, which may act as a buffer and slow down the rate of collapse and reduce the intensity of the shockwaves. Therefore, in certain procedures that utilize cavitation bubbles for tooth cleaning, it may be advantageous to reduce the amount of the dissolved air in the fluid to prevent such losses.

The presence of bubbles that have come out of solution from the treatment fluid may lead to other disadvantages during certain procedures. For example, if the pressure wave generator produces cavitation, the agitation (e.g. pressure drop) used to induce the cavitation may cause the release of the dissolved air content before the water molecules have a chance to form a cavitation bubble. The already-formed gas bubble may act as a nucleation site for the water molecules during the phase change (which was intended to form a cavitation bubble). When the agitation is over, the cavitation bubble is expected to collapse and create pressure waves. However, cavitation bubble collapse might happen with reduced efficiency, because the gas-filled bubble may not collapse and may instead remain as a bubble. Thus, the presence of gas in the treatment fluid may reduce the effectiveness of the cavitation process as many of the cavitation bubbles may be wasted by merging with gas-filled bubbles. Additionally, bubbles in the fluid may act as a cushion to damp pressure waves propagating in the region of the fluid comprising the bubbles, which may disrupt effective propagation of the pressure waves past the bubbles. Some bubbles may either form on or between tooth surfaces, or be transferred there by the flow or circulation of fluid in the tooth. The bubbles may be hard to remove due to relatively high surface tension forces. This may result in blocking the transfer of chemicals and/or pressure waves into the irregular surfaces and small spaces in and between teeth, and therefore may disrupt or reduce the efficacy of the treatment.

(2) Examples of Degassed Treatment Fluids

Accordingly, it may be advantageous in some systems and methods to use a degassed fluid, which can inhibit, reduce, or prevent bubbles from coming out of solution during treatments as compared to systems and methods that use normal (e.g., non-degassed) fluids. In dental procedures in which the treatment fluid has a reduced gas content (compared with the normal fluids) tooth surfaces or tiny spaces between teeth may be free of bubbles that have come out of solution. Acoustic waves generated by the pressure wave generator can propagate through the degassed fluid to reach and clean the surfaces, cracks, and tooth spaces and cavities. In some procedures, the degassed fluid can be able to penetrate spaces as small as about 500 microns, 200 microns, 100 microns, 10 microns, 5 microns, 1 micron, or smaller, because the degassed fluid is sufficiently gas-free that bubbles are inhibited from coming out of solution and blocking these spaces (as compared to use of fluids with normal dissolved gas content).

For example, in some systems and methods, the degassed fluid can have a dissolved gas content that is reduced when compared to the "normal" gas content of water. For example, according to Henry's law, the "normal" amount of dissolved air in water (at 25 C and 1 atmosphere) is about 23 mg/L, which includes about 9 mg/L of dissolved oxygen and about 14 mg/L of dissolved nitrogen. In some embodiments, the degassed fluid has a dissolved gas content that is reduced to approximately 10%-40% of its "normal" amount as delivered from a source of fluid (e.g., before degassing). In other embodiments, the dissolved gas content of the degassed fluid can be reduced to approximately 5%-50% or 1%-70% of the normal gas content of the fluid. In some treatments, the dissolved gas content can be less than about 70%, less than about 50%, less than about 40%, less than about 30%, less than about 20%, less than about 10%, less than about 5%, or less than about 1% of the normal gas amount.

In some embodiments, the amount of dissolved gas in the degassed fluid can be measured in terms of the amount of dissolved oxygen (rather than the amount of dissolved air), because the amount of dissolved oxygen can be more readily measured (e.g., via titration or optical or electrochemical sensors) than the amount of dissolved air in the fluid. Thus, a measurement of dissolved oxygen in the fluid can serve as a proxy for the amount of dissolved air in the fluid. In some such embodiments, the amount of dissolved oxygen in the degassed fluid can be in a range from about 1 mg/L to about 3 mg/L, in a range from about 0.5 mg/L to about 7 mg/L, or some other range. The amount of dissolved oxygen in the degassed fluid can be less than about 7 mg/L, less than about 6 mg/L, less than about 5 mg/L, less than about 4 mg/L, less than about 3 mg/L, less than about 2 mg/L, or less than about 1 mg/L.

In some embodiments, the amount of dissolved gas in the degassed fluid can be in a range from about 2 mg/L to about 20 mg/L, in a range from about 1 mg/L to about 12 mg/L, or some other range. The amount of dissolved gas in the degassed fluid can be less than about 20 mg/L, less than about 18 mg/L, less than about 15 mg/L, less than about 12 mg/L, less than about 10 mg/L, less than about 8 mg/L, less than about 6 mg/L, less than about 4 mg/L, or less than about 2 mg/L.

In other embodiments, the amount of dissolved gas can be measured in terms of air or oxygen percentage per unit volume. For example, the amount of dissolved oxygen (or dissolved air) can be less than about 5% by volume, less than about 1% by volume, less than about 0.5% by volume, or less than about 0.1% by volume.

The amount of dissolved gas in a liquid can be measured in terms of a physical property such as, e.g., fluid viscosity or surface tension. For example, degassing water tends to increase its surface tension. The surface tension of non-degassed water is about 72 mN/m at 20° C. In some embodiments, the surface tension of degassed water can be about 1%, 5%, or 10% greater than non-degassed water.

In some treatment methods, one or more secondary fluids can be added to a primary degassed fluid (e.g., an antiseptic solution can be added to degassed distilled water). In some such methods, the secondary solution(s) can be degassed before being added to the primary degassed fluid. In other applications, the primary degassed fluid can be sufficiently degassed such that inclusion of the secondary fluids (which can have normal dissolved gas content) does not increase the gas content of the combined fluids above what is desired for a particular dental treatment.

In various implementations, the treatment fluid can be provided as degassed liquid inside sealed bags or containers. The fluid can be degassed in a separate setup in the operatory before being added to a fluid reservoir. In an example of an "in-line" implementation, the fluid can be degassed as it flows through the system, for example, by passing the fluid through a degassing unit attached along a fluid line (e.g., the fluid inlet). Examples of degassing units that can be used in various embodiments include: a Liqui-Cel® MiniModule® Membrane Contactor (e.g., models 1.7×5.5 or 1.7×8.75) available from Membrana-Charlotte (Charlotte, N.C.); a PermSelect® silicone membrane module (e.g., model PDM-SXA-2500) available from MedArray, Inc. (Ann Arbor, Mich.); and a FiberFlo® hollow fiber cartridge filter (0.03 micron absolute) available from Mar Cor Purification (Skippack, Pa.). The degassing can be done using any of the following degassing techniques or combinations of thereof: heating, helium sparging, vacuum degassing, filtering, freeze-pump-thawing, and sonication.

In some embodiments, degassing the fluid can include de-bubbling the fluid to remove any small gas bubbles that form or may be present in the fluid. De-bubbling can be provided by filtering the fluid. In some embodiments, the fluid may not be degassed (e.g., removing gas dissolved at the molecular level), but can be passed through a de-bubbler to remove the small gas bubbles from the fluid.

In some embodiments, a degassing system can include a dissolved gas sensor to determine whether the treatment fluid is sufficiently degassed for a particular treatment. A dissolved gas sensor can be disposed downstream of a mixing system and used to determine whether mixing of solutes has increased the dissolved gas content of the treatment fluid after addition of solutes, if any. A solute source can include a dissolved gas sensor. For example, a dissolved gas sensor can measure the amount of dissolved oxygen in the fluid as a proxy for the total amount of dissolved gas in the fluid, since dissolved oxygen can be measured more readily than dissolved gas (e.g., nitrogen or helium). Dissolved gas content can be inferred from dissolved oxygen content based at least partly on the ratio of oxygen to total gas in air (e.g., oxygen is about 21% of air by volume). Dissolved gas sensors can include electrochemical sensors, optical sensors, or sensors that perform a dissolved gas analysis. Examples of dissolved gas sensors that can be used with embodiments of various systems disclosed herein include a Pro-Oceanus GTD-Pro or HGTD dissolved gas sensor available from Pro-Oceanus Systems Inc. (Nova Scotia, Canada) and a D-Opto dissolved oxygen sensor available from Zebra-Tech Ltd. (Nelson, New Zealand). In some implementations, a sample of the treatment can be obtained and gases in the sample can be extracted using a vacuum unit. The extracted gases can be analyzed using a gas chromatograph to determine dissolved gas content of the fluid (and composition of the gases in some cases).

Accordingly, fluid delivered to the tooth from a fluid inlet and/or the fluid used to generate the jet in a liquid jet device can comprise a degassed fluid that has a dissolved gas content less than normal fluid. The degassed fluid can be used, for example, to generate the high-velocity liquid beam for generating pressure waves, to substantially fill or irrigate a chamber (e.g., the chamber between the fluid retainer and tooth), to provide a propagation medium for acoustic waves, to inhibit formation of air (or gas) bubbles in the chamber (e.g., in small spaces or cracks in or between teeth), and/or to provide flow of the degassed fluid into small spaces in the tooth (e.g., cracks, irregular surfaces, tubules, etc.). In embodiments utilizing a liquid jet, use of a degassed fluid can inhibit bubbles from forming in the jet due to the pressure drop at a nozzle orifice where the liquid jet is formed.

Thus, examples of methods for endodontic treatment comprise flowing a degassed fluid onto a tooth or tooth surface or into a chamber. The degassed fluid can comprise a tissue dissolving agent and/or a decalcifying agent. The degassed fluid can have a dissolved oxygen content less than about 9 mg/L, less than about 7 mg/L, less than about 5 mg/L, less than about 3 mg/L, less than about 1 mg/L, or some other value. A fluid for treatment can comprise a degassed fluid with a dissolved oxygen content less than about 9 mg/L, less than about 7 mg/L, less than about 5 mg/L, less than about 3 mg/L, less than about 1 mg/L, or some other value. The fluid can comprise a tissue dissolving agent and/or a decalcifying agent. For example, the degassed fluid can comprise an aqueous solution of less than about 6% by volume of a tissue dissolving agent and/or less than about 20% by volume of a decalcifying agent.

Although the tooth schematically depicted in some of the figures is a molar, the procedures can be performed on any type of tooth such as an incisor, a canine, a bicuspid, a pre-molar, or a molar. Further, although the tooth may be depicted as a lower (mandibular) tooth in the figures, this is for purposes of illustration, and is not limiting. The systems, methods, and compositions can be applied to lower (mandibular) teeth or upper (maxillary) teeth. Also, the disclosed apparatus and methods are capable of any portions of a tooth. Moreover, the disclosed apparatus, methods, and compositions can be applied to human teeth (including juvenile teeth) and/or to animal teeth.

Reference throughout this specification to "some embodiments" or "an embodiment" means that a particular feature, structure, element, act, or characteristic described in connection with the embodiment is included in at least one embodiment. Thus, appearances of the phrases "in some embodiments" or "in an embodiment" in various places throughout this specification are not necessarily all referring to the same embodiment and may refer to one or more of the same or different embodiments. Furthermore, the particular features, structures, elements, acts, or characteristics may be combined in any suitable manner (including differently than shown or described) in other embodiments. Further, in various embodiments, features, structures, elements, acts, or characteristics can be combined, merged, rearranged, reordered, or left out altogether. Thus, no single feature, structure, element, act, or characteristic or group of features, structures, elements, acts, or characteristics is necessary or required for each embodiment. All possible combinations and subcombinations are intended to fall within the scope of this disclosure.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The foregoing description sets forth various example embodiments and other illustrative, but non-limiting, embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method or process may be performed in any suitable sequence and are not necessarily limited to any particular disclosed sequence.

What is claimed is:

1. A system for removing dental deposits from an exterior surface of one or more teeth or gum tissue in a mouth of a mammal, the system comprising:
   a mouthpiece sized and shaped to be inserted into the mouth; and
   an active energy outlet comprising a fluid motion source in fluid communication with the mouthpiece, the fluid motion source comprising one or more fluid ports, the fluid motion source configured to deliver liquid to the mouth and to remove liquid from the mouth through the one or more fluid ports,
   wherein the active energy outlet is operable to create oscillatory movement of liquid to and from the mouth through the one or more fluid ports at variable frequencies, including oscillatory movement of liquid to and from the mouth within a first frequency range during a first treatment phase and within a second frequency range during a second treatment phase, the second frequency range differing from the first frequency range.

2. The system of claim 1, wherein the second frequency range includes higher frequencies than the first frequency range.

3. The system of claim 2, wherein a volume of liquid moving to and from the mouth during the first treatment phase is larger than a volume of liquid moving to and from the mouth during the second treatment phase.

4. The system of claim 3, wherein the first treatment phase is performed before the second treatment phase.

5. The system of claim 2, wherein the active energy outlet is configured to create oscillatory movement of liquid to and from the mouth at frequencies that increase over time from a first frequency in the first frequency range to a second frequency in the second frequency range.

6. The system of claim 2, wherein the active energy outlet is configured to randomly change the frequencies of the oscillatory movement of liquid to and from the mouth.

7. The system of claim 2, wherein the first treatment phase at least partially overlaps the second treatment phase.

8. The system of claim 2, wherein the first frequency range includes frequencies in a range of about 0.1 Hz to about 20 kHz.

9. The system of claim 2, wherein the second frequency range includes frequencies in a range of about 20 kHz to about 1,000 kHz.

10. The system of claim 1, wherein the mouthpiece is shaped to conform to a maxillary or a mandibular arch.

11. The system of claim 1, wherein the mouthpiece comprises a switch configured to activate the active energy outlet.

12. The system of claim 11, wherein the switch is configured to activate the active energy outlet when the mammal bites on the mouthpiece.

13. The system of claim 1, further comprising a fluid driver and a control mechanism configured to control the operation of the fluid driver.

14. The system of claim 13, wherein the control mechanism is configured to balance an amount of liquid delivered to the mouth and removed from the mouth during a cleaning procedure.

15. The system of claim 14, wherein the control mechanism is configured to at least partially fill the mouth with liquid in a start-up phase of a treatment procedure.

16. The system of claim 15, further comprising a sensor configured to monitor a pressure of the liquid in the mouth.

17. The system of claim 1, wherein the active energy outlet further comprises a pressure wave generator configured to generate pressure waves in the liquid.

18. The system of claim 17, wherein the pressure wave generator comprises a liquid jet device.

19. The system of claim 18, further comprising at least one pump that provides pressurized liquid to the liquid jet device.

20. The system of claim 17, wherein the fluid motion source comprises a pump that drives the liquid to the one or more ports.

21. The system of claim 20, wherein, during the first treatment phase, the pump is activated to supply liquid through the one or more ports at frequencies in the first frequency range while the pressure wave generator is inactivated, and wherein, during the second treatment phase, the pump is inactivated and the pressure wave generator is activated to produce frequencies in the liquid in the second frequency range.

22. The system of claim 21, wherein volumetric movement of the liquid in the second treatment phase is less than volumetric movement of the liquid in the first treatment phase.

23. The system of claim 20, wherein, during at least a portion of one of the first and second treatment phases, the pressure wave generator and the pump are activated concurrently.

24. The system of claim 17, wherein the pressure wave generator is configured to generate a broadband power spectrum with multiple discrete frequencies.

25. The system of claim 24, wherein the pressure wave generator is configured to generate pressure waves having power in a range of about 10 power units to about 80 power units at frequencies in a range of about 1 Hz to about 100 kHz, wherein a power unit is defined as Log $(P_{acoustic}^2)$ with $P_{acoustic}$ measured in micro Pascals (µPa).

26. The system of claim 25, wherein the pressure wave generator is configured to generate pressure waves having power in a range of about 30 power units to about 75 power units at frequencies in a range of about 1 Hz to about 10 kHz.

27. The system of claim 25, wherein the pressure wave generator is configured to generate pressure waves having power in a range of about 10 power units to about 30 power units at frequencies in a range of about 1 kHz to about 100 kHz.

28. The system of claim 17, wherein the pressure wave generator is configured to generate a coherent energy beam.

29. The system of claim 28, wherein the pressure wave generator comprises a laser device.

30. The system of claim 1, wherein the fluid motion source comprises a pump that drives the liquid to the one or more ports.

31. A system for removing dental deposits from an exterior surface of one or more teeth or gum tissue in a mouth of a mammal, the system comprising:
   a mouthpiece sized and shaped to be inserted into the mouth;
   an active energy outlet comprising a fluid motion source in fluid communication with the mouthpiece, the fluid motion source comprising one or more fluid ports, the fluid motion source configured to deliver liquid to the mouth and to remove liquid from the mouth through the one or more fluid ports; and
   a control mechanism configured to control the operation of the active energy outlet,
   wherein the active energy outlet is operable to create oscillatory movement of liquid to and from the mouth through the one or more fluid ports at variable frequencies,
   wherein the control mechanism is configured to shut off the fluid motion source if a monitored pressure reaches a level unsafe for the mammal.

32. A method for removing dental deposits from an exterior surface of one or more teeth or gum tissue in a mouth of a mammal, the method comprising:
   inserting a mouthpiece into the mouth, the mouthpiece including one or more fluid ports;
   activating a fluid motion source that is in fluid communication with the mouthpiece to deliver liquid to the mouth and to remove liquid from the mouth through the one or more ports;
   creating oscillatory movement of liquid to and from the mouth through the one or more ports at variable frequencies during at least first and second treatment phases, wherein creating oscillatory movement comprises:
      creating oscillatory movement of liquid to and from the mouth at a first frequency range during the first treatment phase; and
      creating oscillatory movement of liquid to and from the mouth at a second frequency range during the second treatment phase, the second frequency range differing from the first frequency range.

33. The method of claim 32, wherein the second frequency range includes higher frequencies than the first frequency range.

34. The method of claim 33, wherein a volume of liquid moving to and from the mouth during the first treatment phase is larger than a volume of liquid moving to and from the mouth during the second treatment phase.

35. The method of claim 33, further comprising performing the first treatment phase before performing the second treatment phase.

36. The method of claim 33, wherein creating oscillatory movement comprises creating oscillatory movement of liquid to and from the mouth at frequencies that increase over time from a first frequency in the first frequency range to a second frequency in the second frequency range.

37. The method of claim 33, wherein the first frequency range includes frequencies in a range of about 0.1 Hz to about 20 kHz.

38. The method of claim 33, wherein the second frequency range includes frequencies in a range of about 20 kHz to about 1,000 kHz.

39. The method of claim 32, wherein creating oscillatory movement comprises randomly changing the frequencies of the oscillatory movement of liquid to and from the mouth.

40. The method of claim 32, further comprising causing the mammal to bite the mouthpiece to activate the fluid motion source.

41. The method of claim 32, further comprising balancing an amount of liquid delivered to the mouth and removed from the mouth during a cleaning procedure.

42. The method of claim 41, further comprising at least partially filling the mouth with liquid in a start-up phase of a treatment procedure.

43. The method of Claim 32, further comprising monitoring a pressure of the liquid in the mouth during a cleaning procedure.

* * * * *